(12) United States Patent
Pederson et al.

(10) Patent No.: US 6,696,597 B2
(45) Date of Patent: Feb. 24, 2004

(54) METATHESIS SYNTHESES OF PHEROMONES OR THEIR COMPONENTS

(75) Inventors: Richard L. Pederson, San Gabriel, CA (US); Robert H. Grubbs, South Pasadena, CA (US)

(73) Assignee: TillieChem, Inc., San Gabriel, CA (US)

( * ) Notice: Subject to any disclaimer, the term of this patent is extended or adjusted under 35 U.S.C. 154(b) by 332 days.

(21) Appl. No.: 09/833,018

(22) Filed: Apr. 10, 2001

(65) Prior Publication Data

US 2002/0022741 A1 Feb. 21, 2002

Related U.S. Application Data

(63) Continuation-in-part of application No. 09/387,486, filed on Sep. 1, 1999, now Pat. No. 6,215,019.
(60) Provisional application No. 60/098,792, filed on Sep. 1, 1998, and provisional application No. 60/166,543, filed on Nov. 18, 1999.

(30) Foreign Application Priority Data

Nov. 17, 2000 (WO) .............................. PCT/US00/31549

(51) Int. Cl.$^7$ .............................................. C07C 67/04
(52) U.S. Cl. ..................................... 560/247; 560/231
(58) Field of Search ................... 560/247, 231

(56) References Cited

U.S. PATENT DOCUMENTS

| | | | |
|---|---|---|---|
| 3,721,718 A | 3/1973 | Hughes et al. | 260/683 D |
| 4,844,916 A | 7/1989 | Ogawa et al. | 424/409 |
| 4,923,119 A | 5/1990 | Yamamoto et al. | 239/55 |
| 5,312,940 A | 5/1994 | Grubbs et al. | 556/136 |
| 5,342,909 A | 8/1994 | Grubbs et al. | 526/171 |
| 5,775,026 A | 7/1998 | Pearce et al. | 43/124 |
| 5,831,108 A | 11/1998 | Grubbs et al. | |
| 5,916,983 A | 6/1999 | Pederson et al. | 526/170 |
| 5,917,071 A | 6/1999 | Grubbs et al. | 556/21 |
| 5,969,170 A | 10/1999 | Grubbs et al. | 556/21 |
| 5,977,393 A | 11/1999 | Grubbs et al. | 556/21 |
| 6,111,121 A | 8/2000 | Grubbs et al. | 556/21 |
| 6,211,391 B1 | 4/2001 | Grubbs et al. | 556/21 |
| 6,215,019 B1 | 4/2001 | Pederson et al. | 560/234 |
| 6,225,488 B1 | 5/2001 | Mukerjee et al. | 556/22 |
| 6,376,690 B1 | 4/2002 | Grubbs et al. | 556/21 |

FOREIGN PATENT DOCUMENTS

| | | | | |
|---|---|---|---|---|
| WO | WO 96/04289 | 2/1996 | ............ | C07F/15/00 |
| WO | WO 98/39346 | 9/1998 | ............ | C07F/15/00 |
| WO | WO 99/00396 | 1/1999 | ............ | C07F/15/00 |
| WO | WO 99/00397 | 1/1999 | ............ | C07F/15/00 |
| WO | WO 99/28330 | 6/1999 | ............ | C07F/15/00 |
| WO | WO 99/29701 | 6/1999 | ............ | C07F/15/00 |
| WO | WO 99/50330 | 10/1999 | ............ | C08G/61/00 |
| WO | WO 99/51344 | 10/1999 | ............ | B01J/31/22 |
| WO | WO 00/15339 | 3/2000 | ............ | B01J/31/00 |
| WO | WO 00/43343 | 7/2000 | ............ | C07C/41/30 |
| WO | WO 00/58322 | 10/2000 | ............ | C07F/15/00 |
| WO | WO 00/71554 A2 | 11/2000 | ............ | C07F/15/00 |

OTHER PUBLICATIONS

Arduengo et al., *Acc. Chem. Res.* 32:913–921 (1999).
Bourissou et al. *Chem. Rev.* 100–39–91 (2000).
Corriu et al. *Chem Cinnyb*, 168–169 (1980).
Dervan et al. *J.Amer. Chem. Soc.* 98, 1265–1267 (1976).
Fürstner et al., *Angew. Chem., Int. Ed.* 39:3012–3043 (2000).
Huang et al., *J. Am. Chem. Soc.* 121:2674–2678 (1999).
Ivin et al., *J. Mol. Catal. A: Chem.* 133:1–16(1998).
Jafarpour et al., Organometallics 19 (11):2055–2057 (2000).
Randall et al., *J. Mol. Cat. A–Chem.* 133, 29–40 (1998).
Scholl et al., *Tetrahedron Letter* 40; 2247–22500 (1999).
Schwab et al., Angew, Chem., Int. Ed. Engl. 34:2039–2041 (1995).
Still, *J. Org. Chem.* 41, 3063 (1976).
(Trnka et al., *Acc. Chem Res.* 34:18–29 (2001).
Couturier, J.L. et al., *Angew. Chem. Int. Ed. Engl.* (1992) 31, 628, "A Cyclometalated Aryloxy(chloro)neopentylidene-tungsten Complex: A Highly Active and Stereoselective Catalyst for the Metathesis of cis– and trans–2–Pentene, Norbornene, 1–Methyl–norbornene, and Ethyl Oleate".
J.W. Ellis et al. *Inorg. Chem.* (1992) 31, 3026–3033, "Water– Soluble Tris(hydroxymethyl)phosphine Complexes with Nickel, Palladium, and Platinum, Crystal Structure of [PD{P(CH$_2$OH)$_3$}$_4$]•CH$_3$OH".
N.J. Goodwin et al., *Chem. Commun.* (1996) 1551, FcCH$_2$P(CH$_2$ OH)$_2$: a new, reactive yet air–stable ferrocene– derived phosphine [Fc=(η•C$_5$H$_5$)FeC$_5$H$_4$].
Grubbs et al., *Tetrahedron* (1998), 54, 4413–4450, "Recent Advances in Olefin Metathesis and Its Application in Organic Synthesis".

(List continued on next page.)

Primary Examiner—Paul J. Killos
(74) *Attorney, Agent, or Firm*—Stoel Rives LLP

(57) ABSTRACT

The present invention relates to metathesis syntheses for insect sex-attractant pheromones or their components, such as E-5-decenyl acetate, the major component of the Peach Twig Borer pheromone; (5R,6S)-6-acetoxy-5-hexadecanolide, the mosquito oviposition attractant pheromone; E9,Z11-hexadecadienal, the pecan nut casebearer moth pheromone; 9-tetradecenyl formate, an analog of the Diamondback Moth (DBM) pheromone; 11-tetradecenyl acetate, the Omnivorous Leafroller (OLR) pheromone; E-4-tridecenyl acetate, the major component of the Tomato Pinworm (TPW) pheromone; E,E-8,10-dodecadienol, the Codling Moth (CM) pheromone. The syntheses preferably employ a Class I–IV metathesis catalyst, entail few reaction steps, use generally commercially available starting materials, and have relatively short process times. These syntheses produce good yields without the need for expensive or sophisticated equipment. The invention also provides an inexpensive route for producing omega-haloalkenols by cross-metathesizing alpha-omega-diacetoxy alkenes and alpha-omega-dihalides to yield omega-haloalkenols, which are easily converted into omega-haloalkanols under traditional hydrogenation methods.

124 Claims, 40 Drawing Sheets

OTHER PUBLICATIONS

O'Leary,D.J. et al., *Tetrahedron Letters* (1998), 39, 7427, "A New Method for Cross–Metathesis of Terminal Olefins".

Scholl et al., *Organic Letters* (1999) 1, 953–956, "Synthesis and Activity of a New Generation of Ruthenium–Based Olefin Metathesis Catalysts Coordinated with 1,3–Dimesityl–4,5–dihydro–imidazol–2–ylidene Ligands".

ApSimon, John, editor, "The Synthesis of Insect Pheromones, 1979–1989," *The Total Synthesis of Natural Products*, (John Wiley & Sons, 1992), pp. 252–265.

Blackwell, Helen E., et al., "New Approaches to Olefin Cross–Metathesis," 122 J. Am. Chem. Soc. (2000), pp. 58–71.

Brandsma, Lambert, *Preparative Acetylenic Chemistry*, 2nd ed. (Elsevier Science Publishers, 1988) pp. 176–177.

ISOM 1999 International Symposium Olefin Metathesis and Related Chemistry: Catalytic Processes for the Next Millenium, Jul. 11–15, 1999, The Netherlands, <http://web.mit.edu/rrs/isom/level2/contact.htm> (9 pages).

Laurence, Brian R., et al. "*erythro*–6–Acetoxy–5–hexadecanolide, the Major Component of a Mosquito Oviposition Attractant Pheromone," 1 J. Chem. Soc. (Jan. 1, 1982), pp. 59–60.

Maynard, Heather D., et al. "Purification Technique for the Removal of Ruthenium from Olefin Metathesis Reaction Products," 40 Tetrahedron Letters (1999), pp. 4137–4140.

Olagbemiro, Timothy O., et al., "Production of (5R, 6S)–6–Acetoxy–5–hexadecanolide, the Mosquito Oviposition Pheromone, from the Seed Oil of the Summer Cypress Plant, *Kochia scoparia* (Chenopodiaceae)," 47 J. Agric. Food Chem. (1999), pp. 3411–3415.

Schwab, Peter, et al., "Synthesis and Applications of $RuCl_2$ (=CHR'))($PR_3$)$_2$: The Influence of the Alkylidene Moiety on Metathesis Activity," 118 J. Am. Chem Soc. (1996), pp. 100–110.

Shani, Arnon, "Integrated Pest Management Using Pheromones," 28 Chemtech 3 (Mar. 1998), pp. 30–35.

Coutrot, Ph., et al., "5–Formly–δ–Valerolactone: A Useful Synthon for the Chiral Synthesis of the *Vespa Orientalis* Pheromone and the Mosquito Oviposition Attractant Pheromone," 35 Tetrahedron Letters 45 (1994), pp. 8381–8384.

Gravier–Pelletier, Christine, et al., "Enantiopure Hydroxylactones from L–Ascorbic and D–Isoascorbic Acids. Part II. Synthesis of (–)–(5R, 6S)–6–Acetoxy–5–Hexadecanolide and its Diastereomers," 51 Tetrahedron 6 (1995), pp. 1663–1674.

Henrick, Clive A., "The Synthesis of Insect Sex Pheromones," 33 Tetrahedron 34, pp. 1845–1889.

Howse, P.E., et al., *Insect Pheromones and their Use in Pest Managenent* (Chapman & Hall, 1988).

Dawson, G.W., et al., "Convenient Synthesis of Mosquito Oviposition Pheromone and a Highly Flourinated Analog Retaining Biological Activity," 16 J. Chem. Ecology 6 (1990), pp. 1779–1789.

Harris, M.K., et al., "Pecan Nut Casebearer (Lepidoptera: Pyralidae) Sex Pheromone Used to Monitor Phenology and Estimate Effective Range of Traps," 90 J. Econ. Entomology (1997), pp. 983–987.

Henkel, B., et al., "Lipase–Catalyzed Synthesis of (5R, 6S)–6–Acetoxyylkan–5–olides–Homologues of the Mosquito Oviposition Attractant Pheromone," 339 J. Prakt. Chem. (1997), pp. 434–440.

Laurence, B.R., et al., "Absolute Configuration of Mosquito Oviposition Attractant Pheromone 6–acetoxy–5–hexadecanolide," 11 J. Chem. Ecology 5 (1985), pp. 643–648.

Laurence, B.R. and Pickett, J.A., "An Oviposition Attractant Pheromone in *Culex quinquefasciatus* Say (Diptera Culicidae)," 75 Bull. Entomology Res. (1985), pp. 283–290.

Millar, J.G., "Degradation and Stabilization of E8,E10–Dodecadienol, the Major Component of the Sex Pheromone of the Codling Moth (Lepidoptera, Tortricidae)," 88 J. Econ. Entomology 5 (Oct. 1995) pp. 1425–1432.

Millar, Jocelyn G., et al., "Sex Attractant Pheromone of the Pecan Nut Casebearer (Lepidoptera: Pyralidae)" 4 Bioorganic & Medicinal Chemisity 3 (1996), pp. 331–339.

Negishi, Ei–ichi, et al., "Stereoselective Synthesis of Conjugated trans–Enynes Readily Convertible into Conjugated cis,trans–Dienes and its Application to the Synthesis of the Pheromone Bombykol," J.C.S. Chem. Comm. (1973), pp. 874–875.

Otieno, W.A., et al., "A Field Trial of the Synthetic Oviposition Pheromone with *Culex quinquefasciatus Say* (Diptera, Culicidae) in Kenya," 78 Bull. Entomology Res. (1988), pp. 463–478.

Alexakis, A., et al., "Z–1–Iodohexene," *Organic Syntheses Collective* vol. 7 (John Wiley & Sons, Inc., 1990), pp. 290–294.

Bach, R.D., and Knight, J.W., "Epoxidation of Olefins by Hydrogen Peroxide–Acetonitrile: cis–Cyclooctene Oxide," *Organic Syntheses Collective* vol. 7 (John Wiley & Sons, Inc., 1990), pp. 126–128.

Ruhoff, John R., "n–Heptanoic Acid," *Organic Syntheses Collective* vol. 2 (John Wiley & Sons, Inc., 1943), pp. 315–316.

Witzemann, E.J., et al., "dl–Glyceraldehyde Ethyle Acetal," *Organic Syntheses Collective* vol. 2 (John Wiley & Sons, Inc., 1943), pp. 307–309.

"Production By the U.S. Chemical Industry," C&EN (Jul. 4, 1994), p. 36.

IPM Technologies, Inc., "High Quality Traps and Lures for Insect Monitoring and Control," <http://www.ipmtech.com> (4 pages).

Trécé Incorporated, "Pherocon Insect Monitoring Systems Catalog," <http://www.trece.com/phercat.html> (12 pages).

Mori, Kenji, "Synthesis of Optically Active Pheromones," 45 Tetrahedron Report 11 (1989), pp. 3233–3298.

Svirskaya, P.I., et al., "Syntheses of Pure (9Z,11Z), (9E, 11E), (9E, 11Z). and (9Z, 11E)–9, 11—Hexadecadienals—Possible Candidate Pheromones," 10 *Journal of Chemical Ecology* 5 (1984), pp. 795–807.

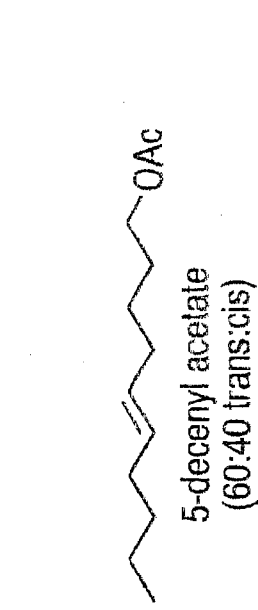
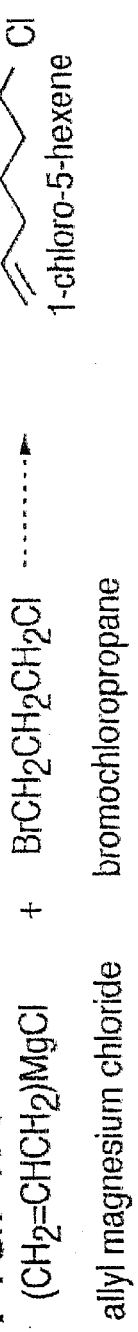
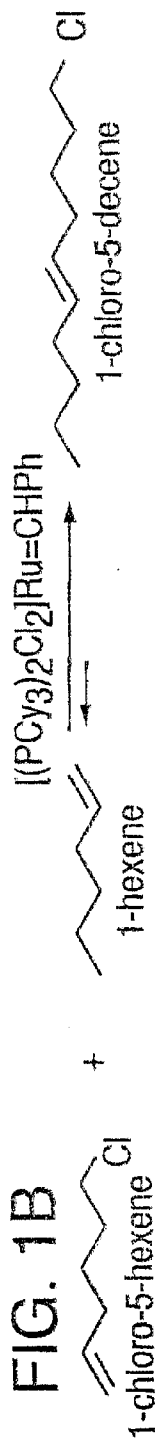
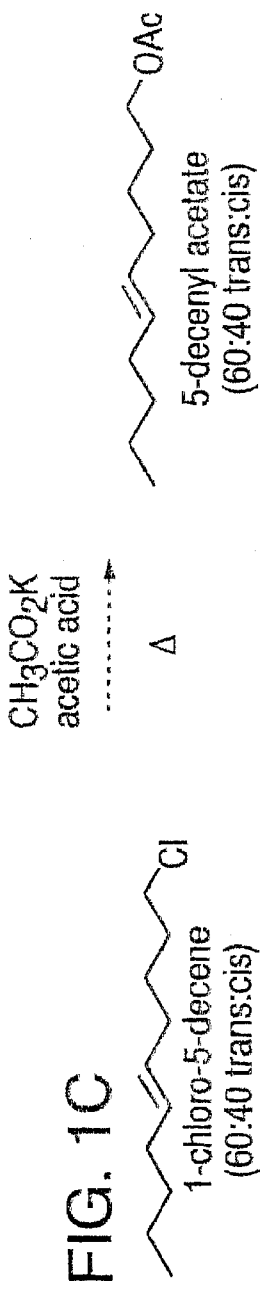
FIG. 1A
$(CH_2=CHCH_2)MgCl$ + $BrCH_2CH_2CH_2Cl$ → 1-chloro-5-hexene
allyl magnesium chloride     bromochloropropane
FIG. 1B
1-chloro-5-hexene + 1-hexene ⇌ [(PCy$_3$)$_2$Cl$_2$]Ru=CHPh → 1-chloro-5-decene
FIG. 1C
1-chloro-5-decene (60:40 trans:cis) --CH$_3$CO$_2$K, acetic acid, Δ--> 5-decenyl acetate (60:40 trans:cis)
FIG. 1D
5-decenyl acetate (60:40 trans:cis) --sodium salt of benzenesulfinic acid, CH$_3$CO$_2$H--> 5-decenyl acetate (80:20 trans:cis)

FIG. 2  Class I Catalysts
LL'AA'M=CR_bR_c is more specifically
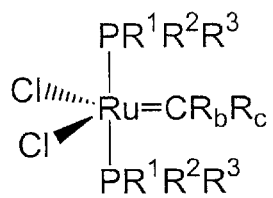
FIG. 3  Class II Catalysts
R" is substituted aryl
X are halogens or heteroatoms
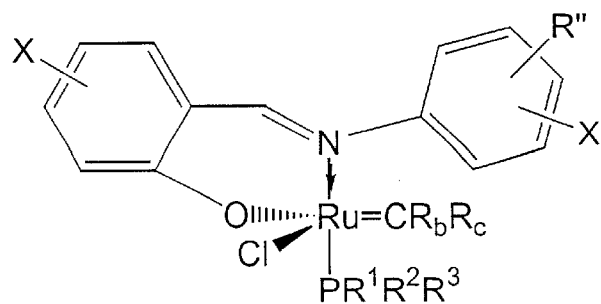
FIG. 4  Class III Catalysts
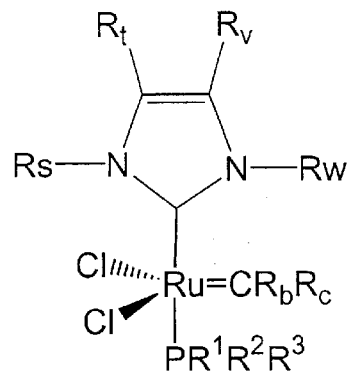
FIG. 5  Class IV Catalysts
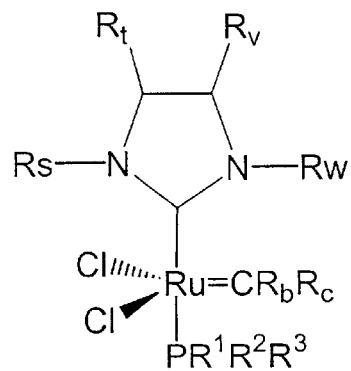

823

739

801

716

849

765

791

707

815

731

834

751

FIG. 2M
Ruthenium Catalyst Table I

| FIG. # | Molecular Weight | CAS # | Catalyst Name |
|---|---|---|---|
| 2A | 822.95 | 172222-30-9 | Ruthenium, dichloro(phenylmethylene)bis(tricyclohexylphosphine) |
| 2B | 738.80 | | Ruthenium, dichloro(phenylmethylene)bis(tricyclopentylphosphine) |
| 2C | 800.95 | 194659-03-9 | Ruthenium, dichloro(3-methyl-2-butenylidene)bis(tricyclohexylphosphine) |
| 2D | 716.79 | 220883-08-9 | Ruthenium, dichloro(3-methyl-2-butenylidene)bis(tricyclopentylphosphine) |
| 2E | 848.99 | | Ruthenium, dichloro(3-phenyl-2-propenylidene)bis(tricyclohexylphosphine) |
| 2F | 764.83 | | Ruthenium, dichloro(3-phenyl-2-propenylidene)bis(tricyclopentylphosphine) |
| 2G | 790.91 | | Ruthenium, dichloro(ethoxymethylene)bis(tricyclohexylphosphine) |
| 2H | 706.75 | | Ruthenium, dichloro(ethoxymethylene)bis(tricyclopentylphosphine) |
| 2I | 814.98 | | Ruthenium, dichloro(t-butylvinylidene)bis(tricyclohexylphosphine) |
| 2J | 730.82 | | Ruthenium, dichloro(t-butylvinylidene)bis(tricyclopentylphosphine) |
| 2K | 834.97 | | Ruthenium, dichloro(phenylvinylidene)bis(tricyclohexylphosphine) |
| 2L | 750.81 | | Ruthenium, dichloro(phenylvinylidene)bis(tricyclopentylphosphine) |

877

835

855

813

903

881

FIG. 3G
Ruthenium Catalyst Table II

| 3A | 877.45 | 211686-96-3 | Ruthenium, [2-(((2,6-bismethylethyl)-4-nitrophenyl)imino-kN)methyl-4-nitrophenolato-kO)]chloro-(phenylmethylene)(tricyclohexylphosphine) |
|---|---|---|---|
| 3B | 835.37 | | Ruthenium, [2-(((2,6-bismethylethyl)-4-nitrophenyl)imino-kN)methyl-4-nitrophenolato-kO)]chloro-(phenylmethylene)(tricyclopentylphosphine) |
| 3C | 855.45 | | Ruthenium, [2-(((2,6-bismethylethyl)-4-nitrophenyl)imino-kN)methyl-4-nitrophenolato-kO)]chloro-(3-methyl-2-butenylidene)-(tricyclohexylphosphine) |
| 3D | 813.37 | | Ruthenium, [2-(((2,6-bismethylethyl)-4-nitrophenyl)imino-kN)methyl-4-nitrophenolato-kO)]chloro-(3-methyl-2-butenylidene)-(tricyclopentylphosphine) |
| 3E | 903.47 | | Ruthenium, [1,3-bis-(2,4,6-trimethylphenyl)-2-imidazolidinylidene][2-(((2,6-bismethylethyl)-4-nitrophenyl)imino-kN)methyl-4-nitrophenolato-kO)]-chloro-(phenylmethylene) |
| 3F | 881.46 | | Ruthenium, [1,3-bis-(2,4,6-trimethylphenyl)-2-imidazolidinylidene][2-(((2,6-bismethylethyl)-4-nitrophenyl)imino-kN)methyl-4-nitrophenolato-kO)]-chloro-(3-methyl-2-butenylidene) |

846

805

824

783

873

831

814

773

839

797

859

817

FIG. 4M
Ruthenium Catalyst Table III

| FIG. # | Molecular Weight | CAS # | Catalyst Name |
|---|---|---|---|
| 4A | 846.96 | 223415-64-3 or 223415-66-5 | Ruthenium, dichloro [1,3-dihydro-1,3-bis-(2,4,6-trimethylphenyl)-2H-imidazol-2-ylidene](phenylmethylene)(tricyclohexylphosphine) |
| 4B | 804.88 | | Ruthenium, dichloro [1,3-dihydro-1,3-bis-(2,4,6-trimethylphenyl)-2H-imidazol-2-ylidene](phenylmethylene)(tricyclopentylphosphine) |
| 4C | 824.95 | 261788-40-3 | Ruthenium, dichloro [1,3-dihydro-1,3-bis-(2,4,6-trimethylphenyl)-2H-imidazol-2-ylidene](3-methyl-2-butenylidene)(tricyclohexylphosphine) |
| 4D | 782.87 | 253873-32-4 | Ruthenium, dichloro [1,3-dihydro-1,3-bis-(2,4,6-trimethylphenyl)-2H-imidazol-2-ylidene](3-methyl-2-butenylidene)(tricyclopentylphosphine) |
| 4E | 872.99 | | Ruthenium, dichloro [1,3-dihydro-1,3-bis-(2,4,6-trimethylphenyl)-2H-imidazol-2-ylidene](3-phenyl-2-propenylidene)(tricyclohexylphosphine) |
| 4F | 830.91 | | Ruthenium, dichloro [1,3-dihydro-1,3-bis-(2,4,6-trimethylphenyl)-2H-imidazol-2-ylidene](3-phenyl-2-propenylidene)(tricyclopentylphosphine) |
| 4G | 814.91 | | Ruthenium, dichloro [1,3-dihydro-1,3-bis-(2,4,6-trimethylphenyl)-2H-imidazol-2-ylidene](ethoxymethylene)(tricyclohexylphosphine) |
| 4H | 772.83 | | Ruthenium, dichloro [1,3-dihydro-1,3-bis-(2,4,6-trimethylphenyl)-2H-imidazol-2-ylidene](ethoxymethylene)(tricyclopentylphosphine) |
| 4I | 838.98 | | Ruthenium, dichloro [1,3-dihydro-1,3-bis-(2,4,6-trimethylphenyl)-2H-imidazol-2-ylidene](t-butylvinylidene)(tricyclohexylphosphine) |
| 4J | 796.90 | | Ruthenium, dichloro [1,3-dihydro-1,3-bis-(2,4,6-trimethylphenyl)-2H-imidazol-2-ylidene](t-butylvinylidene)(tricyclopentylphosphine) |
| 4K | 858.97 | | Ruthenium, dichloro [1,3-dihydro-1,3-bis-(2,4,6-trimethylphenyl)-2H-imidazol-2-ylidene](phenylvinylidene)(tricyclohexylphosphine) |
| 4L | 816.89 | | Ruthenium, dichloro [1,3-dihydro-1,3-bis-(2,4,6-trimethylphenyl)-2H-imidazol-2-ylidene](phenylvinylidene)(tricyclopentylphosphine) |

848

807

826

785

875

833

816

775

841

799

861

819

FIG. 5M
Ruthenium Catalyst Table IV

| FIG. # | Molecular Weight | CAS # | Catalyst Name |
|---|---|---|---|
| 5A | 848.97 | 246047-72-3 | Ruthenium, [1,3-bis-(2,4,6-trimethylphenyl)-2-imidazolidinylidene]-dichloro(phenylmethylene)(tricyclohexylphosphine) |
| 5B | 806.89 | | Ruthenium, [1,3-bis-(2,4,6-trimethylphenyl)-2-imidazolidinylidene]-dichloro(phenylmethylene)(tricyclopentylphosphine) |
| 5C | 826.97 | 253688-91-4 | Ruthenium, dichloro [1,3-bis-(2,4,6-trimethylphenyl)-2-imidazolidinylidene](3-methyl-2-butenylidene)(tricyclohexylphosphine) |
| 5D | 784.89 | | Ruthenium, dichloro [1,3-bis-(2,4,6-trimethylphenyl)-2-imidazolidinylidene](3-methyl-2-butenylidene)(tricyclopentylphosphine) |
| 5E | 875.01 | | Ruthenium, dichloro [1,3-bis-(2,4,6-trimethylphenyl)-2-imidazolidinylidene](3-phenyl-2-propenylidene)(tricyclohexylphosphine) |
| 5F | 832.93 | | Ruthenium, dichloro [1,3-bis-(2,4,6-trimethylphenyl)-2-imidazolidinylidene](3-phenyl-2-propenylidene)(tricyclopentylphosphine) |
| 5G | 816.93 | | Ruthenium, [1,3-bis-(2,4,6-trimethylphenyl)-2-imidazolidinylidene]-dichloro(ethoxymethylene)(tricyclohexylphosphine) |
| 5H | 774.85 | | Ruthenium, [1,3-bis-(2,4,6-trimethylphenyl)-2-imidazolidinylidene]-dichloro(ethoxymethylene)(tricyclopentylphosphine) |
| 5I | 840.99 | | Ruthenium, dichloro [1,3-bis-(2,4,6-trimethylphenyl)-2-imidazolidinylidene](t-butylvinylidene)(tricyclohexylphosphine) |
| 5J | 798.91 | | Ruthenium, dichloro [1,3-bis-(2,4,6-trimethylphenyl)-2-imidazolidinylidene](t-butylvinylidene)(tricyclopentylphosphine) |
| 5K | 860.98 | | Ruthenium, dichloro [1,3-bis-(2,4,6-trimethylphenyl)-2-imidazolidinylidene](phenylvinylidene)(tricyclohexylphosphine) |
| 5L | 818.90 | | Ruthenium, dichloro [1,3-bis-(2,4,6-trimethylphenyl)-2-imidazolidinylidene](phenylvinylidene)(tricyclopentylphosphine) |

FIG. 6
Synthesis of Halo-Alkenols and Halo-Alkanes by Cross-Metathesis Reactions
A) 
B) 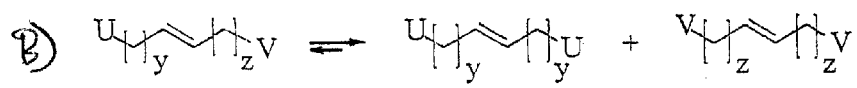
C) 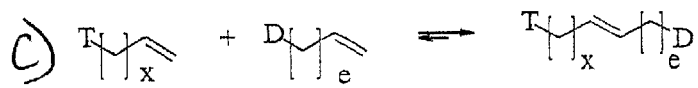
D) 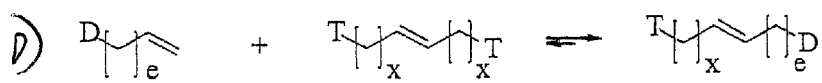
E) 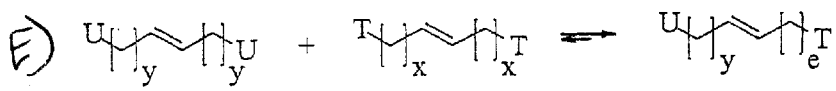
x = 0 to 10
e = 0 to 10
y = 0 to 10
z = 0 to 10
T, U, V and D are chosen from the group of: hydrogen, alkyl, aryl, hydroxy, acetyl, protected alcohol, halide, mesylate, tosylate, etc......
Where protected alcohol includes tetrahydropyran, ethyl vinyl ether, trisubstituted silyl, t-butyl, ester or ether groups .......
F) 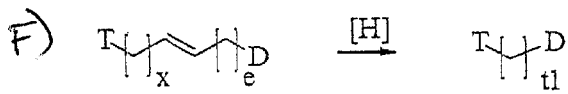
G) 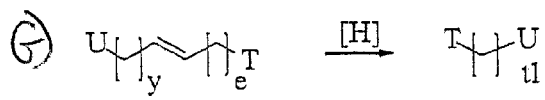
t1 = 2 to 22

FIG. 7
Table V

| Alpha-Olefin | Cross-Metathesis Product | Abbreviated Cross-Metathesis Name |
|---|---|---|
| Allyl chloride | 1,4-dichloro-2-butene | $2C_4Cl_2$ |
|  | 1,4-diacetoxy-2-butene | $2C_4OAc_2$ (commercially available) |
| Chlorobutene | 1,6-dichloro-3-hexene | $3C_6Cl_2$ |
| Butenyl acetate | 1,6-diacetoxy-3-hexene | $3C_6OAc_2$ |
| Chloropentene | 1,8-dichloro-4-octene | $4C_8Cl_2$ |
| Pentenyl acetate | 1,8-diacetoxy-4-octene | $4C_8OAc_2$ |
| Clorohexene | 1,10-dichloro-5-decene | $5C_{10}Cl_2$ |
| Hexenyl acetate | 1,10-diacetoxy-5-decene | $5C_{10}OAc_2$ |

FIG. 8
Table VI

| Halo Starting Material | Acetoxy Starting Material | Cross Olefin | Hydrogenated Product |
|---|---|---|---|
| $2C_4Cl_2$ | $2C_4OAc_2$ | $AcO(2C_4)Cl$ | $AcO(C_4)Cl$ |
| $2C_4Cl_2$ | $3C_6OAc_2$ | $AcO(2C_5)Cl$ | $AcO(C_5)Cl$ |
| $2C_4Cl_2$ | $4C_8OAc_2$ | $AcO(2C_6)Cl$ | $AcO(C_6)Cl$ |
| $2C_4Cl_2$ | $5C_{10}OAc_2$ | $AcO(2C_7)Cl$ | $AcO(C_7)Cl$ |
| $3C_6Cl_2$ | $3C_6OAc_2$ | $AcO(3C_6)Cl$ | $AcO(C_6)Cl$ |
| $3C_6Cl_2$ | $4C_8OAc_2$ | $AcO(3C_7)Cl$ | $AcO(C_7)Cl$ |
| $3C_6Cl_2$ | $5C_{10}OAc_2$ | $AcO(3C_8)Cl$ | $AcO(C_8)Cl$ |
| $4C_8Cl_2$ | $4C_8OAc_2$ | $AcO(4C_8)Cl$ | $AcO(C_8)Cl$ |
| $4C_8Cl_2$ | $5C_{10}OAc_2$ | $AcO(4C_9)Cl$ | $AcO(C_9)Cl$ |
| $5C_{10}Cl_2$ | $5C_{10}OAc_2$ | $AcO(5C_{10})Cl$ | $AcO(C_{10})Cl$ |

Synthesis of 5-Decenyl Acetate:
Major Component of the Peach Twig Borer Pheromone Synthesis of 5-Decenyl Acetate:
Major Component of the Peach Twig Borer Pheromone Synthesis of 5-Decenyl Acetate:
Major Component of the Peach Twig Borer Pheromone E-5-Decenyl Acetate Synthesis using Vinyl Borate E-5-Decenyl Acetate Synthesis using Vinyl Borate, High Trans Isomer Route Synthesis of 9-Tetradecenyl Formate:
Pheromone Analog of the Diamondback Moth (DBM)

Synthesis of 11-Tetradecenyl Acetate:
Pheromone of the Omnivorous Leafroller(OLR)

FIG. 20
Synthetic Route to E:Z-11-Tetradecenyl acetate:
Omnivorous Leafroller Moth (OLR) Pheromone
Jojoba Oil (58% of Jojoba Oil
is Z-11-eicosenol/acid ester)
1) LiAlH$_4$
2) Acetylation
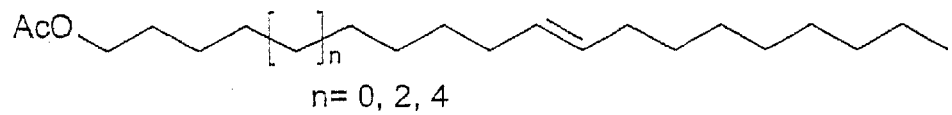
n = 0, 2, 4
n = 0  6%
　　2 58%
　　4 30%　　　Vacuum distillation
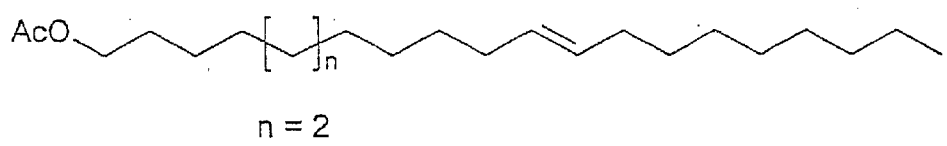
n = 2
1) metathesis, 3-hexene
2) vacuum distillation
OLR Pheromone
80:20 ratio E:Z-11-Tetradecenyl acetate Synthesis of E-4-Tridecenyl Acetate:
Major Component of the Tomato Pinworm (TPW) Pheromone Synthesis of E.E.-8, 10-Dodecadienol
Codling Moth (CM) Pheromone Synthesis of TPW Pheromone by Cross-Metathesis of
1, 8-Diacetoxy-4-Octene and 9-Octadecene met cat = catalyst 823, 801, 848

Synthesis of 8, 10-Dodecadienol from 8-Chlorooctanyl Acetate and Crotonaldehyde

Meadowfoam oil

Synthesis of 11-Docosene

Improved-Proposed Route to E9, Z11-Hexadecadienal:
Pecan Nut Casebearer (PNCB) Pheromone E9, Z11-Hexadecadienal
Pecan Nut Casebearer (PNCB) pheromone

US 6,696,597 B2

METATHESIS SYNTHESES OF PHEROMONES OR THEIR COMPONENTS

This application derives priority from International Application No. PCT/US00/31549, filed Nov. 17, 2000, which derives priority from U.S. Provisional Patent Application No. 60/166,543, filed Nov. 18, 1999, and this application is a continuation-in-part of U.S. patent application Ser. No. 09/387,486, filed Sep. 1, 1999, which is now U.S. Pat. No. 6,215,019, which derives priority from U.S. Provisional Patent Application No. 60/098,792, filed Sep. 1, 1998.

TECHNICAL FIELD

The present invention relates to synthetic pheromones or their components and, in particular, to metathesis reactions to produce biologically active compounds and intermediates such as insect sex-attractant pheromones or their components such as E-5-decenyl acetate, the major component of the Peach twig borer pheromone; (5R,6S)-6-acetoxy-5-hexadecanolide, the mosquito oviposition sex attractant pheromone; or E9,Z11-hexadecadienal, the pecan nut casebearer moth pheromone.

BACKGROUND OF THE INVENTION

Insect pests destroy crops and/or spread disease. Common pest control methods involves spraying farmland, orchards, wetlands, forests, or other pest habitats with insecticides. This method is problematic because insecticides are applied directly to crops or watersheds, and this practice is contrary to an increasing preference for organic produce as well as contrary to water quality issues and other environmental concerns. Insecticides are also nondiscriminate killers and kill beneficial insects as well as harmful insects. Finally, the insect pests are becoming increasingly resistant to many of the common insecticides.

An alternative method to control insect populations involves the use of the insect's sex attractant to confuse the male insect and thereby prevent mating and eliminate future insect generations. This technique is called mating pattern disruption. Insect pheromones constitute a relatively new class of compounds that have a number of advantages over conventional insecticides. Insect pheromones are nontoxic and environmentally friendly. They are specific to the target insect and do not adversely affect beneficial insects and, they have not been shown to induce the development of resistance in the target insects. The biggest drawbacks in using mating pattern disruption to control insect populations is the cost of producing the insect pheromone, which is typically far more expensive than that of traditional insecticides. Methods that reduce the production costs of insect pheromones would make mating pattern disruption an economical technique for controlling insect populations and thereby minimize environmental concerns associated with pest control.

In general, common pheromones include a 10- to 18-carbon atom-containing olefin that has a terminal alcohol, aldehyde, or acetate functional group and possess a particular stereo-isomerism. The following background is presented herein only by way of example to a few pheromones for common insect pests, such as the Peach Twig Borer (PTB), which is a major pest in stone fruit orchards, and for pathogen-vectoring mosquitoes of genus Culex, and for the Pecan nutcase bearer.moth, which is a major pest in pecans.

PTB pheromone is an 85:15 ratio of E-5-decenyl acetate and E-5-decenol. Thus production of 5-decenyl acetate, which is the major component of PTB pheromone, is a significant step of the PTB pheromone manufacturing process. The acetate can be subsequently removed by hydrolysis to obtain E-5-decenol, the other component of PTB pheromone. A fast, inexpensive, and high yield process for synthesizing E-5-decenyl acetate is, therefore, desirable.

The following background information concerning the Mosquito Oviposition Pheromone (MOP), another highly sought after insect pest pheromone, is largely derived from Olagbemiro, et al. in "Production of (5R,6S)-6-Acetoxy-5-hexadecanolide, the Mosquito Oviposition Pheromone, from Seed Oil of the Summer Cypress Plant, *Kochia scoparia* (Chenopodiaceae)," *J. Agric. Food Chem.* (1999) 47, 3411. Please refer to this article for greater detail.

Mosquitoes of the genus Culex (Diptera: Culicidae) pose the greatest threat to public health because of their ability to act as vectors of causative agents for diseases such as malaria, dengue, yellow fever, encephalitis, and filariasis, which afflict many millions of people world-wide. Malaria and encephalitis infect the greatest number of people and have the highest mortality levels, affecting approximately one-third the world's 1.5 billion people in 90 countries, mainly in Africa. (AAAS (American Association for the Advancement of Science) "Malaria and Development in Africa": *AAAS*: Washington, D.C., (1991); Giles et al. "Bruce-Chwatt's Essential Malariology", 3rd Ed.; Edward Arnold; London UK (1993); and WHO/CTD. "Malaria Prevention and Control," WHO Report; Geneva (1998).)

Filariasis has infected 3.33% (i.e. ~15 million people) of the 450 million people at risk, with nearly 1 million new cases occurring annually. (Reeves et al. "Natural Infection in Arthropod Vector," *Epidemiology and Control of Mosquito-Borne Arboviruses in California* 1943–1987; Reeves, W. G., Ed.; California Mosquito Control Association: Sacramento, Calif. 1990; pp 128–149.) Because of the rapid increase in reported cases of vector caused diseases, efficient techniques for vector surveillance and control are of the utmost importance.

The mosquitoes of *Culex quinquefasciatus* are responsible for the transmission of *Wuchereria bancrofti*, the causative agent of human filariasis and St. Louis encephalitis virus and other arboviruses in the United States. (Reisen et al. "Ecology of mosquito and St. Louis Encephalitis virus in Los Angeles basin of California, 1987–1990," *J. Med. Entomol.* (1992) 29, 582.) Gravid *Culex quinquefasciatus* females use olfactory cues to locate suitable egg-laying sites. The main cue is the oviposition attractant pheromone ((5R,6S)-6-acetoxy-5-hexadecanolide) which is released by mature egg rafts. (Osgood, C. E. "An oviposition pheromone associated with the egg rafts of *Culex tarsalis*," *J. Econ. Entomol.* (1971) 64, 1038; Osgood et al. "An Air-Flow Olfactometer for the Distinguishing between Oviposition Attractants and Stimulants of Mosquitoes," *J. Econ. Entomol.* (1971a) 64, 1109; and Starratt, A. N.; C. E. Osgood "1,3-Diglycerides from the Eggs of *Culex pipens quinquefasciatus* and *Culex pipens pipens*," *Comp. Biochem. Physiol.* (1973) 857.)

The oviposition attractant pheromone ((5R,6S)-6-acetoxy-5-hexadecanolide) produced by female mosquitoes of *Culex quinquefasciatus* is released from apical droplets on the eggs. (Laurence et al. "Erythro-6-acetoxy-5-hexadecanolide the major component of a mosquito oviposition attractant pheromone," *J. Chem. Soc. Chem. Commun.* (1982) 59–60. (Laurence et al. '82) This attracts other females of this and related species to the vicinity of the laid eggs. (Howse et al. "Insect Pheromones and their Use in Pest Management" Chapman and Hall, 2-6 Boundary Row, London SE1 8HN, UK 1998, p 52.)

New strategies for controlling mosquitoes of *Culex quinquefasciatus* started with the identification of the oviposition attractant pheromone (5R,6S)-6-acetoxy-5-hexadecanolide. (Laurence et al. '82; Laurence et al. "Absolute Configuration of the Mosquito Oviposition Attractant Pheromone 6-acetoxy-5-hexadecanolide," *J. Chem. Ecol.* (1985) 11,643; and Laurence et al. "An Oviposition Attractant Pheromone in *Culex quinquefasciatus* Say (Diptera, Culicidae)," *Bull. Entomol. Res.* (1985a) 75,283.) Laboratory and field trials, in nine countries and three continents, using synthetic pheromone containing an equal ratio of all four stereoisomers [i.e., (5R,6S), (5S,6S), (5R,6R) and (5S, 6R)] of (5,6)-6-acetoxy-5-hexadecanolide (Dawson et al. "Convenient Synthesis of Mosquito Oviposition Pheromone and a Highly Flourinated Analog Retaining Biological Activity," *J. Chem. Ecol.* (1990) 16, 1779.) have demonstrated the efficacy of the oviposition pheromone in attracting Culex spp. mosquitoes. (Otieno et al. "A Field Trial of the Synthetic Oviposition Pheromone with *Culex quinquefasciatus* Say (Diptera, Culicidae) in Kenya," *Bull. Entoniol. Res.* (1988) 78, 463.) Despite the presence of the three inactive and unnatural stereoisomers of (5, 6)-6-acetoxy-5-hexadecanolide [i.e., (5S,6S), (5R,6R) and (5S,6R)], the biological activity of the naturally occurring isomer was unaffected. These results demonstrate that an effective, efficacious and inexpensive oviposition attractant pheromone, (5R,6S)-6-acetoxy-5-hexadecanolide, would result from a racemic mixture of (5R,6S)-6-acetoxy-5-hexadecanolide containing its stereoisomers. Also Olagbemiro et al. demonstrated that *Culex quinquefasciatus* female mosquitoes are unaffected by seed oil impurities and synthetic impurities produced from the synthesis of (5R,6S)-6-acetoxy-5-hexadecanolide and its stereoisomers.

The identification and characterization of the oviposition attractant pheromone provided the impetus for many asymmetric syntheses and large scale racemic synthetic routes. (Laurence et al. '82; Coutrout et al. "5-Formyl-d-valerolactone—A Useful Synthon for the Chiral Synthesis of the *Vespa orientalis* Pheromone and the Mosquito Oviposition Attractant Pheromone," *Tetrahedron Lett.* (1994) 35, 8381; Gravierpelletier et al. "Enantiopure hydroxylactones from L-ascorbic acid and D-isoascorbic acids: 2. Synthesis of (−)-(5R,6S)-6-acetoxy-5-hexadecanolide and its Diastereomers," *Tetrahedron* (1995) 51, 1663; Henkel et al. "Lipase catalyzed Synthesis of (5R,6S)-6-acetoxyylkan-5-olides-Homologues of the Mosquito Oviposition Attractant Pheromone," *J. Pract. Chem.* (1997) 339, 434–440; Mori, K., "The Total Synthesis of Natural Products, Volume 9" John ApSimon Ed. John Wiley & Sons New York (1992) pp. 252–264, and references therein.) The various synthetic routes cited above can provide multigram quantities of oviposition attractant pheromone, however, the cost of producing them are prohibitive. Therefore, an inexpensive and effective Culex mosquito oviposition pheromone and a synthesis thereof would be greatly desirable.

Another insect pest, the pecan nut casebearer moth (PNCB), *Acrobasis nuxvorella* Neuzig, is one of the last major pests of the $49 million United States pecan industry that is not controlled by biological means. The PNCB is the key pest of pecans in Texas, Oklahoma, Missouri, Kansas, Arkansas and Louisiana, and it can also impacts crops further east. This pest recently invaded the highly productive pecan Mesilla Valley region of New Mexico. Management of pecan orchards in the west is nearly completely organic, disturbed only by the use of insecticides to control the pecan nut casebearer moth.

The currently effective organophosphate insecticides (i.e. Lorsban E4 and 50W) are under review by EPA through the Food Quality Protection Act and may be removed from the market because of residuals in food products. Pyrethroid insecticides are not a viable alternative because they cause a population explosion of aphids and spider mites after treatment, which are difficult to control in pecans (Knutson A.; W. Ree. 1998. "Managing insect and mite pests of commercial pecan in Texas," *Texas Ag Extension Service*, B 1238. 13 pp). Soon, pecan growers may not have a viable alternative to control the PNCB. CONFIRM®, an insect growth regulator, is an alternative, but it is expensive and is subject to development of resistance to it when it is the sole method of control employed. If left unchecked, the PNCB could devastate the pecan industry and cause many pecan growers to go out of business. Thus, there is an immediate need to develop a viable and economical alternative to controlling the PNCB.

PNCBs are most damaging during their first generation which occurs during two weeks in late April and early May of mating and egg laying (Knutson, 1988). This treatment window provides a brief and defined period of time when insecticide sprays are capable of controlling PNCB populations by targeting the larvae that hatch before they penetrate nutlets. The recent development of pheromone traps to monitor PNCB population dynamics has transformed the management of pecan orchards, allowing for the accurate timing of insecticide applications. A promising alternative pest management technique is to use the PNCB pheromone to promote mating disruption and thereby controlling its populations.

The PNCB pheromone is E9,Z11-hexadecadienal, a unique pheromone compound. The PNCB pheromone is not commercially available in quantities larger than micrograms. The two companies that sell lures, for monitoring the PNCB are unable to supply the PNCB pheromone in quantities greater than a gram. Because there is not a bulk commercial source (i.e. >20 g) of this pheromone available, there is a need to develop a large scale procedure for the PNCB pheromone and to develop an insect-controlling technology to keep the PNCB in check.

A simple method of synthesizing a wide variety of pheromone compounds and precursors that produces high yields and that can be capable of producing stable and reproducible stereoisomeric ratios of products, if needed, is therefore desirable.

SUMMARY OF THE INVENTION

An object of the present invention is to provide a synthesis for pheromones or their components that employs a metathesis reaction.

Another object of the invention is, therefore, to improve the process for manufacturing peach twig borer pheromone.

A further object of the present invention is to provide an improved synthesis of mosquito oviposition attractant pheromone.

Yet another object of the present invention is to provide an improved synthesis of pecan nutcase bearer pheromone.

Still another object of the present invention is to provide an improved synthesis of omega haloalkanols and omega haloalkanyl acetates.

FIGS. 1A, 1B, 1C, and 1D (collectively FIG. 1) depict a recent method of producing 5-decenyl acetate disclosed in U.S. Pat. No. 5,916,983 of Pederson and Grubbs. The synthesis produces 1-chlorohexene by coupling allyl magnesium chloride and bromochloropropane. A 40 percent yield of a 60:40 isomeric ratio of trans:cis 1-chloro-5-decene is then obtained by olefin metathesis of 1-chlorohexene and 1-hexene. The metathesis catalyst used in this process is bis(tricyclohexylphosphine)dichloro ruthenium (II) benzylidene, [(PCy$_3$)$_2$Cl$_2$]Ru=CHPh, herein referred to as Catalyst 823, shown in FIG. 2A.

These reactions are performed between 32° C. and 62° C.; at room temperature, the reaction is slow and conversions are lower. A 27 percent yield is obtained when the reaction is run at 32°. 1-Chloro-5-decene is converted to 5-decenyl acetate by heating the former with potassium acetate in acetic acid. The resulting 60:40 ratio of trans:cis 5-decenyl acetate is isomerized to an 80:20 ratio of trans:cis 5-decenyl acetate by the sodium salt of benzenesulfinic acid in acetic acid.

The low 25 to 27 percent gross yield of 5-decenyl acetate is largely due to the formation of a methylidene ruthenium catalyst intermediate, which is a thermodynamically stable alkylidene that prevents high conversion of starting materials to products and prevents the formation of a high trans isomeric product.

This method typically requires 18 to 25 days to produce 12 Kg of 5-decenyl acetate in an 80:20 cis:trans ratio using standard-sized equipment (multiple reactions need to be run because of low yields and many of the reactions need to be diluted with solvents to work properly). In particular, five days are typically required to run the reaction and to work up and distill the 1-chloro-5-decene. Three metathesis runs at one day each, plus two days to remove the catalyst, and 2 days to distill, are typically needed to produce the 1-chloro-5-decene for a subtotal of seven days. The subsequent production of 5-decenyl acetate with a trans:cis ratio of 60:40 requires two to three runs at 36 to 48 hours each to achieve 98 percent conversion, for a subtotal of four to six days. Twenty-four hours for each of two batches are required to achieve the isomerization of 5-decenyl acetate to an 80:20 ratio of trans:cis, for a subtotal of two days. The total time of 18 to 25 days does not include the time for the final distillation.

Although the 20 percent cis-5-decenyl acetate does not affect the efficacy of the PTB pheromone in lures and mating disruption applications, the low yield and the long completion time make the process expensive. In view of the numerous reaction steps, the large amount of required starting materials and reagents, the long reaction times, and/or the overall low yield, this manufacturing process for 5-decenyl acetate is still not satisfactory.

The present invention relates, therefore, to metathesis syntheses for a variety of value-added products metathesis in an economical and efficient manner. Most of the cross-metathesis reactions are run neat, and the unreacted starting materials are recycled back into the next cross-metathesis reaction. The invention provides the ability to cross-metathesize two different or similar terminal olefins (i.e. alpha olefin) to produce a new internal olefin, the ability to cross metathesize a terminal olefin and an internal olefin to yield a new internal olefin, the ability to cross metathesize a terminal olefin and a cyclic olefin to yield a new terminal and/or internal olefin, and the ability to cross-metathesize two similar or different internal olefins to yield a new internal olefin product.

Some of the most notable metathesis products facilitated by the invention include insect sex-attractant pheromones or their components, such as E-5-decenyl acetate, the major component of the Peach Twig Borer pheromone; (5R,6S)-6-acetoxy-5-hexadecanolide, the oviposition attractant pheromone; E9,Z11-hexadecadienal, the pecan nut casebearer moth pheromone; 9-tetradecenyl formate, an analog of the Diamondback Moth (DBM) pheromone; 1-tetradecenyl acetate, the Omnivorous Leafroller (OLR) pheromone; E-4-tridecenyl acetate, the major component of the Tomato Pinworm (TPW) pheromone; E,E-8,10-dodecadienol, the Codling Moth (CM) pheromone. The syntheses preferably entail few reaction steps, use generally commercially available starting materials, and have relatively short process times. These syntheses produce good yields without the need for expensive or sophisticated equipment. The invention also provides an inexpensive route for producing omega-haloalkenols by cross-metathesizing alpha-omega-diacetoxy alkenes and alpha-omega-dihalides to yield omega-haloalkenols, which are easily converted into omega-haloalkanols under traditional hydrogenation methods.

The metathesis catalysts preferred for these reactions are selected from Class I–IV metathesis catalysts presented in FIGS. 2, 3, 4, or 5. More preferred metathesis catalysts are those presented in Tables I–IV. The most preferred embodiments employ Catalysts 848, 785, 807, 826, 823, and 801.

The invention particularly provides an improved synthesis of E-5-decenyl acetate that eliminates many of the problems associated with the previous method. In a preferred embodiment, the improvements include: 1) a technique to obtain higher conversion of starting materials to products (from 40 percent to greater than 75 percent); 2) an increase in the metathesis trans:cis ratio from 60:40 to between 80:20 to 84:16; 3) only two reaction steps; and 4) a production time of less than a week.

In one embodiment, certain of these improvements are accomplished by self-metathesizing 1-hexene to 5-decene followed by cross-metathesizing of 5-decene and 5-hexenyl acetate. Both reactions are performed in the presence of the same metathesis catalyst. The self-metathesis of 1-hexene is performed under vacuum so the ethylene side product is allowed to bubble out of solution. The elimination of 1-hexene prevents the formation of the methylidene catalyst intermediate and leads to an increased yield, greater than 98 percent pure 5-decenyl acetate with an 80:20 to 84:16 trans:cis ratio as compared to the earlier 60:40.

The present invention also provides a relatively inexpensive synthetic process for making mosquito oviposition attractant pheromone for the pathogen-vectoring mosquitoes of genus Culex, (5R,6S)-6-acetoxy-5-hexadecanolide. Preferred syntheses of mosquito oviposition attractant pheromone involve the cross-metathesis of commercially available materials, such as meadowfoam oil, hexenoic acid derivatives, hexenal derivatives, or hexenol derivatives with 1-dodecene or 11-docosene, followed by oxidation of the double bond and lactonization. In several embodiments, meadowfoam oil is a preferred starting material because 95% of the oil contains a Z-5-carboxylate moiety, it is commercially available, and it is readily converted to (5R,6S)-6-acetoxy-5-hexadecanolide through metathesis reactions of the present invention.

Additional objects and advantages of this invention will be apparent from the following detailed description of preferred embodiments thereof which proceeds with reference to the accompanying drawings.

BRIEF DESCRIPTION OF THE DRAWINGS

FIG. 1A is a reaction diagram showing a portion of a synthesis (olefin metathesis) of 5-decenyl acetate, in which allyl magnesium chloride is reacted with bromochloropropane to yield 1-chloro-5-hexene, as disclosed in U.S. Pat. No. 5,916,983.

FIG. 1B is a reaction diagram showing the second step of the synthesis of 5-decenyl acetate, in which 1-chloro-hexene is reacted with 1-hexene in the presence of Catalyst 823 to yield 1-chloro-5-decene.

FIG. 1C is a reaction diagram showing the third step of the synthesis of 5-decenyl acetate, in which 1-chloro-5-decene is heated with potassium acetate to yield 5-decenyl acetate.

FIG. 1D is a reaction diagram showing the fourth step of the synthesis of 5-decenyl acetate, in which a 60:40 trans:cis ratio of 5-decenyl acetate is isomerized in the presence of the sodium salt of benzenesulfinic acid and acetic acid to yield an 80:20 trans:cis ratio of 5-decenyl acetate.

FIG. 2 is a structural diagram of a generic metathesis Class I Catalyst.

FIG. 2M presents Table I, which includes the molecular weights, CAS #s, and chemical names for the Class I metathesis catalysts presented in FIGS. 2A–2L.

FIG. 3 is a structural diagram of a generic metathesis Class II Catalyst.

FIG. 3G presents Table II, which includes the molecular weights, CAS #s, and chemical names for the Class II metathesis catalysts presented in FIGS. 3A–F.

FIG. 4 is a structural diagram of a generic metathesis Class III Catalyst.

FIG. 4M presents Table III, which includes the molecular weights, CAS #s, and chemical names for the Class III metathesis catalysts presented in FIGS. 4A–4L.

FIG. 5 is a structural diagram of a generic metathesis Class IV Catalyst.

FIG. 5M presents Table IV, which includes the molecular weights, CAS #s, and chemical names for the Class IV metathesis catalysts presented in FIGS. 5A–5L.

FIG. 6 shows several generic cross metathesis reactions that may employ the preferred starting materials and the preferred metathesis catalysts.

FIG. 7 is a table showing a variety of preferred starting materials and metathesis products in accordance with the reactions shown in FIG. 6.

FIG. 8 is an additional table showing a variety of preferred starting materials and metathesis products in accordance with the reactions shown in FIG. 6.

FIG. 20 shows an alternative synthesis of 11-tetradecenyl acetate from 11-eicosenyl acetate.

DETAILED DESCRIPTION OF PREFERRED EMBODIMENTS

Figure 2A:
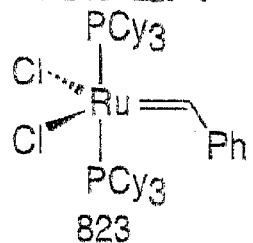
FIGS. 2A–2L are respective structural diagrams of Catalysts 823, 739, 801, 716, 849, 765, 791, 707, 815, 731, 834, and 751.
Figure 2B:
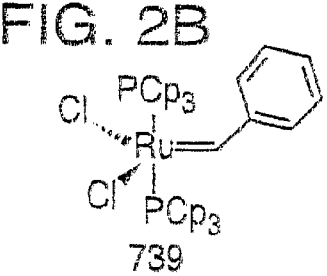

The present invention provides metathesis syntheses for a variety of value-added metathesis products such as olefinic alcohols, acetates, aldehydes, carboxylic acids or derivatives thereof in an economical and efficient manner. Most of the cross-metathesis reactions are run neat, and the unreacted starting materials are recycled back into the next cross-metathesis reaction. The invention provides the ability to cross-metathesize two different or similar terminal olefins (i.e. alpha olefin) to produce a new internal olefin, the ability to cross metathesize a terminal olefin and an internal olefin to yield a new internal olefin, the ability to cross metathesize a terminal olefin and a cyclic olefin to yield a new terminal and/or internal olefin, and the ability to cross-metathesize two similar or different internal olefins to yield a new internal olefin product.

In preferred general embodiments, a reactant of the form $R-(CH=CH)_k(CH_2)_n(CHX)_g(CH_2)_m-H$ can be self-metathesized, cross-metathesized with a different reactant of the same form, or cross-metathesized with a reactant of the form $QCH(CH_2)_rW$. When self-metathesized, this reactant forms a product of the form $(CH=CH)_k[(CH_2)_n(CHX)_g(CH_2)_m-H]_2$ and side products of the form $CH_2=CH_2$ and $RCH=CHR$. If these side products are volatile, they can easily be removed under vacuum pressure or under high temperature. In a general embodiment, X is selected from a hydrogen (H), an alcohol (OH), an acetate (AcO), a carboxylate ester $(CO_2R_a)$ where $R_a$ is an alkyl, aryl, or metal, a carboxylic acid $(CO_2H)$, an aldehyde, a halide (Cl, Br, I), a tosylate (TsO), or a mesylate (MesO) or derivatives thereof. In a more preferred embodiment, X is selected from hydrogen, an alcohol, an acetate, trifluoroacetate, methyl carboxylate, ethyl carboxylate, sodium carboxylate, chloride, bromide, iodide, or mesylate.

In a general embodiment, g, k, m, and n are each selected from zero and an integer less than or equal to 20. In a more preferred embodiment, g is selected from zero and an integer less than or equal to 5. In a most preferred embodiment, g equals 0, 1, or 2. In a more preferred embodiment, k is selected from an integer from 1 to 5. In a most preferred embodiment, k equals 1. In a more preferred embodiment, m is selected from zero and an integer less than or equal to 15. In a most preferred embodiment, m equals 0, 1, or 2. In a more preferred embodiment, n is selected from zero and an integer less than or equal to 10. In a most preferred embodiment, n is equal to 0, 1, 3, 4, 5, 7, or 10. In a general embodiment, R is selected from hydrogen, alkyl, aryl, or derivatives thereof. In a more preferred embodiment, R is selected from hydrogen, a $C_1-C_{20}$ alkyl, borate diisopropyl ester, borate pinacol ester, borate catechol ester, borate neopentyl glycol ester, dialkyl phosphonate ester, trialkyl silane ester, or trialkyl siloxane ester. In a most preferred embodiment, $R-(CH=CH)_k(CH_2)_n(CHX)_g(CH_2)_mH$ describes 5-hexenyl acetate, 5-hexenyl alcohol, 5-decene, 1-hexene, 1-butene, 1-dodecene, 11-docosene, 1,10-diacetoxy-5-decene, 3-hexene, 11-eicosenyl acetate, 11-eicosenol, 11-eicosenoic acid, 5-eicosenyl acetate, 5-eicosenol, 5-eicosenoic acid, 10-undecenoic acid, 10-undecenol, 10-undecenoate ester, vinyl borate pinacol ester, vinyl diethyl phosphonate, allyl diethyl phosphonate, vinyl triethoxy silane, or allyl triethoxy silane.

The cross-metathesis of $R-(CH=CH)_k(CH_2)_n(CHX)_g(CH_2)_m-H$ with a reactant of the form $QCH(CH_2)_rW$ forms a product $H(CH_2)_m(CHX)_g(CH_2)_n(CH=CH)_p(CH_2)_rW$ or derivatives thereof and a side product in the form of $CH_2Z$. In preferred embodiments, Q is selected from $CH_2$ or $CH(CH_2)_rW$, r is selected from zero and an integer less than or equal to 20; W is selected from an alcohol, acetate, carboxylate ester, carboxylic acid, aldehyde, halide, hydrogen, or derivative thereof; Z is selected from $CH_2$ or $CH(CH_2)_n(CHX)_g(CH_2)_m$; and p is selected from zero and an integer less than or equal to the sum of m and n and operated under conditions of sufficiently high temperature and/or sufficiently low pressure (vacuum) such that the side product evaporates out of the reaction mixture.

Figure 2C:
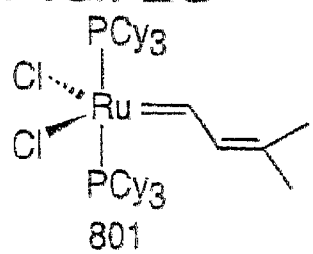
Figure 2D:
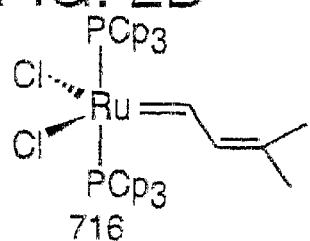
Figure 2E:
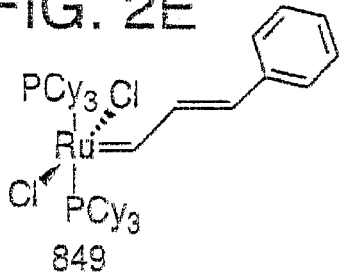
Figure 2F:
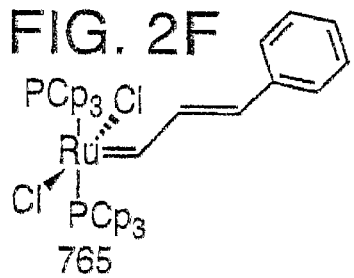
Figure 2G:
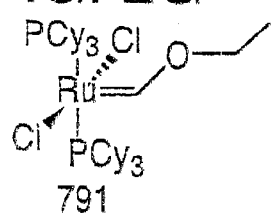
Figure 2H:
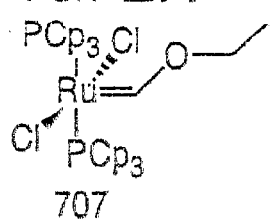
Figure 2I:
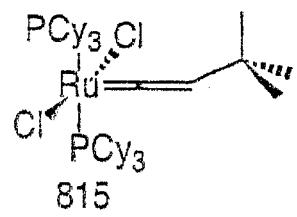
Figure 2J:
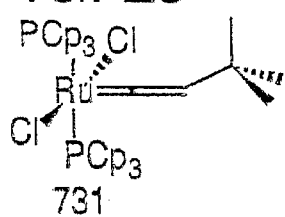
Figure 2K:
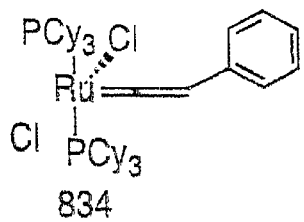
Figure 2L:
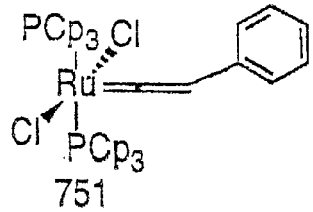
Figure 2X:
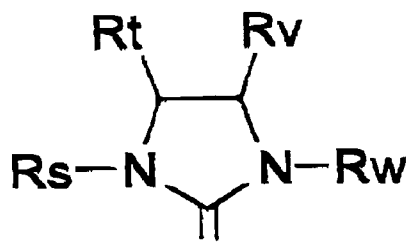
FIGS. 2X and 2Y are alternative heterocyclic carbene ligands for an exemplary metathesis catalyst.
Figure 2Y:
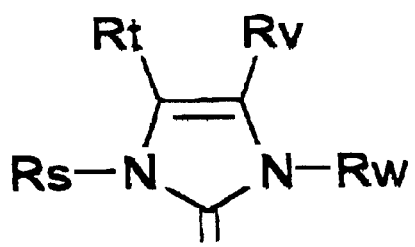

In general, any metathesis catalyst stable under the reaction conditions and nonreactive with the functional groups (X) present on the reactant may be used with the present invention. Due to their excellent stability and functional group tolerance, particularly preferred metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CR$_b$R$_c$ or LL'AA'M=(C=)$_n$CR$_b$R$_c$; wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes of the structures shown in FIGS. 2X or 2Y, where R$_s$ and R$_w$ are independently selected from alkyl, aryl, or substituted aryl, preferably substituted phenyls and most preferably mesityl (i.e. 2,4,6-trimethylphenyl), where R$_t$ and R$_v$ are preferably selected from alkyl or aryl, or form a cycloalkyl, and most preferably are both hydrogen, t-butyl, or phenyl (These imidazolidine ligands are referred to as 4,5-dihydro-imidazole-2-ylidene ligands), and L and L' together may optionally comprise a bidentate ligand; and A and A' are anionic ligands independently selected from halogen, hydrogen, $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonyl, $C_1$–$C_{20}$ alkylsulfonyl, $C_1$–$C_{20}$ alkylsulfinyl; each ligand optionally being substituted with $C_1$–$C_5$ alkyl, halogen, $C_1$–$C_5$ alkoxy; or with a phenyl group that is optionally substituted with halogen, $C_1$–$C_5$ alkyl, or $C_1$–$C_5$ alkoxy; and A and A' together may optionally comprise a bidentate ligand; and R$_b$ and R$_c$ are independently selected from hydrogen, $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each of R$_b$ and R$_c$ optionally substituted with $C_1$–$C_5$ alkyl, halogen, $C_1$–$C_5$ alkoxy or with a phenyl group that is optionally substituted with halogen, $C_1$–$C_5$ alkyl, or $C_1$–$C_5$ alkoxy.

In some embodiments, L or L' and A or A' may form one or more ligands. (Class II catalysts). In addition, R$_b$ or R$_c$ and L or L or A or A' may form one or more bidentate ligands (Hoveyda catalyst systems).

In some preferred embodiments,

M is ruthenium or osmium;

L and L' are each independently any neutral electron donor ligand and preferably selected from alkyl phosphine, aryl phosphine, or heterocyclic carbenes of the structures shown in FIGS. 2X or 2Y, where R$_s$ and R$_w$ are independently and preferably substitutued phenyls and most preferably mesityl (i.e. 2,4,6-trimethylphenyl), where R$_t$ and R$_v$ are preferably selected from alkyl or aryl, or from a cycloalkyl, and most preferably are both hydrogen, t-butyl, or phenyl (These imidazolidine ligands are referred to as 4,5-dihydro-imidazole-2-ylidene ligands), and L and L' together may optionally comprise a bidentate ligand;

A and A' are anionic ligands independently selected from halogen, $C_1$–$C_{20}$ alkyl, aryl, $C_1$–$C_{20}$ alkoxide, aryloxide, and A and A' together may optionally comprise a bidentate ligand; and R$_b$ and R$_c$ are independently selected from hydrogen, $C_1$–$C_{20}$ alkyl, aryl, each of R$_b$ and R$_c$ optionally substituted with hydrogen, $C_1$–$C_5$ alkyl, halogen, $C_1$–$C_5$ alkoxy or with a phenyl group.

In certain preferred embodiments of these catalysts, L or L' may be selected from alkyl phosphines of the formula PR$^1$R$^2$R$^3$, where R$^1$, R$^2$, and R$^3$ are each independently aryl or $C_1$–$C_{10}$ alkyl, and in particular, primary alkyl, secondary alkyl, cycloalkyl; from substituted triarly phosphines, or from phosphines with mixed alkyl and aryl substituents.

In certain more preferred embodiments, the metathesis catalysts have a fornula: P[R$^1$R$^2$R$^3$]L'AA'Ru=CR$_b$R$_c$ or P[R$^1$R$^2$R$^3$]L'AA'Ru=C=CR$_b$R$_c$, wherein:

L' is a heterocyclic carbenes of the structures shown in FIGS. 2X or 2Y, where R$_s$ and R$_w$ are mesityl (i.e. 2,4,6-trimethylphenyl), where R$_t$ and R$_v$ are hydrogen (These imidazolidine ligands are referred to as 4,5-dihydro-imidazole-2-ylidene ligands);

R$^1$, R$^2$, and R$^3$ are each independently cyclohexyl, cyclopentyl, isopropyl, t-butyl, or phenyl;

A and A' are anionic ligands independently selected from chloride, bromide, or iodide; and R$_b$ and R$_c$ are independently selected from hydrogen, 3-methyl-2-butenylidene, allenyl phenyl and phenyl.

In certain most preferred embodiments, L and L' ligands may be selected from P(cyclohexyl)$_3$, P(cyclopentyl)$_3$, P(isopropyl)$_3$, and P(phenyl)$_3$.

One subset of metathesis catalysts, of the type [(PR$^1$R$^2$R$^3$)$_2$AA']Ru=CR$_b$R$_c$, are generically described by Grubbs et al. in International Application Nos. PCT/US95/09655 and PCT/US96/12654 and U.S. Pat. No. 6,211,391. These catalysts are generally referred to herein as Grubbs' catalysts.

Specific catalyst examples include: (PCy$_3$) sImes Cl$_2$Ru=CH=C(CH$_3$)$_2$ (848); (PCy$_3$) sImes Cl$_2$Ru=CHPh (824); (PCp$_3$) sImes Cl$_2$Ru=CH=C(CH$_3$)$_2$ (785); (PCp$_3$) sImes Cl$_2$Ru=CHPh (807); (PPh$_3$) sImes Cl$_2$Ru=CH=C(CH$_3$)$_2$; (PPh$_3$) sImes Cl$_2$Ru=CHPh; (PCy$_3$) sImes Cl$_2$Ru=C=CHPh; (PCp$_3$) sImes Cl$_2$Ru=C=CHPh; and (PPh$_3$) sImes Cl$_2$Ru=C=CHPh, where sImes are 4,5-dihydro-imidazole-2-ylidene ligands.

Another subset of metathesis catalysts of the general formula [X$_a$L"L'''M=(C=)$_n$CR$_a$R$_b$]+Y— are tetracoordinated cationic metal carbene complexes wherein L" are phosphine ligands, L''' are neutral pi-bonded ligands, X$_a$ is halogen, R$_a$ and R$_b$ are hydrogen or hydrocarbon, n is 0–5, Y— is any non-coordinating anion; and are generically described by A. Furstner, et al. in International Application No. PCT/EP98/07364.

Some of these catalysts, such as Class I metathesis catalysts, are preferred. A generic Class I metathesis catalyst is shown in FIG. 2. With reference to FIG. 2, R$_b$ and R$_c$ are the same as set forth in the above paragraph. Preferred Class I metathesis catalysts include, but are not limited to, Catalysts 823, 739, 801, 716, 849, 765, 791, 707, 815, 731, 834, and 751. These catalysts are respectively shown in FIGS. 2A–2L (collectively FIG. 2). Specific catalysts are, for convenience, herein referred to by their molecular weights, some of which are the rounded off and shown below each structure in the figures. They are also tabulated by FIG. # with their respective molecular weights, CAS #s, and chemical names in FIG. 2M for convenience. Many of these catalysts are commercially available, but they are not generally thermally stable, and they generally cannot be used to synthesize trisubstituted olefins.

With reference to FIG. 2A, Catalyst 823 and variations of it, are particularly preferred. Catalyst 823 has a chemical formula [(PCy$_3$)$_2$Cl$_2$]Ru=CHPh, where Cy represents a cyclohexyl group and Ph represents a phenyl group. Synthesis of Catalyst 823 is described in U.S. Pat. No. 5,916,983.

Bis(tricyclohexylphosphine)dichloro ruthenium (II) 3-methyl-1,2-butadiene, Catalyst 801, and bis(tricyclopentylphosphine)dichloro ruthenium (II) 3-methyl-1,2-butadiene, Catalyst 716, are shown respectively in FIGS. 2C and 2D. Catalysts 801 and 716 can be synthesized as described in U.S. Pat No. 5,917,071 and are also preferred metathesis catalysts.

A generic Class II metathesis catalyst is shown in FIG. 3. Preferred Class II metathesis catalysts include, but are not limited to, Catalysts 877, 835, 855, 813, 903, and 881. These catalysts are shown respectively in FIGS. 3A–3F (collectively FIG. 3). They are also tabulated by FIG. # with their respective molecular weights, CAS #s, and chemical names in FIG. 3G for convenience. These catalysts tends to be more thermally stable and more active than the Class I catalysts, but Class. II catalysts are not commercially available or readily synthesized. In addition, the Class II catalysts cannot generally synthesize trisubstituted olefins.

A generic Class III metathesis catalyst is shown in FIG. 4, where $R_s$ and $R_w$ have been previously defined and are preferably diorthoaryl- or triaryl-substituted rings, and are most preferably mesityl. Preferred Class III metathesis catalysts include, but are not limited to, Catalysts 846, 805, 824, 783, 873, 831, 814, 773, 839, 797, 859, and 817. These catalysts are shown respectively in FIGS. 4A–4L (collectively FIG. 4). They are also tabulated by FIG. # with their respective molecular weights, CAS #s, and chemical names in FIG. 4M for convenience. The Class III catalysts are generally more thermally stable and more active than the Class I and Class II catalysts. The Class III catalysts are not commercially available and are not readily synthesized. However, unlike Class I and Class II catalysts, Class III catalysts can be used to synthesize selected trisubstituted olefins, but cannot generally synthesize tetrasubstituted olefins.

A generic Class IV metathesis catalyst is shown in FIG. 5, where $R_s$ and $R_w$ have been previously defined and are preferably diorthoaryl- or triaryl-substituted rings, and are most preferably mesityl. Preferred Class IV metathesis catalysts include, but are not limited to, Catalysts 848, 807, 826, 785, 875, 833, 816, 775, 841, 799, 861, and 819. These catalysts are respectively shown in FIGS. 5A–5L (collectively FIG. 5). They are also tabulated by FIG. # with their respective molecular weights, CAS #s, and chemical names in Table IV of FIG. 5M for convenience. The Class IV catalysts are generally more thermally stable and more active than the Class I–III catalysts. Reactions employing the Class IV catalysts generally need about 8 to 10 times less catalyst, particularly 848, compared to the amounts of Class I catalysts, particularly 823 or 801, needed for the same reaction to obtain about the same yields. Furthermore, the Class IV catalysts, particularly 848, complete a reaction in less than one hour while the Class I catalysts complete the same reaction in about 19 to 24 hours. Some of the Class IV catalysts specified above can be synthesized as described by Scholl et al. (1999). The Class IV catalysts are especially preferred because they can be used to synthesize tetrasubstituted olefins as well as trisubstituted olefins.

Some of these catalysts of the formula where L and L' are independently selected from phosphine ligands PR$^1$R$^2$R$^3$ as previously defined or heterocyclic ligands with cycloalkyl, or alkyl-substituted cycloalkyl groups wherein the number of carbon atoms in the heterocyclic ring is from 4 to 12, or more generally designated as Cyclic (NR$_w$)[(CH$_h$)R$_t$][(CH$_h$)(R$_v$)](NR$_s$)C:

wherein h is from 0 to 9 and R$_w$, R$_s$, R$_t$, and R$_v$ are selected from hydrogen, aryl and alkyl, and where R$_d$ and R$_j$ have been described above. The most preferred embodiment of L' are the structures shown in FIGS. 2X and 2Y where R$_w$ and R$_s$ are selected from 2,4,6-trimethyl phenyl, isopropyl, or t-butyl.

Figure 5A:
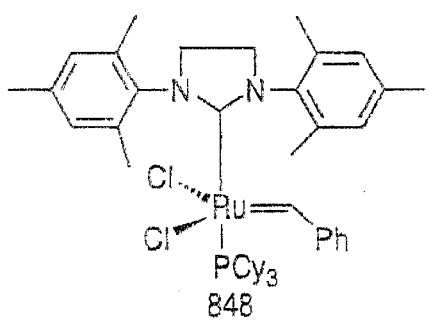
FIGS. 5A–5L are respective structural diagrams of Catalysts 848, 807, 826, 785, 875, 833, 816, 775, 841, 799, 861, and 819.
Figure 5B:
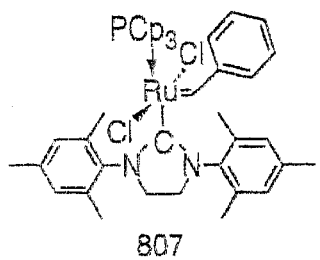
Figure 5C:
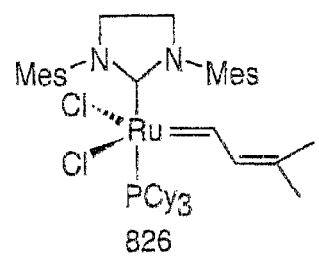
Figure 5D:
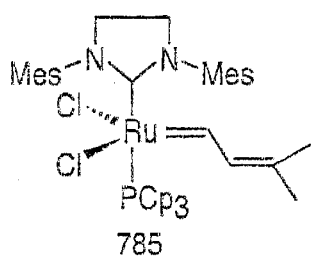
Figure 5E:
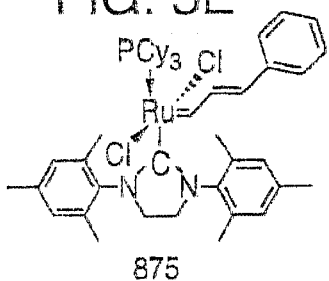
Figure 5F:
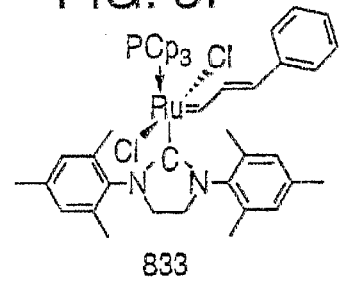
Figure 5G:
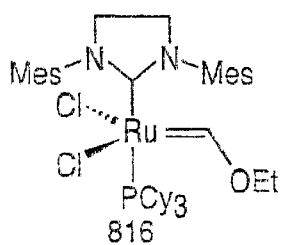
Figure 5H:
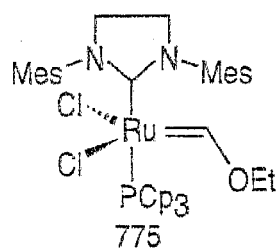
Figure 5I:
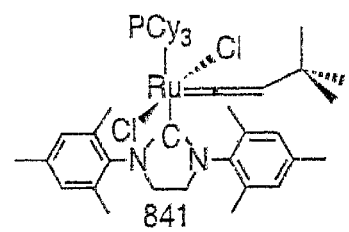
Figure 5J:
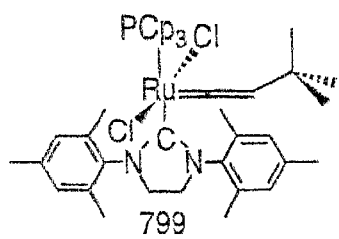
Figure 5K:
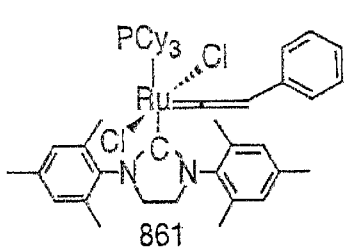
Figure 5L:
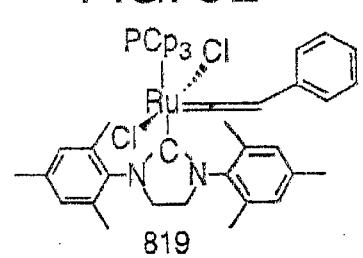

This family of 1,3-dimesityl-4,5-dihydro-imidazol-2-ylidene-substituted ruthenium-based complexes are preferred, such as Catalyst 848, shown in FIG. 5A. The synthesis of Catalyst 848 is described in *Organic Letters*, "Synthesis and Activity of a New Generation of Ruthenium-Based Olefin Metathesis Catalysts Coordinated with 1,3-Dimesityl-4,5-dihydro-imidazol-2-ylidene Ligands," Scholl et al. (1999). Catalysts 848, 826, and 785 can be synthesized as described by Scholl et al (1999).

Catalysts 816 and 794 are synthesized by adding two equivalents of ethyl vinyl ether to catalyst 848, stirring at room temperature for about three hours and isolating by precipitation. Catalysts 816 and 794 have very interesting properties as they initiate the metathesis reactions in well defined temperature profiles. Reaction mixtures containing Class I and Class II catalysts must be kept at extremely low temperatures, such as in the range of −40 to −70° C., to prevent them from initiating the reaction. Most Class III and some Class IV catalysts must be kept at relatively low temperatures to prevent reaction. However, reaction mixtures containing Catalysts 816 and 794 have a higher initiation temperature, about 35° C., which allows all the reactants to be throughly mixed before the reaction is initiated, and allows the reaction to be better controlled.

Other metathesis catalysts such as "well defined catalysts" could be alternatively be employed. Such catalysts include, but are not limited to, Schrock's molybdenum metathesis catalyst, 2,6-diisopropylphenylimido neophylidenemolybdenum (VI) bis(hexafluoro-t-butoxide), described by Grubbs et al. in *Tetrahedron* (1998), 54, 4413–4450 and Basset's tungsten metathesis catalyst described in Couturier, J. L. et al. *Angew. Chem. Int. Ed. Engl.* (1992) 31,628. Schrock's catalyst is available from Strem (Newburyport, Mass.), but may be too expensive for large scale production of PTB pheromone. Basset's catalyst is not presently commercially available, is sensitive to air, water, and a variety of functional groups, and may be too expensive to use in a commercial process.

Other metathesis catalysts such as "non-well defined catalysts" could also be employed, but their activity depends on co-catalysts, which are typically heavy metals such as tetraalkyl tin or tetraalkyl lead compounds and present a waste disposal issue. These non-well defined catalysts also require for activation the presence of strong Lewis acids, which may cause undesirable double bond migration.

FIG. 6 shows several generic cross metathesis reactions that may employ preferred an other similar materials and the preferred Class I–IV or other metathesis catalysts. With reference to FIG. 6, T, U, V, and D are chosen from hydrogen, alkyl aryl, hydroxy, acetate, protected alcohol, halide, mesylate, tosylate, etc.; x, e, y, and z are selected from 0 to 10; and t1 is selected from 2 to 22. In Scheme A, two similar terminal olefins are self metathesized to yield an internal olefin. Specific examples include the self-metathesis of 5-hexenyl acetate (T=acetate and x=4) to 1,10-diacetoxy-5-decene and 4-pentyl chloride (T=chloride and x=3) to 1,8-dichloro-4-octene.

In Scheme B, an internal olefin is cross-metathesized with itself to yield two new internal olefins. A specific example is the cross-metathesis of 1-chloro-3-hexene (U=CH$_3$, V=Cl, y=1 and z=1) to yield 1,6-dichloro-3-hexene (V=Cl and y=1) and 3-hexene (U=CH$_3$ and z=1).

In Scheme C, two dissimilar terminal olefins are cross metathesize to yield a new internal olefin. A specific example is the cross metathesis of hexenyl acetate (T=Ac and x=4) and vinyl borate pinacol ester (D=borate pinacol ester and e=0) to yield hexenyl boroate pinacol ester (T=Ac, x=4, D=borate pinacol ester and e=0).

In Scheme D, a terminal olefin and an internal olefin are cross metathesized to yield a new internal olefin. A specific example is the cross metathesis of 1,10-diacetoxy-5-decene (T=Ac, x=4) and vinyl borate pinacol ester (D=borate pinacol ester and e=0) to yield hexenyl borate pinacol ester (T=Ac, x=4, D=borate pinacol ester and e=0).

In Scheme E, two different internal olefins are cross metathesized to yield a new internal olefin. A specific example is the cross metathesis of 1,6-dichloro-3-hexene (V=Cl, y=1) and 1,10-diacetoxy-5-decene (T=Ac, x=4) to yield 8-chloro-5-octenyl acetate (V=Cl, y=1, T=Ac, x=4).

In Schemes F and G, the cross-metathesis products are hydrogenated under normal hydogenation conditions to yield corresponding saturated alkyl products. Specific examples include 8-chloro-5-octenyl acetate (V=Cl, y=1, T=Ac, x=4) to omega-chlorooctanyl acetate (V=Cl, T=Ac, t1=8) and 10-bromo-5-decenyl acetate (U=Br, y=4, T=Ac, x=4) to omega-bromodecenyl acetate (V=Br, T=Ac, t1=10).

In general, these reactions with many of the metathesis catalysts disclosed herein provide yields better than 15%, preferably better than 50%, more preferably better than 75%, and most preferably better than 90%. In addition, the reactants and products are chosen to provide at least a 5° C. difference, preferably a greater than 20° C. difference, and most preferably a greater than 40° C. difference. Finally, because the metathesis catalyst reactions are typically fast compared to impurity formation, it is desirable to run these reactions as quickly as practical. In particular, the reactions are performed in less than about 24 hours, preferably less than 12 hours, more preferably less 8 hours, and most preferably less than 4 hours.

The following reactions, figures, and examples are shown herein only by way of example to the above-described type of metathesis syntheses and should not be considered as limiting the scope of the invention. However, each synthetic route that employs a self-metathesis reaction and a cross-metathesis reaction preferably employs the same catalyst for both reactions.

FIG. 7 shows Table V which presents a variety of preferred starting materials and metathesis products in accordance with the reactions shown in FIG. 6.

FIG. 8 shows Table VI which presents additional preferred starting materials and metathesis products in accordance with the reactions shown in FIG. 6. With reference to FIG. 8, acetate, TMS, THP, and EVE protecting groups are preferred, and the halogroups are preferably fluoro, chloro, bromo, iodo, mesyl, tosyl, or the like.

Figure 9A:
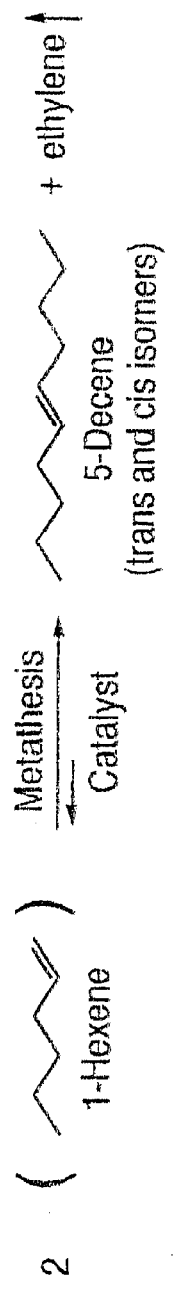
FIG. 9A shows a first step of an improved synthesis of 5-decenyl acetate, in which 1-hexene is self-metathesized to 5-decene and ethylene is removed from the reaction by venting to atmosphere.
Figure 9B:
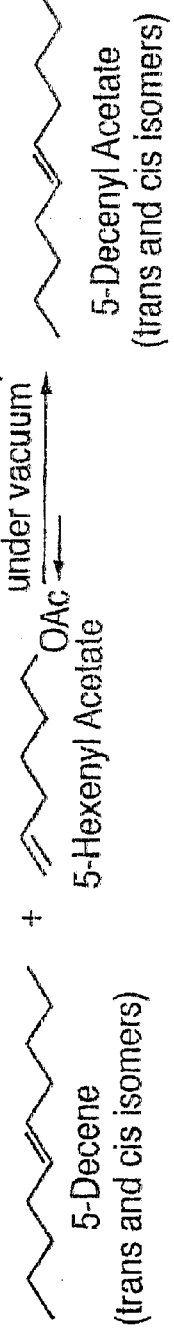
FIG. 9B shows a second step of an improved synthesis of 5-decenyl acetate, in which 5-decene is reacted with 5-hexenyl acetate and under vacuum to yield 1-hexene and an 80:20 to 84:16 trans:cis ratio of 5-decenyl acetate.

FIGS. 9A and 9B (collectively FIG. 9) show an improved synthesis of 5-decenyl acetate. In particular, FIG. 9 shows the self-metathesization of 1-hexene to form 5-decene in the presence of Catalyst 823. The reaction favors 5-decene formation because ethylene is removed from the reaction as it is formed. FIG. 9B shows the cross-metathesization of 5-decene and 5-hexenyl acetate (5-hexen-1-yl acetate) in the presence of Catalyst 823 and under vacuum. Running the reaction under vacuum removes 1-hexene and results in high conversions of 5-hexenyl acetate to 5-decenyl acetate and an 84:16 trans: cis ratio of isomeric products. The following examples demonstrate the preparation of the PTB pheromone, but should not be regarded as a limitations to the scope of the invention.

EXAMPLE 1

Synthesis of 5-Decene: Self-metathesis of 1-Hexene

With reference to FIG. 9A, to a dry 2-L round-bottomed flask was added 225 g (2.67 mol) 1-hexene (available from Amoco at a purity of greater than 95%) and a magnetic stir bar. The flask was sparged with nitrogen for 10 minutes. Catalyst 823 (2.2 g, 2.7 mmol) was added and the reaction was stirred at room temperature for 18 hours. The evolution of ethylene gas from the reaction was observed. The spent catalyst was removed by filtering the reaction through 200 g of J. T. Baker Silica Gel 60–200 mesh in a 1.5 inch×22 inch chromatography column. The column was rinsed with 300 mL of petroleum ethers (38° C. to 55° C. boiling point). The solvent and unreacted 1-hexene were removed under reduced pressure to yield 115 g (0.81 mol) of 5-decene. This product was used in the next reaction without further purification.

Synthesis of 5-Decenyl Acetate: Cross Metathesis of 5-Decene and 5-Hexenyl Acetate With reference to FIG. 9B, to a dry 1-L round-bottomed flask was added 115 g (0.81 mol) 5-decene, 22.5 g (0.158 mol) 5-hexenyl acetate (available from TCI America under the name of acetic acid 5-hexenyl ester at a purity of greater than 98%), and a magnetic stirbar. The flask was sparged with nitrogen for 5 minutes, Catalyst 823 1.33 g (1.6 mmol) was added, and the flask was run under an 8 mmHg vacuum for 16 hours. After 16 hours, the vacuum pump was removed and the reaction was stirred for an additional 12 hours under a nitrogen atmosphere. GC analysis indicated 87 percent 5-decenyl acetate, 12 percent 1,10-diacetoxy-5-decene, and less than one percent 5-hexenyl acetate.

A purified sample of 5-decenyl acetate was obtained by filtering about half of the reaction mixture through 500 g of J.T. Baker silica gel in a 1.5 inch×22 inch chromatography column. The column was rinsed with 1 L of petroleum ether, followed by rinsing with 1 L of 10 percent diethyl ether in petroleum ether. Two hundred-milliliter fractions were collected. The data are summarized below.

GC Results

| Fraction Number | 5-decene | 5-decenyl acetate | 1, 10-diacetoxy-5-decene |
|---|---|---|---|
| 1 | 0 | 0 | 0 |
| 2 | 100 | 0 | 0 |
| 3 | 91 | 9 | 0 |
| 4 | 0 | 100 | 0 |
| 5 | 0 | 100 | 0 |
| 6 | 0 | 100 | 0 |
| 7 | 0 | 100 | 0 |
| 8 | 0 | 0 | 0 |
| 9 | 0 | 0 | 100 |
| 10 | 0 | 0 | 100 |
| 11 | 0 | 0 | 0 |

Fractions 4, 5, 6, and 7 were combined and concentrated under reduced pressure to yield 10.6 g (53.5 mmol) of 99.4 percent chemical purity and a 81:19 trans:cis isomeric ratio.

EXAMPLE 2

Synthesis of 5-Decene: Self-metathesis of 1-Hexene

With reference again to FIG. 9A, to a clean 72 L round bottomed flask connected to a: pneumatic overhead stirrer (a high efficiency reflux condenser with −10° C. circulating coolant) was added 48L (384 mol) of 1-hexene (obtained from Amoco at a purity of greater than 99 percent and used without further purification). Stirring was initiated and the solution was sparged with nitrogen from below the surface for 15 minutes. Catalyst 823 (10 g, 0.018 mol) was added and stirred under a nitrogen atmosphere for 18 to 24 hours. The ethylene was vented through the high efficiency condenser into an exhaust duct.

After 24 hours, GC analysis indicated 60 to 70 percent conversion of 1-hexene to 5-decene. This reaction mixture was filtered through 2.5 Kg of silica gel (Fisher 170–400 mesh, 60 Å) to remove the spent catalyst.

Skilled persons will appreciate that the materials can be carried through to the next reactions without purification of the intermediate compounds. However, if purification is desired, the intermediates can be isolated, e.g. the 5-decene can be distilled or otherwise purified.

Synthesis of 5-Decenyl Acetate: Cross Metathesis of 5-Decene and 5-Hexenyl Acetate With reference again to FIG. 9B, a clean 72 L round bottomed flask was loaded with 60 L of 5-decene (60% to 70% purity) and connected to a pneumatic overhead stirrer and a vacuum distillation setup. The vacuum distillation set up included a 3"×36" distillation column and a high efficiency heat exchanger and 1" take-off head which ran to a 22 L receiving flask. Two vacuum traps were inserted after the 22 L receiving flask and in front of the high capacity vacuum pump.

Catalyst 823 (100 g, 0.122 mol) was added to the round bottom flask, stirring was initiated, a vacuum was applied, and the heating mantels were turned to setting 2. The temperature of the reaction mixture was maintained below 45° C., and the vacuum pressure was adjusted to prevent 5-decene from distilling out of the 72 L flask. 5-Hexenyl acetate (99% purity, 12 L, 76 mol) was added over 5 hours. After the addition was completed, the heating mantels were turned off, and the reaction was stirred under a 10 mmHg vacuum. After 12 hours, the vacuum traps were emptied and repacked with dry ice, and vacuum was applied again.

Skilled persons will appreciate that the metathesis reactions are preferably conducted between about 25° C. and 60° C., depending on the vacuum being pulled on the reaction, and most preferably between about 25° C. and 35° C. at about 10 mmHg.

GC analysis of the metathesis reaction indicates 0.1% 1-hexene, 64.9% 5-decene, 0.08% 5-hexenyl acetate, 30.8% 5-decenyl acetate (82% trans and 18% cis isomers), and 4.1% 1,10-diacetoxy-5-decene.

Yields ranging from 54 to 83 percent have been obtained at the 12 Kg scale. The yield can be manipulated by changing the ratio of 5-decene to hexenyl acetate. Because the 1-hexene is removed under the strong vacuum, increasing the ratio of 5-decene increases the yield of 5-decenyl acetate; however, this increased ratio decreases the throughput, i.e. decreases the number of Kg of 5-decenyl acetate made in a run. At the 12 Kg scale, a 75:25 ratio of 5-decene:1-hexene to a 50:50 of 5-decene: 1-hexene will work to convert greater than 99 percent of 5-hexenyl acetate into 5-decenyl acetate and 1,10-diacetoxy-5-decene.

The high conversion of starting materials to products resulting from running the reaction under vacuum was unexpected. The application of vacuum was attempted to remove ethylene in the hope of enhancing the conversion up to about 75 percent; however, the removal of 1-hexene to obtain greater than a 99 percent conversion of 5-hexenyl acetate was completely unexpected.

The preferred embodiments reduce the number of synthetic steps from four to two and reduce the amount of time required to synthesize the end product from over 20 days to as few as two days with the same scale of materials and same type of equipment. This represents a time reduction by a factor of ten. By employing the procedure of Example 2, a skilled person can produce 12 Kg of 5-decenyl acetate in an 83:17 trans:cis ratio in 48 hours or less. This process time includes the metathesis reactions and catalyst removal, but does not include the final distillation.

In addition to being more expedient, the present process also reduces the cost of production of 5-decenyl acetate. For example, present process has been demonstrated to produce 5-decenyl acetate in the preferred trans:cis ratio for a cost of generally less than $0.40 per gram. The lack of waste solvents and waste products substantially reduces the cost of the reactions, including the costs of both purchasing the solvents and disposing of the waste. A further advantage is that the starting materials, such as 1-hexene and 5-hexenyl acetate, are commercially available.

Catalyst Removal Procedure

Figure 10A:
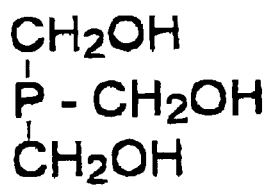
FIG. 10A shows a generic structural formula for trishydroxymethyl phosphine used for removal of preferred metathesis catalysts.

The metathesis catalyst is removed by a water soluble phosphine such as trishydroxymethyl phosphine (THMP) shown in FIG. 10A. THMP is preferred and can be made from tetrakis hydroxymethyl phosphonium chloride (TKC) as described by J. W. Ellis et al. *Inorg. Chem.* (1992) 31, 3026 and N. J. Goodwin et al. *Chem. Commun.* (1996) 1551. TKC is in an 80 percent solution in water. A better procedure is to add 100 mmol of tetrakishydroxymethyl phosphonium chloride (also know as Pyroset TKC from Cytec) to 100 mL of isopropanol, degas with nitrogen for 10 minutes, add 100 mmol of potassium hydroxide pellets, and stir for 15 minutes or until the potassium hydroxide dissolves. The product can be used without further purification or can be stirred in the refrigerator until needed.

This procedure can be used generically to make polyhydroxyalkyl phosphines or polyhydroxyaryl phosphines from the corresponding polyhydroxyalkyl-hydroxymethyl phosphonium halide salts or polyhydroxyaryl-hydroxymethyl phosphonium halide salts with a molar equivalent of base, preferably potassium hydroxide or sodium hydroxide. The substantially equal molar ratio of base with the hydroxymethyl phosphonium derivatives is essential to yield the desired polyhydroxyalkyl phosphines or polyhydroxyaryl phosphines because the base first eliminates hydroxymethyl in the form of formaldehyde to yield the phosphine. Any excess base reacts with the phosphine to yield the polyhydroxyalkyl phosphine oxide or polyhydroxyaryl phosphine oxide, which are inert to the metathesis catalyst and will not remove the metathesis catalyst from the reaction mixture.

Figure 10B:
FIG. 10B shows a generic structural formula for preferred water soluble phosphines or phosphites used for removal of preferred metathesis catalysts.
Figure 10C:
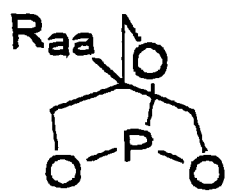
FIG. 10C shows a generic structural formula of preferred water soluble phosphine ring systems used for removal of preferred metathesis catalysts.
Figure 3A:
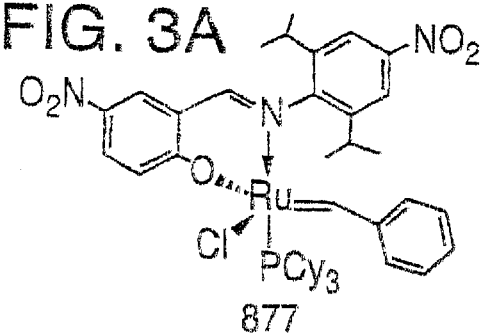
FIGS. 3A–3F are respective structural diagrams of Catalysts 877, 835, 855, 813, 903, and 881.
Figure 3B:
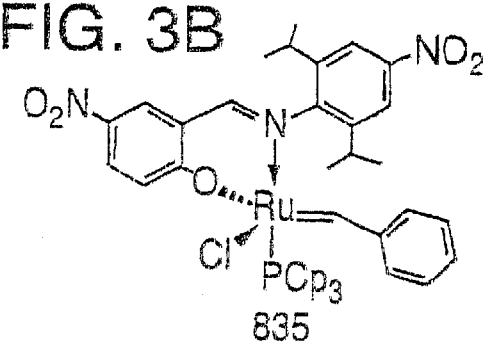
Figure 3C:
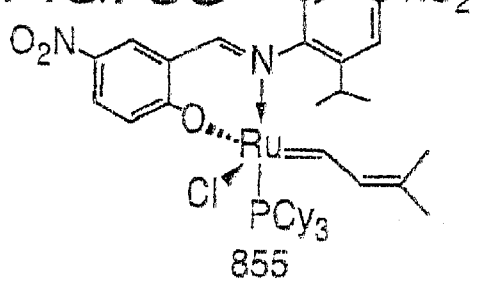
Figure 3D:
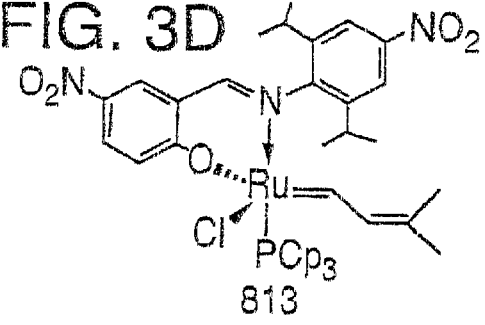
Figure 3E:
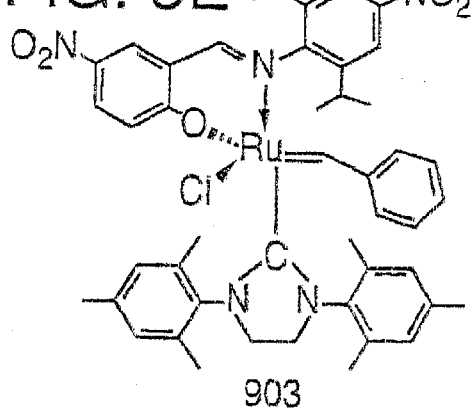
Figure 3F:
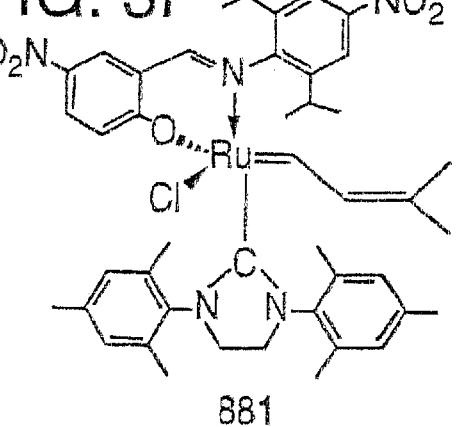
Figure 4A:
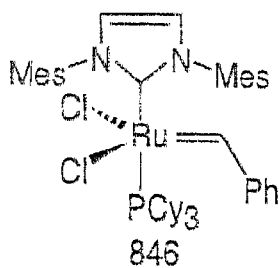
FIGS. 4A–4L are respective structural diagrams of Catalysts 846, 805, 824, 783, 873, 831, 814, 773, 839, 797, 859, and 817.
Figure 4B:
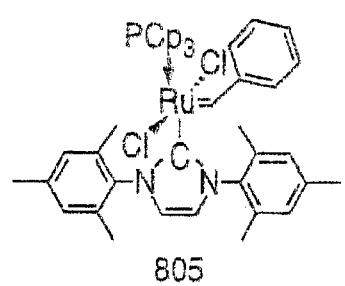
Figure 4C:
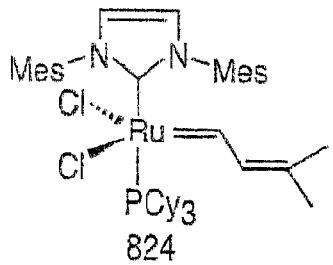
Figure 4D:
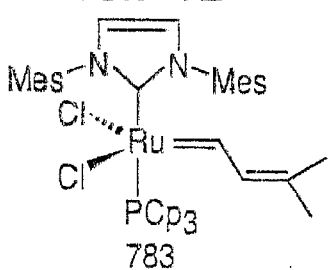
Figure 4E:
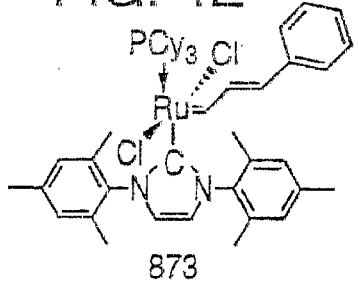
Figure 4F:
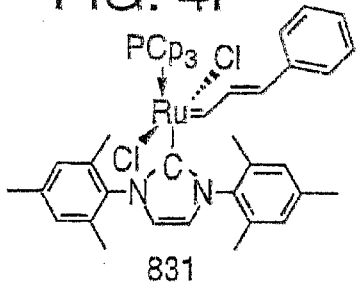
Figure 4G:
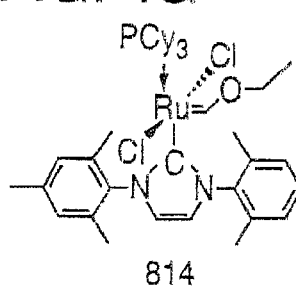
Figure 4H:
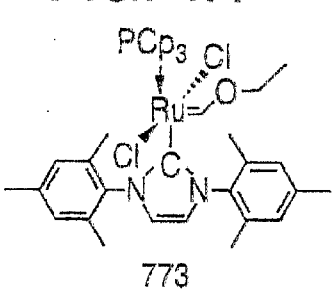
Figure 4I:
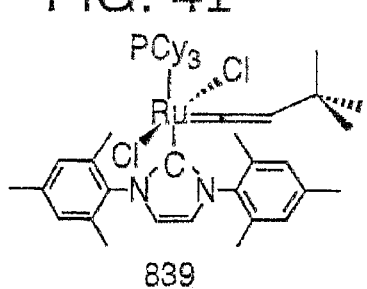
Figure 4J:
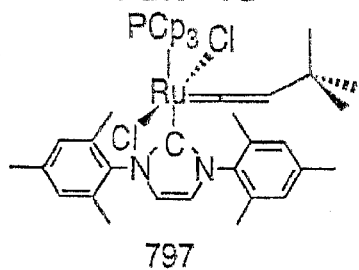
Figure 4K:
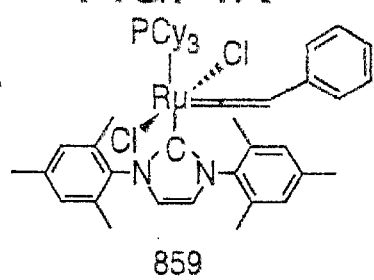
Figure 4L:
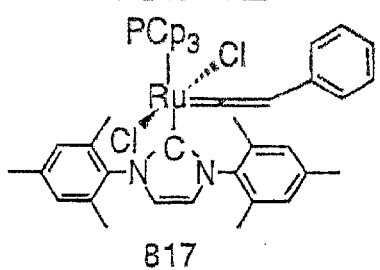

FIG. 10B shows a generic structural formula for other preferred acyclic water soluble phosphines, where q is 0 or 1 and $R_{aa}$, $R_{bb}$, and $R_{cc}$ are selected from H; $CH_3$; $CH_2OH$; $CH_2OCH_3$; $CH_2CH_2OCH_3$; $(CH_2CH_2O)_{xx}$, where xx is from 1 to 20; amine; carboxylate; sulfonate; or the like. FIG. 10C shows a generic structural formula of preferred water soluble phosphine ring systems having 4 to 40 carbon atoms and 3 to 20 oxygen atoms.

The metathesis reaction mixture from Example 2 above (20 L containing approximately 0.041 mol of metathesis catalyst) was added to a 22 L flask that was connected to a pneumatic overhead stirrer and placed in a sand temperature bath, heated above room temperature and preferably to about 55° C. The THMP solution was added and reaction was vigorously stirred for 12 to 24 hours. Nitrogen sparged water (2 L) was added and vigorously stirred for one hour. Stirring was stopped and the phases separated. The bright orange aqueous phase was removed, and another 2 L of water was added and stirred vigorously for 30 minutes. Again the phases were separated and the aqueous phase was removed. This procedure was repeated until the aqueous phase was colorless, which is usually three to four washings. The organic phase was washed with 1 L of 4 M HCl for 30 minutes (pH preferably <1) and removed. Sodium bicarbonate saturated water (1 L) was added and stirred vigorously for 15 minutes (pH preferably >7). The aqueous phase was separated and removed.

To the vigorously stirring 5-decenyl acetate solution was added 400 g of anhydrous sodium sulfate. After two hours of stirring, 400 g of potassium carbonate was added and the flask was stirred for 10 to 12 hours at about 55° C.

After 12 hours, the stirring was stopped and the 5-decenyl acetate mixture was transferred to a phenolic lined 55 gallon drum and stabilized with 1 M KOH in IPA to make a 0.1% solution. When the drum was full, it was shipped to a vacuum distillation company for purification.

This catalyst removal procedure or silica gel column chromatography can be used to remove the metathesis catalyst from the 5-decene or 5-decenyl acetate reaction mixtures in either the small or large scale processes, as desirable. In general, the removal process for metathesis catalysts is preferably conducted at temperatures between about 18° C. and 200° C., more preferably between about 45° C. and 100° C., and most preferably between about 50° C. and 75° C.

Conversion to 5-Decenol

A portion of the 5-decenyl acetate can be removed and converted to the corresponding alcohol according to the following procedure and the scale can be adjusted as necessary. 15.0 g (67 mmol) of the 5-decenyl acetate, 35 mL of methanol and 34 mL of 2 M sodium hydroxide are added to a 250 mL round-bottomed flask. This mixture is stirred for three hours at room temperature. After three hours the hydrolysis is complete, 10 mL of hexane is then added and the solution is washed with 10 mL of 1 M HCl, 10 mL of $NaHCO_3$-saturated water and 10 mL of brine. The organic phase is dried with sodium sulfate and filtered, and the hexane is removed under reduced pressure to yield 9.4 g of 5-decenol. GC analysis shows the isometric ratio of the 5-decenol to be conserved.

Finally, PTB pheromone can be prepared by blending 9.4 g (60.2 mmol) of the 5-decenol and 79.5 g (402 mmol) of the 5-decenyl acetate to make an 83:17 molar mixture of the acetate and alcohol.

EXAMPLE 3

Synthesis of 5-Decenyl Acetate, Employing Catalyst 848

With reference again to FIG. 9A, 5-decene was produced as in Examples 1 or 2 above or with the substitution of Catalyst 848 (FIG. 5A) for Catalyst 823.

With reference again to FIG. 9B, to a 100 mL round bottomed flask containing a magnetic stirbar and a vacuum adapter was added 10 g (70.4 mmol) 5-hexenyl acetate and 30 g (214 mmol) 5-decene. The reaction was sparged with nitrogen for five minutes, then 20 mg (0.023 mmol) of Catalyst 848 was added and stirred under a 10 mmHg vacuum for 45 minutes.

The metathesis catalyst was removed as previously described to yield a clear liquid. GC analysis indicated a 78% conversion of 5-hexenyl acetate to 5-decenyl acetate and an 82:18 E:Z isomeric ratio.

EXAMPLE 4

Synthesis of 5-Decenyl Acetate, Employing Catalyst 848

Figure 11:
FIG. 11 shows a one step synthesis of 5-decenyl acetate, in which 1-hexene is cross-metathesized with 5-hexenyl acetate to yield an 80:20 to 84:16 trans:cis ratio of 5-decenyl acetate.

FIG. 11 shows a one step synthesis of 5-decenyl acetate in the presence of Catalyst 848 to yield an 80:20 to 84:16 trans:cis ratio of 5-decenyl acetate. With reference to FIG. 6, to a 100 mL round bottomed flask containing a magnetic stirbar and a reflux condenser was added 10 g (70.4 mmol) 5-hexenyl acetate and 17 g (210 mmol) 1-hexene. The reaction flask was sparged with nitrogen for five minutes, then 24 mg (0.028 mmol) of Catalyst 848 (instead of Catalyst 823) was added and stirred under a nitrogen atmosphere at room temperature for six to eight hours. Volatile gasses, including ethylene, were vented into the hood as the reaction proceeded.

The metathesis catalyst was removed to yield a clear liquid. In an exemplary run, the GC analysis indicated a 65% conversion of 5-hexenyl acetate to 5-decenyl acetate and an 78:22 E:Z isomeric ratio.

This synthesis eliminates the self metathesis reaction of 1-hexene to 5-decene, including the extra starting materials, large quantity of catalyst, and the extra reaction time. In addition, this reaction is feasible without vacuum, can be accomplished in less time than either one of the steps in Examples 1 or 2, and proportionally uses 100 times less catalyst than is used in either of those examples.

Alternative preferred embodiments include: 1) using alcohol protected 5-hexen-1-ol or derivatives thereof, such as but not limited to tetrahydropyranyl (THP) ethers, trimethylsilyl (TMS) ethers, or ethyl vinyl ether (EVE) ethers, or acetate, or benzoate and propionate esters, or other similar derivatives readily apparent to skilled practitioners); 2) running the cross-metathesis reaction under conditions that prevent the formation of the methylidene ruthenium complex (i.e., removing a volatile terminal olefin as it is formed) since preventing the formation of the methylidene ruthenium complex results in high conversion of starting materials to product; and 3) obtaining a high trans:cis isomeric ratio in the reaction by using the conditions described above.

Figure 12:
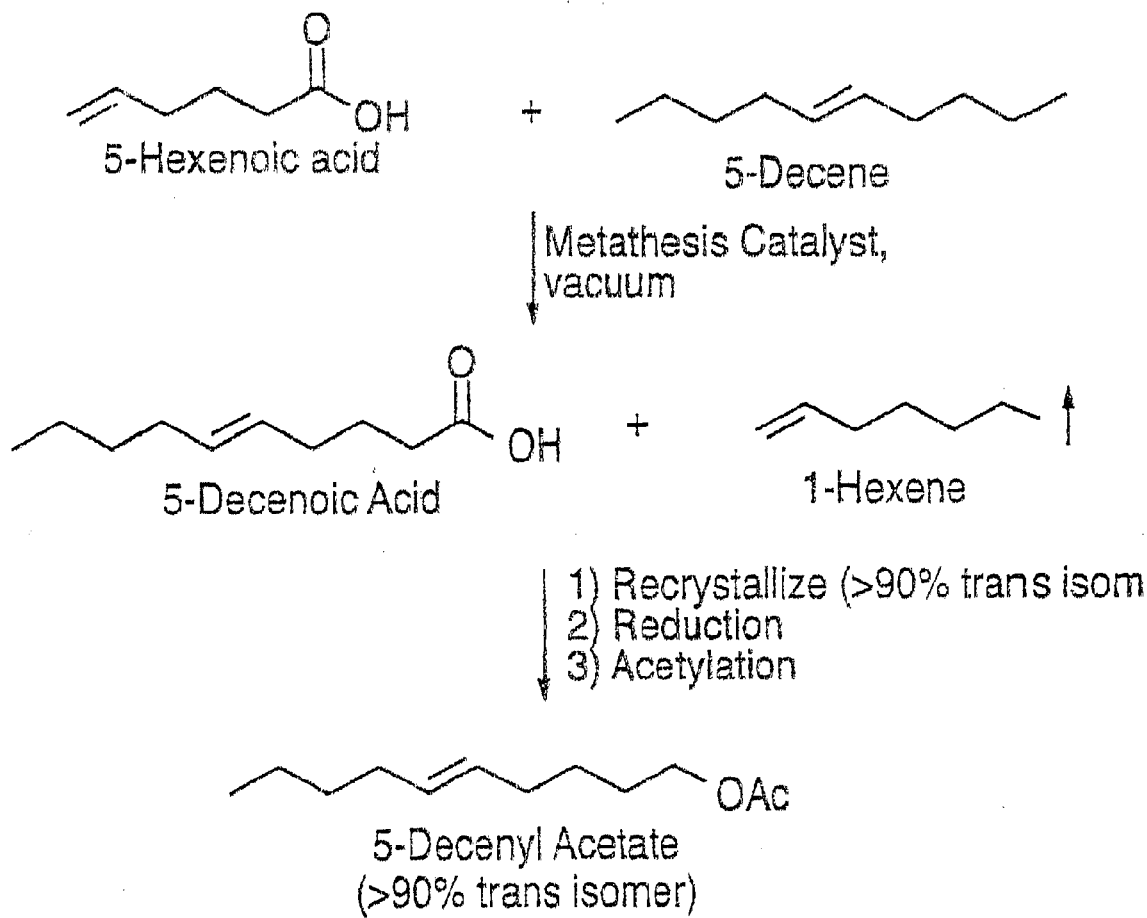
FIG. 12 shows an alternative synthesis of 5-decenyl acetate, in which 1-hexene is cross-metathesized with 5-hexenoic acid to produce 5-decenoic acid that can be recrystallized, reduced to an alcohol, and acetylated to yield a greater than 90% E-5-decenyl acetate.
Figure 13:
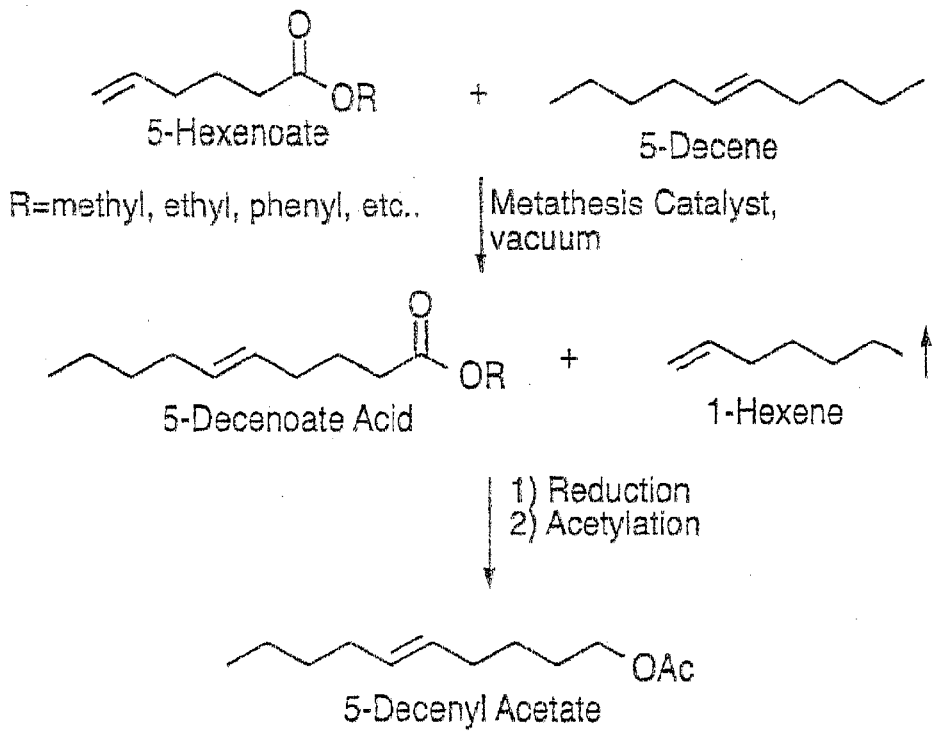
FIG. 13 shows an alternative synthesis of 5-decenyl acetate, in which 1-hexene is cross-metathesized with 5-hexenoate ester to produce 5-decenoic acid that can be recrystallized, reduced to an alcohol, and acetylated to yield a greater than 90% E-5-decenyl acetate.

For example, 5-hexenoic acid or an ester of 5-hexenoic acid (e.g. methyl 5-hexenoate, ethyl 5-hexenoate, etc . . . ) could be used instead of 1-hexene, but the synthesis would entail a reduction of a carboxylic acid or an ester to an alcohol followed by acetylation. These syntheses are respectively shown in FIGS. 12 and 13. With reference to FIGS. 12 and 13, the 5-hexenoic acid or 5-hexenoate is reacted with 5-decene to form 5-decenoic acid or 5-decenoate, respectively, in the presence of Catalyst 823 and under vacuum. The resulting 5-decenoic acid or 5-decenoate is reduced and acetylated to form 5-decenyl acetate. In addition, synthesizing 5-decenoic acid has advantages because the salt of 5-decenoic acid can be recrystallized to increase the trans-isomer to greater than 90 percent trans-5-decenoic acid, which is then reduced and acetylated to greater than 90 percent trans-5-decenyl acetate.

Figure 14:
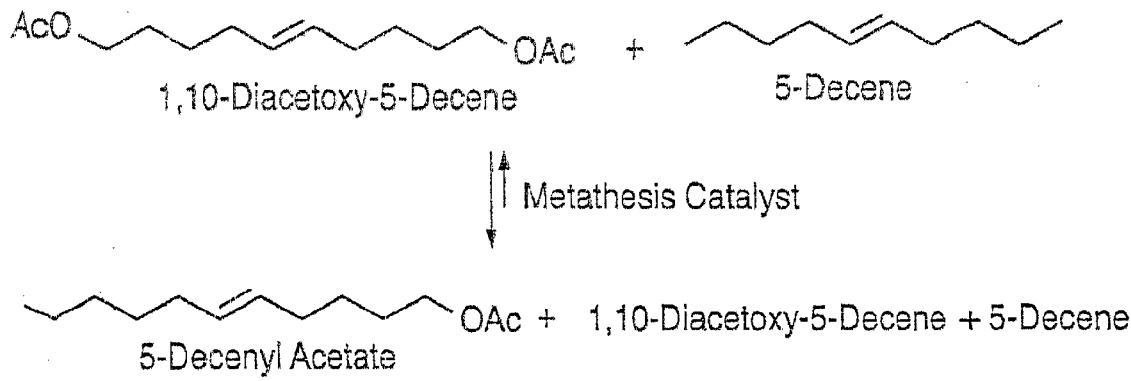
FIG. 14 shows an alternative synthesis of 5-decenyl acetate, in which 1,10-diacetoxy-5-decene and 5-decene are cross-metathesized.

FIG. 14 demonstrates another way to synthesize 5-decenyl acetate that entails the cross-metathesis of 1,10-diacetoxy-5-decene with 5-decene. If no terminal olefins are present (i.e. 1-hexene and 5-hexenyl acetate), the reaction will reach the same conversion and trans:cis ratio as the reactions described in Examples 1 and 2. The conversion of 5-hexenyl acetate to 1,10-diacetoxy-5-decene is preferably run under vacuum to remove ethylene and achieve high conversions (e.g. >98%). In some applications, it is economical when only 15% yields of value-added products are produced. The unreacted starting materials are recycled into another metathesis reaction.

Although the cross metathesis of a 1:1 ratio of 5-decene and 1,10-diacetoxy-5-decene statistically yields 25% 5-decene, 50% 5-decenyl acetate, and 25% 1,10-diacetoxy-5-decene, an advantage of this route is to obtain a maximum throughput of starting materials to product. The 5-decene and 1,10-diacetoxy-5-decene would be recycled back into the next cross-metathesis reaction.

Figure 15:
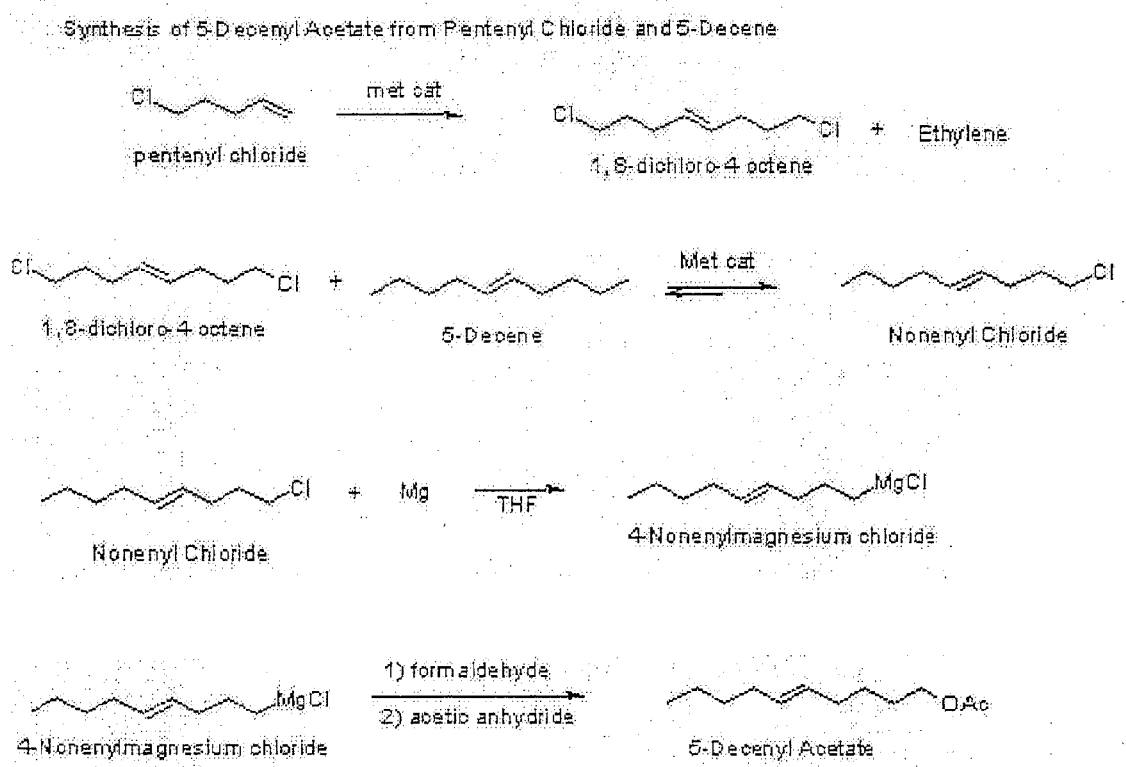
FIG. 15 shows an alternative synthesis of 5-decenyl acetate, in which 4-pentenyl chloride is self-metathesized to produce 1,8-dichloro-4-octene that is metathesized with 5-decene to produce 4-nonenyl chloride and then converted to 5-decenyl acetate.

FIG. 15 shows an alternative synthesis of 5-decenyl acetate, in which 4-pentenyl chloride is self-metathesized to produce 1,8-dichloro-4-octene, which is then metathesized with 5-decene to produce 8-nonenyl chloride. The nonenyl chloride is then converted to 5-decenyl acetate.

Cross-metathesis of Vinyl Borate Alkyl or Aryl Esters With Internal or Terminal Olefins The cross-metathesis of vinyl borate alkyl or aryl esters with internal or terminal olefins yields a synthetically valuable intermediate which is converted into trans- or cis-halovinyl intermediates, or into trans-olefins or cis-olefins through the coupling of the alkyl vinyl borates with palladium catalysts and organoalkyl or organoaryl reagents. This vinyl borate cross-metathesis procedure opens up many new opportunities because of its gentleness and cost-effectiveness.

Traditionally the synthesis of alkyl vinyl borate esters involves the conversion of a terminal olefin into the terminal acetylene by brominating with liquid bromine, followed by dehydrohalogenation with sodium amide in liquid ammonia. Then adding an expensive borane reagent (e.g. 9-BBN, catechol borane, pinacol borane, etc.) to yield the predominately trans vinyl borate intermediate. These reactions steps are not amendable to many functional groups or to other olefins within the molecule. This synthetic route is expensive process and makes many desirable products economically unattractive.

This invention, however, not only provides for the cross-metathesis of an internal olefin (i.e. 5-decene) with vinyl borate yields cis and trans hexenyl borates, but also provides for the separation of the cis and trans hexenyl borates by simple vacuum distillation or by column chromatography to yield the pure cis and trans isomers. Once a pure borate isomer is obtained, it can be converted into iodo-vinyl intermediate with retention of configuration, or bromo-vinyl intermediate with inversion of configuration (i.e. trans hexenyl borate pinacol ester can be converted into trans 1-iodo-1-hexene or cis 1-bromo-hexene, depending on the reaction conditions. Then, the trans 1-iodo-1-hexene or cis 1-bromo-hexene can be coupled with various organometallic alkyl or organometallic aryl reagents to yield isomerically pure products. This technique complements and competes directly with Wittig and Horner Emmons chemistries.

The traditional method to separate cis and trans olefins is to use silver nitrate impregnated silica gel. This technique works well for small research quantities of material (i.e. <100 mg), but it is too expensive and cumbersome to be practical at large scale (>10 Kg). The advantage of easily separating cis and trans-alkyl vinyl borates by simple vacuum distillation, column chromatography, or recrystallization makes this technique very powerful and efficient. Furthermore, cross-metathesis of vinyl borates with cis and trans 5-decene selectively depletes the cis-5-decene, even in the presence of a large excess of the trans-5-decene isomer.

Tables VII and VIII present the results from a cross-metathesis reaction under different reactions conditions. These results demonstrate the utility and selectiveness of this technique.

TABLE VII

Cross-Metathesis Vinyl Borate Pinacol Ester with 5-Decene (1:107:666 mole ratio of catalyst 823:vinyl borate pinacol ester:5-decene, run at 45° C.)

| Time (min) | % E-5-Decene | % E-HBPE | % Yield of HBPE |
| --- | --- | --- | --- |
| 0 | 82.3 | — | 0 |
| 1 | 84.1 | 94.0 | 22.0 |
| 2 | 84.4 | 93.3 | 34.5 |
| 3 | 84.7 | 93.0 | 42.5 |
| 4 | | | |
| 5 | 85.0 | 92.5 | 52.5 |
| 7 | 85.3 | 92.2 | 60.0 |
| 8 | | | |
| 9 | 85.7 | 92.1 | 63.8 |
| 10 | | | |
| 11 | | | |
| 12 | 85.9 | 91.8 | 68.4 |
| 13 | | | |
| 14 | | | |
| 15 | 86.1 | 91.6 | 73.2 |
| 16 | | | |
| 17 | | | |
| 18 | | | |
| 19 | | | |
| 20 | 86.1 | 90.6 | 76.2 |
| 22 | | | |
| 23 | | | |
| 24 | | | |
| 25 | 86.5 | 91.4 | 78.0 |
| 9 hours | 86.7 | 89.8 | >99 |

5-Decene started as an 82.3% trans to 17.7% cis isomeric mixture.
HBPE = hexenyl borate pinacol ester

TABLE VIII

Cross-Metathesis Vinyl Borate Pinacol Ester with 5-Decene (1:107:214 mole ratio of catalyst 823:5-decene: vinyl borate pinacol ester), run at 44° C.)

| Time (min) | % E-5-Decene | % E-HBPE | % Yield of HBPE |
| --- | --- | --- | --- |
| 0 | 82.3 | — | 0 |
| 1 | 84.8 | 91.8 | 5.0 |
| 2 | | | |
| 3 | 84.5 | 91.5 | 5.9 |
| 4 | | | |
| 5 | | | |
| 6 | | | |
| 7 | | | |
| 8 | | | |
| 9 | 86.2 | 91.4 | 7.8 |
| 10 | | | |
| 12 | | | |
| 13 | | | |
| 14 | | | |
| 15 | — | 91.2 | 9.3 |
| 16 | | | |
| 17 | | | |
| 18 | | | |
| 19 | | | |
| 20 | 85.4 | 91.1 | 10.3 |
| 21 | | | |
| 22 | | | |
| 23 | | | |
| 24 | | | |
| 25 | 85.4 | 91.1 | 11.1 |
| 10 hours | 87.3 | 90.7 | 20.0 |

5-Decene started as an 82.3% trans to 17.7% cis isomeric mixture.
HBPE = hexenyl borate pinacol ester In Table VII, the cross metathesis reaction proceeded quickly to completion, and it increases the trans ratio of 5-decene from 82.3% to 86.7% even though a 600% excess of 5-decene was used. Also the isomeric ratio of the hexenyl borate pinacol ester retains the high trans selectivity, starting at 94% after 1 minute to 90% after 9 hrs.

In Table VIII, when vinyl borate pinacol ester is used in excess, the reaction is slow and the yield of hexenyl borate pinacol ester (HBPE) is low (i.e. 20.0%). However, the E-5-decene isomer purity and the isomeric purity of HBPE reach approximately the same value as when 5-decene was used in a large excess (Table VII, 9 hour data).

Figure 16:
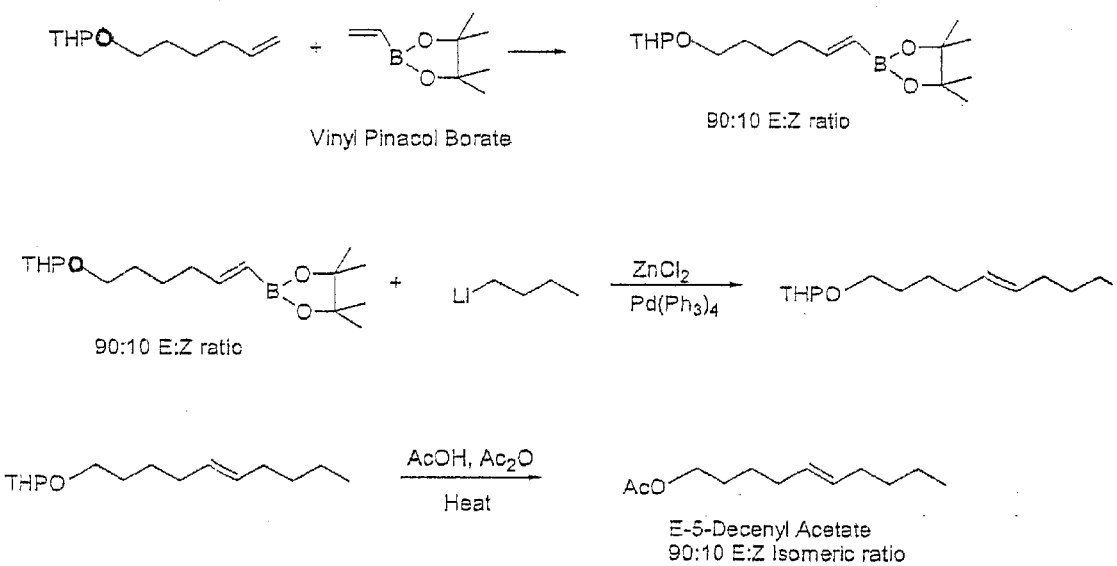
FIG. 16 shows an alternative synthesis of 5-decenyl acetate, in which vinyl borate pinacol ester is crossmetathesized with 5-hexenol THP ether to yield a pinacol ester of 1-borohexen-6-ol THP ether.

FIG. 16 shows a synthesis of 5-decenyl acetate which involves the cross-metathesis of vinyl borate pinacol ester (Matheson, D. S *J Am Chem Soc* (1960) 82, 4228–4233) with 5-hexenol THP ether (or 1,10-diTHP ether of 5-decene) with Catalyst 823 to yield a pinacol ester of 1-borohexen-6-ol THP ether. This product was coupled with butyl lithium and zinc chloride under Suzuki conditions as described by Miycuira (*Org Syn* VIII p 532) to yield E-5-decenol THP ether in a 91:9 E:Z isomeric ratio. This material was purified by column chromatography and then acetated to yield 5-decenyl acetate in 91:9 E:Z isomeric ratio.

Figure 17:
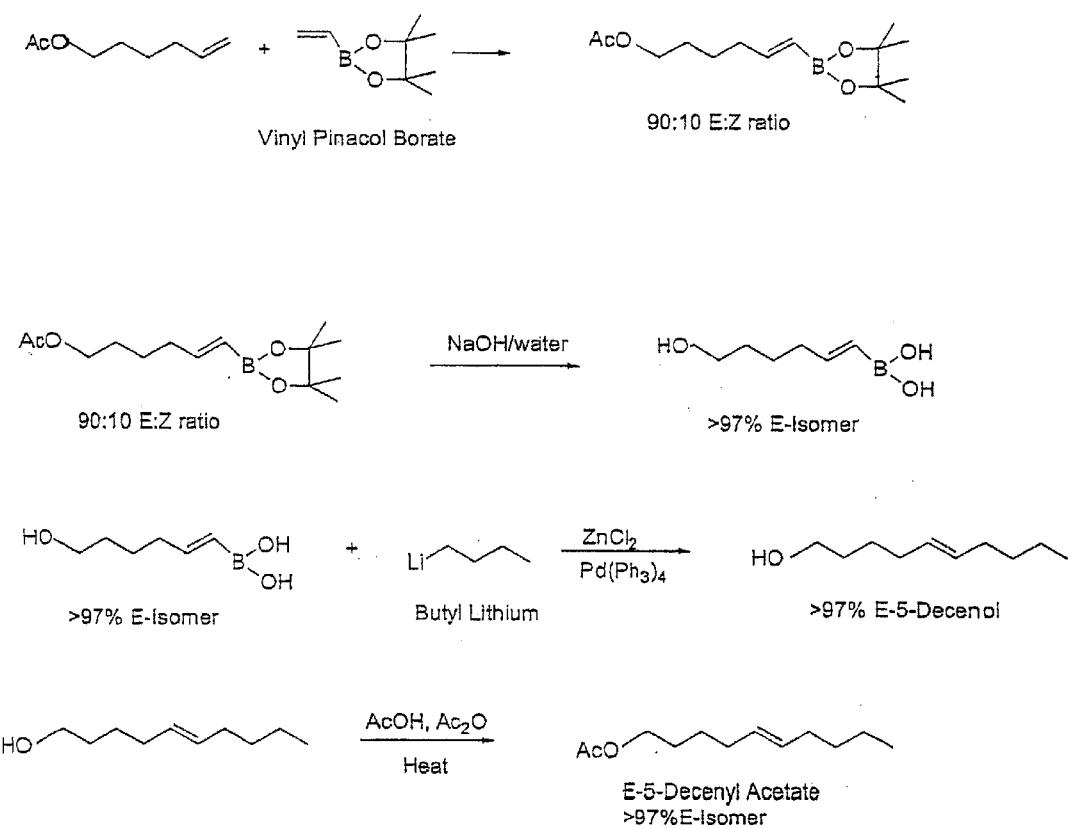
FIG. 17 shows alternative synthesis of 5-decenyl acetate, in which vinyl borate pinacol ester is cross-metathesized with 5-hexenyl acetate to yield a pinacol ester of 1-borohexen-6-yl acetate, which is crystallized from sodium hydroxide and water to yield 1-boronic acid of hexen-6-ol, followed by conversion to >97% E-5-decenyl acetate.

FIG. 17 shows a synthesis of 5-decenyl acetate which involves the cross-metathesis of vinyl borate pinacol ester (Matheson, D. S *J Am Chem Soc* (1960) 82, 4228–4233) with 5-hexenyl acetate (or 1,10-diacetoxy-5-decene) with Catalyst 823 to yield a pinacol ester of 1-borohexen-6-yl acetate. This product was crystallized from sodium hydroxide and water to yield a 1-boronic acid of hexen-6-ol. This product was coupled with butyl lithium and zinc chloride under Suzuki conditions as described by Miycuira (*Org Syn* VIII p 532) to yield E-5-decenol in a >98% E isomeric ratio. This material was purified by column chromatography, acetated to yield 5-decenyl acetate in >98% isomeric ratio.

Figure 18:
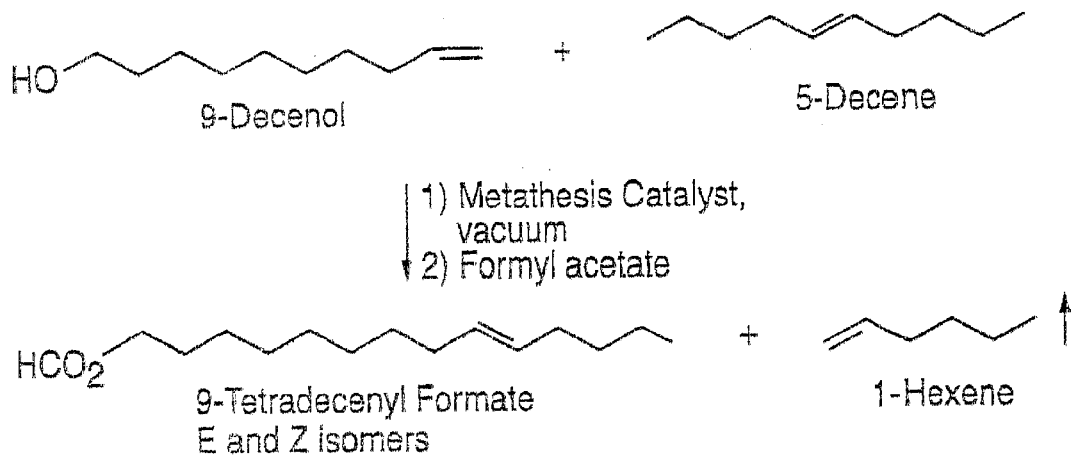
FIG. 18 shows a synthesis of 9-tetradecenyl formate, in which 5-decene is cross-metathesized with 9-decenol to produce 9-tetradecenol while 1-hexene is removed from the reaction under vacuum, and in which the metathesis product, 9-tetradecenol, is reacted with formyl acetate.

FIG. 18 shows a synthesis of 9-tetradecenyl formate, which is an analog of the Diamondback Moth (DBM) pheromone. With reference again to FIG. 9A, 5-decene was produced as in Examples 1 or 2 above or with the substitution of Catalyst 848 for Catalyst 823. With reference to FIG. 18, 5-decene is cross-metathesized with 9-decenol under vacuum and in the presence of Catalyst 823 to produce 9-tetradecenol (not shown) while 1-hexene is removed from the reaction as it is generated. Then, formyl acetate is reacted with the 9-tetradecenol to produce the 9-tetradecenyl formate.

EXAMPLE 6

Synthesis of 11-Tetradecenyl Acetate

Figure 19:
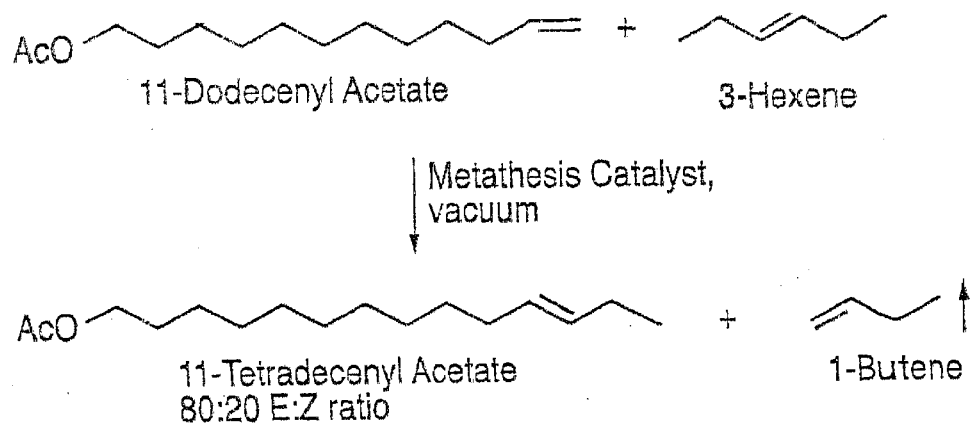
FIG. 19 shows a synthesis of 11-tetradecenyl acetate, in which 3-hexene is cross-metathesized with 11-dodecenyl acetate so that 1-butene is removed from solution as it is generated.

FIG. 19 shows a synthesis of 11-tetradecenyl acetate, which is the pheromone of the Omnivorous Leafroller (OLR). With reference to FIG. 19, to a 100 mL round bottomed flask containing a magnetic stirbar and a reflux condenser was added 10 g (44.2 mmol) 11-dodecenyl acetate and 11.2 g (133 mmol) 3-hexene. The reaction was sparged with nitrogen for 5 minutes, then 12 mg (0.014 mmol) of Catalyst 848 was added and stirred under a nitrogen atmosphere at room temp for eight hours. Volatile gasses, including 1-butene, were vented into the hood as the reaction proceeded.

The metathesis catalyst was removed, as previously described, to yield a clear liquid. GC analysis indicated a 70% conversion of 11-dodecenyl acetate to 11-tetradecenyl acetate and an 80:20 E:Z isomeric ratio.

EXAMPLE 7

Synthesis of 11-Tetradecenyl Acetate

With reference again to FIG. 19, to a 100 mL round bottomed flask in a −15° C. cooling bath, containing a magnetic stirbar and a dry ice condenser was added 10 g (44.2 mmol) 11-dodecenyl acetate and 15 g (268 mmol) 1-butene instead of 3-hexene. The reaction was sparged with nitrogen for one minute, then 24 mg (0.028 mmol) of Catalyst 848 was added and stirred under a nitrogen atmosphere at 15° C. for eight hours, then allowed to warm to room temp overnight. Volatile gasses, including 1-butene, were vented into a hood as the reaction proceeded.

The metathesis catalyst was removed, as previously described, to yield a clear liquid, GC analysis indicated a 55% conversion of 11-dodecenyl acetate to 11-tetradecenyl acetate and an 66:34 E:Z isomeric ratio.

EXAMPLE 7a

Synthesis of 11-Tetradecenyl Acetate

With reference to FIG. 20, to a 100 mL round bottomed flask containing a magnetic stirbar and a reflux condenser was added 10 g (31.2 mmol) 11-eicosenyl acetate and 15 g (179 mmol) 3-hexene. 11-Eicosenyl acetate is isolated from an inexpensive commodity seed oil known as jojoba oil. The reaction was sparged with nitrogen for 1 minute, then 50 mg (0.059 mmol) of Catalyst 848 was added and stirred under a nitrogen atmosphere at 35° C. for eight hours.

The metathesis catalyst was removed, as previously described, to yield a clear liquid, GC analysis indicated a 69% conversion of 11-eicosenyl acetate to 11-tetradecenyl acetate and an 83:17 E:Z isomeric ratio. 11-Tetradecenyl acetate was isolated by column chromatography using cyclohexane as the solvent to yield 3.86 g (15.1 mmol), 48% yield.

Figure 21:
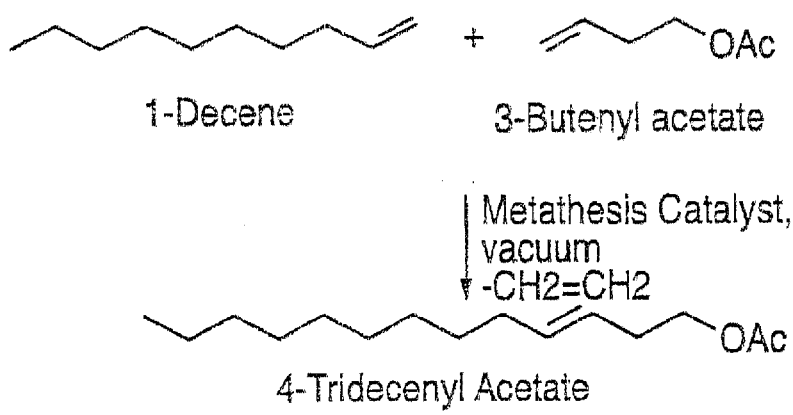
FIG. 21 shows a synthesis of E-4-tridecenyl acetate, in which 1-decene is cross-metathesized with 4-pentenyl acetate so that ethylene is removed from solution as it is generated.

FIG. 21 shows a synthesis of E-4-tridecenyl acetate, which is the major component of the Tomato Pinworm (TPW) pheromone. With reference to FIG. 12, 1-decene is cross-metathesized with 4-pentenyl acetate in the presence of Catalyst 823 under vacuum so that E-4-tridecenyl acetate is produced and ethylene is removed from solution as it is generated.

Figure 22:
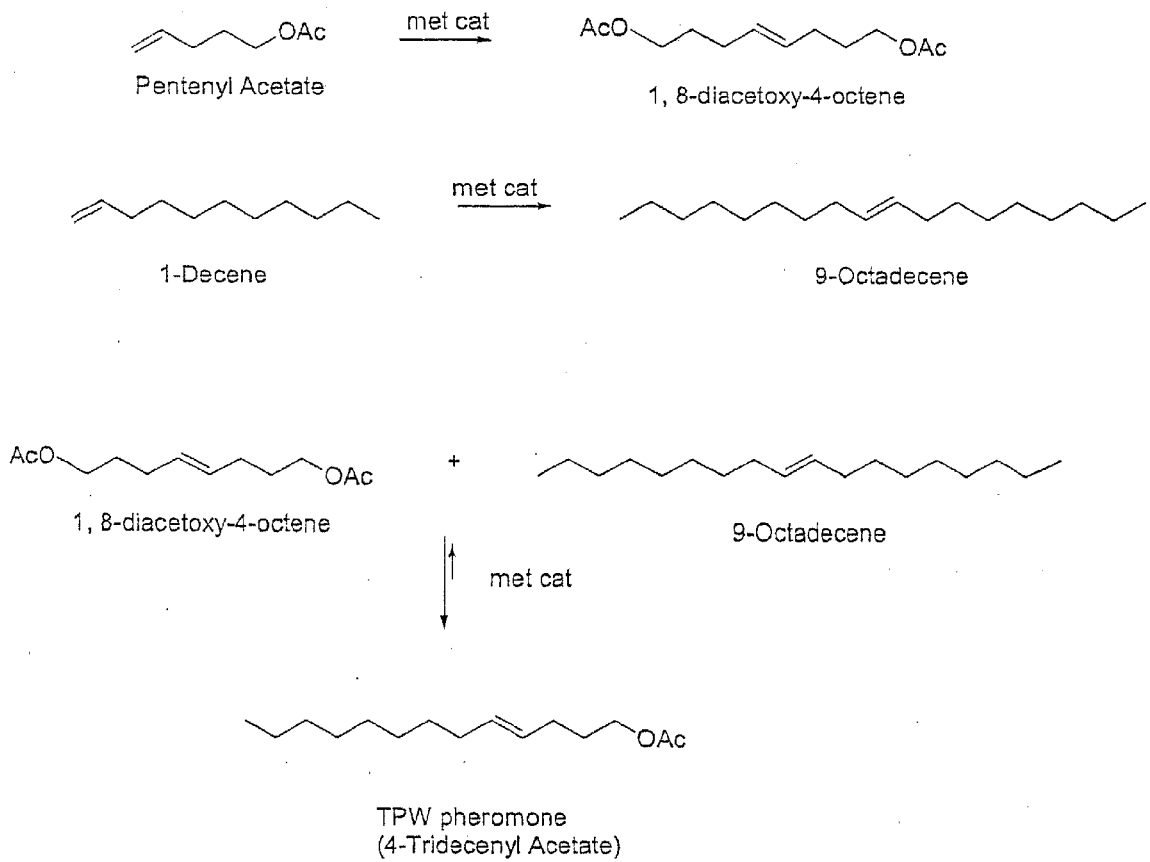
FIG. 22 shows an alternative synthesis of E-4-tridecenyl acetate, in which 1-decene is self-metathesized to form 9-octadecene, 4-pentenyl acetate is self-metathesized to yield 1,8-diacetoxy-4-octene, and 9-octadecene is crossmetathesized with 1,8-diacetoxy-4-octene.

FIG. 22 shows another synthesis of E-4-tridecenyl acetate. With reference to FIG. 22, 1-decene is self metathesized with itself to form 9-octadecene. 4-Pentyl acetate is self-metathesized to yield 1,8-diacetoxy-4-octene. The cross-metathesis of 9-octadecene and 1,8-diacetoxy-4-octene in the presence of Catalyst 823, without vacuum, yields 4-tridecenyl acetate. The use of two internal olefins permits high conversions and yields of 4-tetradecenyl acetate to be obtained without vacuum.

Figure 23:
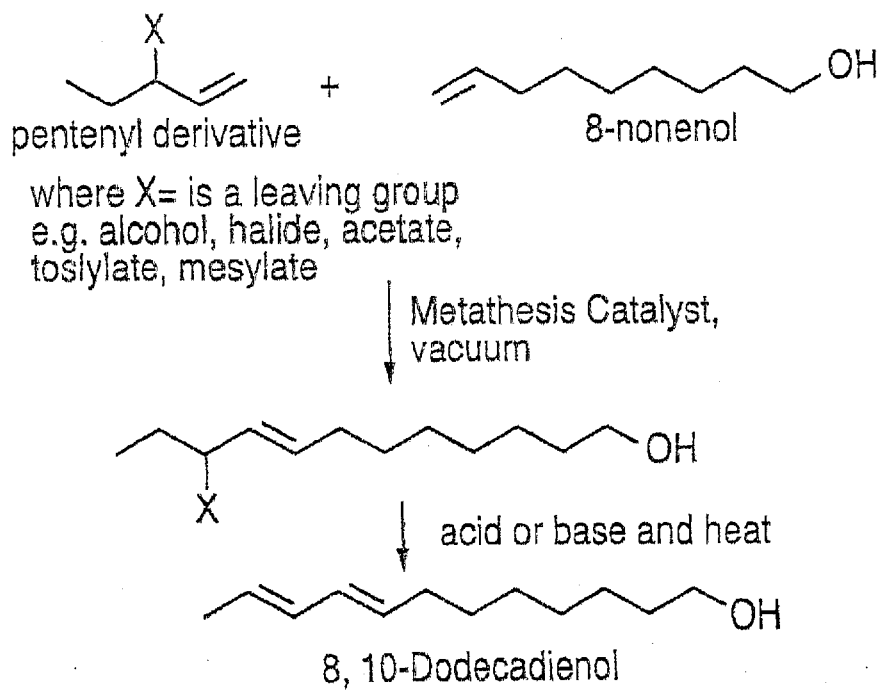
FIG. 23 shows a synthesis of E,E-8,10-dodecadienol, in which a pentenyl derivative is cross-metathesized with 8-nonenol and then treated with an acid or base.

FIG. 23 shows a synthesis of E,E-8,10-dodecadienol, which is the pheromone of the Codling Moth (CM). With reference to FIG. 23, a pentenyl derivative is cross-metathesized with 8-nonenol in the presence of Catalyst 823 under vacuum to produce an E-8-dodecenyl derivative with a leaving group designated by X at the C-position. Ethylene is removed from the reaction mixture as it is generated. The reaction mixture is then treated with an acid or base to yield E,E-8,10-dodecadienol.

Figure 24A:
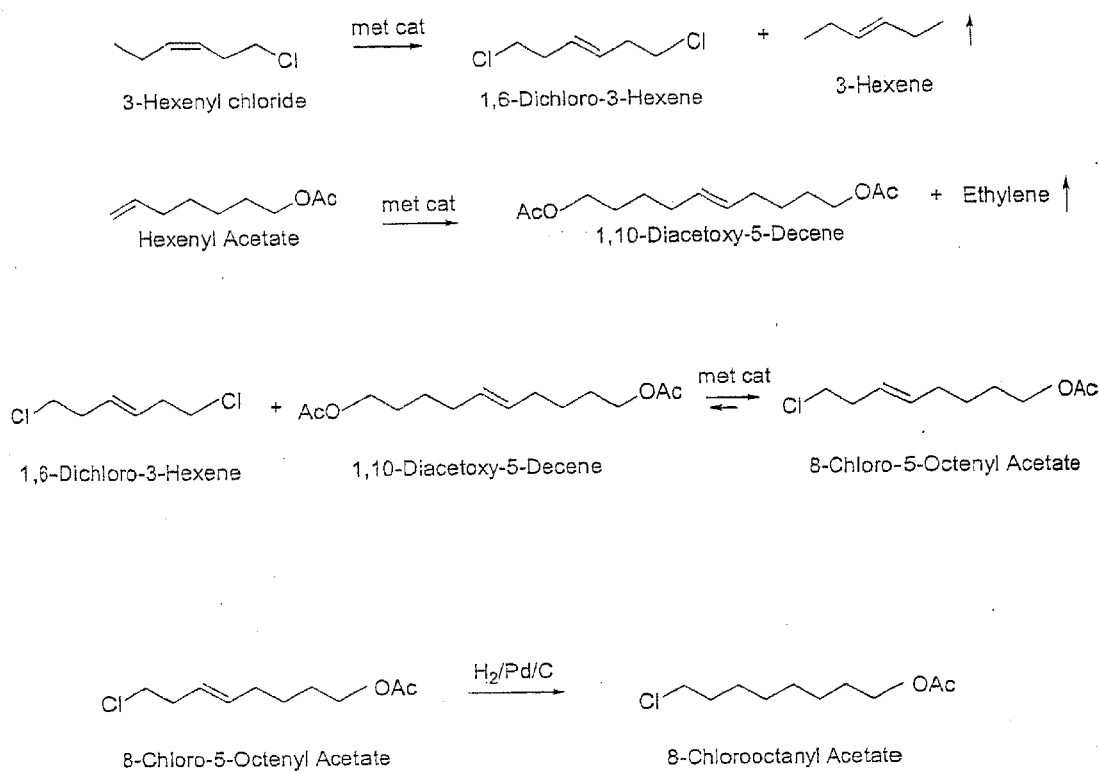
FIG. 24A shows a synthesis of 8-chlorooctan-1-yl acetate, in which 1,10-diacetoxy-5-decene is cross-metathesized with 1,6-dichloro-3-hexene to yield 8-chloro-5-octen-1-yl acetate, which is reduced to yield 8-chlorooctanyl acetate.
Figure 24B:
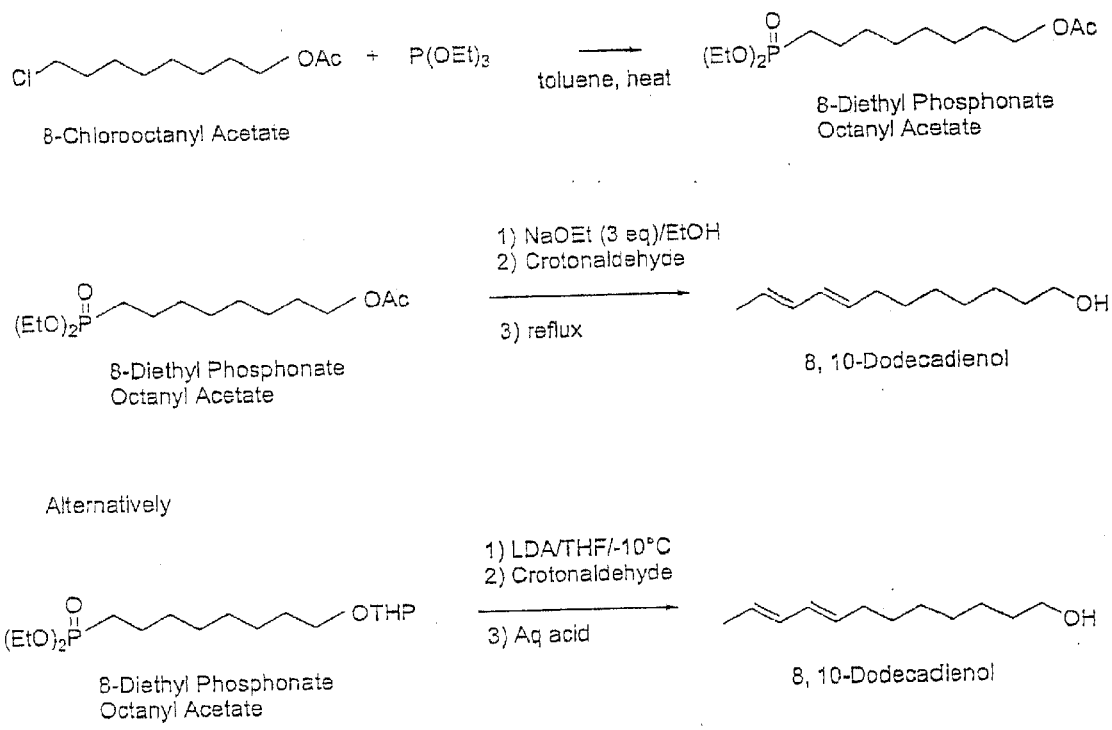
FIG. 24B shows an alternative synthesis of E,E-8,10-dodecadienol, in which 8-chlorooctan-1-yl acetate is refluxed with of triethyl phosphite in toluene to yield 8-diethyl phosphonate octanyl acetate, followed by conversion into 8,10-dodecadienol.

FIGS. 24A and 24B show another synthesis of E,E-8,10-dodecadienol. With reference to FIG. 24A, 8-chlorooctan-1-yl acetate was synthesized from the cross metathesis of 1,10-diacetoxy-5-decene and 1,6-dichloro-3-hexene with Catalyst 801 to yield 8-chloro-5-octen-1-yl acetate, which was reduced and deacetylated. With reference to FIG. 24B, 8-chlorooctan-1-yl acetate was refluxed with two equivalents of triethyl phosphite in toluene for four hours to yield the octanol phosphonate intermediate. The mixture was cooled to −40° C. under argon. Lithium diisopropyl amine was added (2.3 mol equivalents to the phosphonate) and slowly warmed to room temp. Freshly distilled crotonaldehyde (2 mol equivalents) was added and stirred at room temp for 4 hours. The mixture was worked up to yield 8,10-dodecadienol.

Advantages of Metathesis Routes Into 8-Halooctan-1-ols Compared to Traditional Methods to 8-Halooctan-1-ols Omega-haloalkanols are valuable compounds that have been used as synthetic intermediates, especially in the synthesis of insect pheromones (Mori 1992). Traditional methods for preparing these compounds is by heating alpha, omega-diols with aqueous HCl or HBr in an inert solvent with continuous (Pattison, F L M; J B Sothers; R G Woolford *J. Am. Chem. Soc.* (1956) 78, 2255–2259) or without continuous (Chong, J M; M A Heuft; and P Rabbat "Solvent Effects on the Monobromination of alpha, omega-Diols: A Convenient Preparation of omega-Bromoalkanols" *J. Org. Chem.* (2000) 65, 5837–5838) removal of water. These methods work reasonably well for research amounts of materials but are inconvenient for large-scale syntheses. However, these reactions are generally run dilute (e.g. 0.3 M), require up to 96 hours to obtain high conversions, are contaminated with up to 60% of di-halides or unreacted starting diols, do not readily permit isolation of the pure omega-haloalkanol by distillation, and afford modest yields (typically 35% to 85%). Another limitation is that some of the diols are prohibitively expensive to use in a commercial process.

A new process that overcomes these shortfalls employs the cross-metathesis of alpha-omega-diacetoxy alkenes and alpha-omega-dihalides to yield omega-haloalkenols. (The nomenclature herein refers to omega representing the last carbon atom in the molecule, starting with the alcohol as the first carbon atom.) Omega-haloalkenols are valuable synthetic intermediates on their own and they are easily converted into omega-haloalkanols under traditional hydrogenation methods. The advantages of this method are four different symmetrical alpha, omega-dihalides (i.e. W—(CH2)$_n$—W, where W is selected from chloride, bromide, iodide, mesylate, tosylate or derivatixes thereof, and n equals 4, 6, 8 or 10) can be crossed with 4 different symmetrical alpha, omega-diacetoxyalkenes (i.e. AcO—(CH2)n-OAc where n=4, 6, 8 or 10) to yield 7 different omega-haloalkenols (i.e. AcO—(CH2)nCH=CH(CH2)m-W where n=1, 2, 3, or 4 and m=1, 2, 3, or 4). These omega-haloalkenols are converted to omega-haloalkanols under hydrogenation conditions.

These metathesis reactions are run neat, usually in equal molar ratios of symmetrical dihalides and diacetoxy compounds, and the unreacted starting materials are recycled back into the next metathesis reaction. The yields are typically around 50% reactor volume efficiencies (i.e. 50% of the reactor's volume is product). The starting symmetrical dihalides and diacetoxy compounds are generally available from commercial sources or by easy conversions of alcohols to halides. They are also preferably selected to afford the greatest ease of isolating the omega-haloalkenol from the starting materials, such as by selecting the stating materials based on the differences between their boiling points and that of the omega-haloalkenol product. For example, in the cross-metathesis reaction between 1,6-dibromo-3-hexene and 1,10-diacetoxy-5-decene to yield 8-bromo-5-octenyl acetate, these starting materials were choosen because of the large differences in their boiling points: 1,6-dibromo-3-hexene Bpt$_{1.0}$ mmHg 84°–85° C., 8-bromo-5-octenyl acetate Bpt$_{1.0}$ mmHg 110° C.–112° C. and 1,10-diacetoxy-5-decene Bpt$_{1.0}$ mmHg 158° C.–162° C.

Example: Comparison Synthesis of 8-Bromooctan-1-ol

8-Bromooctan-1-ol is a valuable starting material in the synthesis of insect pheromones, but it is not widely used because it is not commercially available in large quantities. TCI (Portland Oreg.) sells 8-bromooctan-1-ol at 25 g for $191.30 ($7,652/Kg). Starting from 1,8-octanediol is also expensive; TCI sells 1,8-octanediol for $498/Kg. This expense and the shortcomings presented above in converting this material into omega-alkanol make such a method commercially unviable.

Figure 25:
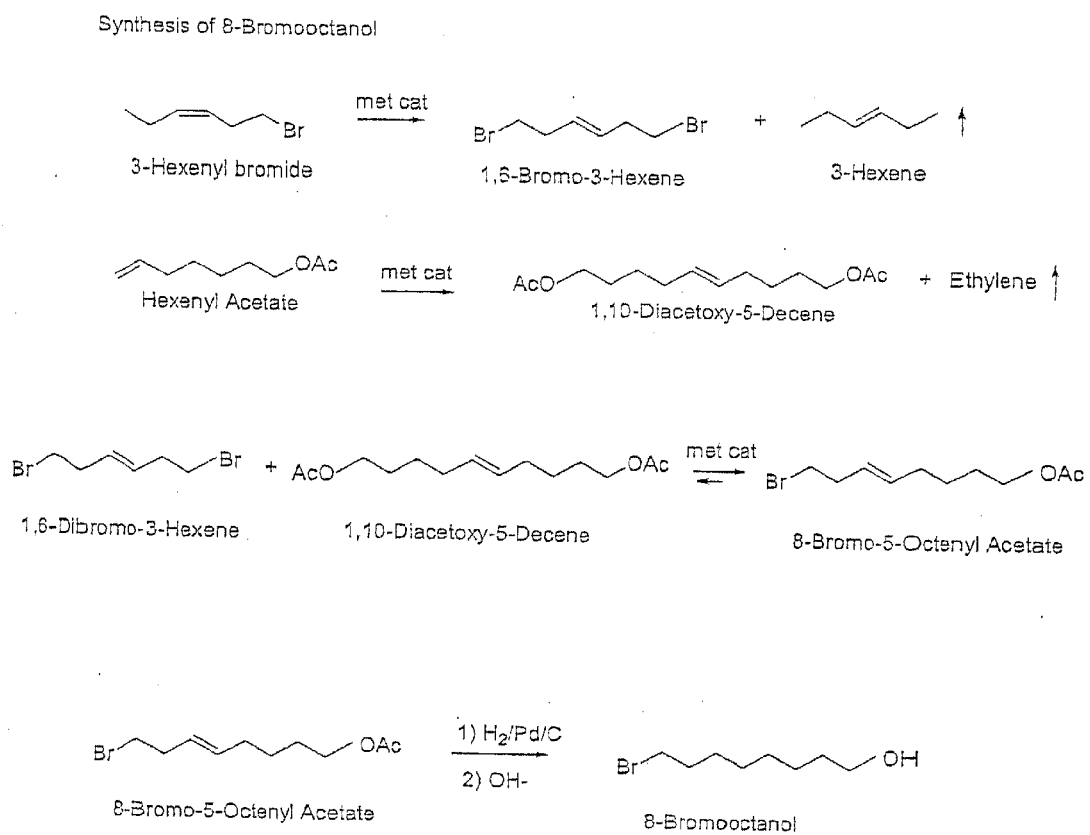
FIG. 25 shows the synthesis of 8-bromoocatanol from the cross-metathesis of 1,6-dibromo-3-hexene and 1,10-diacetoxy-5-decene.

With reference to FIG. 25, olefin metathesis provides, however, an affordable method to produce 8-bromooctan-1-ol. The symmetrical 1,6 dibromo-3-hexene is made by the cross-metathesis of 1-bromo-3-hexene (removing the volatile 3-hexene under vacuum). 1-Bromo-3-hexene is prepared from commercially available leaf alcohol (Bedoukian, Danbury Conn.) that sells for approximately $50 U.S./Kg, and 1,10-diacetoxy-5-decene is prepared by the cross-metathesis of hexenyl acetate. Hexenyl acetate is prepared from hexenol by conventional methods. 5-Hexenol sells for approximately $50 U.S./Kg and is available from Degussa-Huls, Somerset, N.J.

Equal molar ratios of neat 1,6 dibromo-3-hexene and 1,10-diacetoxy-5-decene are cross metathesized to yield 40% to 50% yields of 8-bromo-5-octenyl acetate (the maximum yield under these reaction conditions is 50% yields). Omega-bromo-5-octenyl acetate is isolated by a simple vacuum distillation and reduced and deacetylated to produce 8-bromooctan-1-ol. The cost of this process is <$300 U.S./Kg of final product.

Syntheses of Mosquito Oviposition Attractant Pheromone (MOP): (5R,6S)-6-Acetoxy-5-Hexadecanolide

EXAMPLE 8

Cross Metathesis of Meadowfoam Oil and 1-Dodecene

Figure 26:
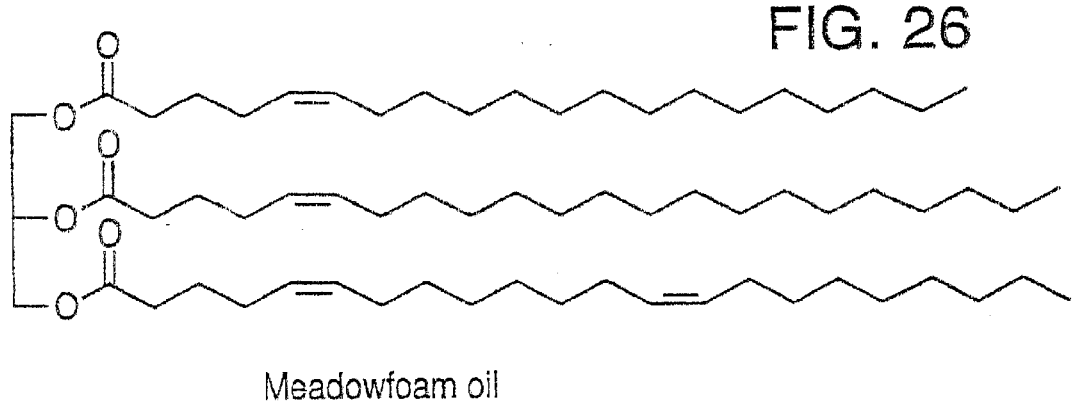
FIG. 26 shows a chemical diagram of meadowfoam oil.

FIG. 26 shows a chemical structure of meadowfoam oil, which is also known by its botanical name Limnanthes Alba (CAS Number: 153065-40-8; EINES Number: 310-127-6). Meadowfoam oil is commercially available from Natural Plant Products LLC, 2767 19th St SE, PO Box 4306, Salem, Oreg. 97302, and currently costs about $12 per kilogram.

Figure 27:
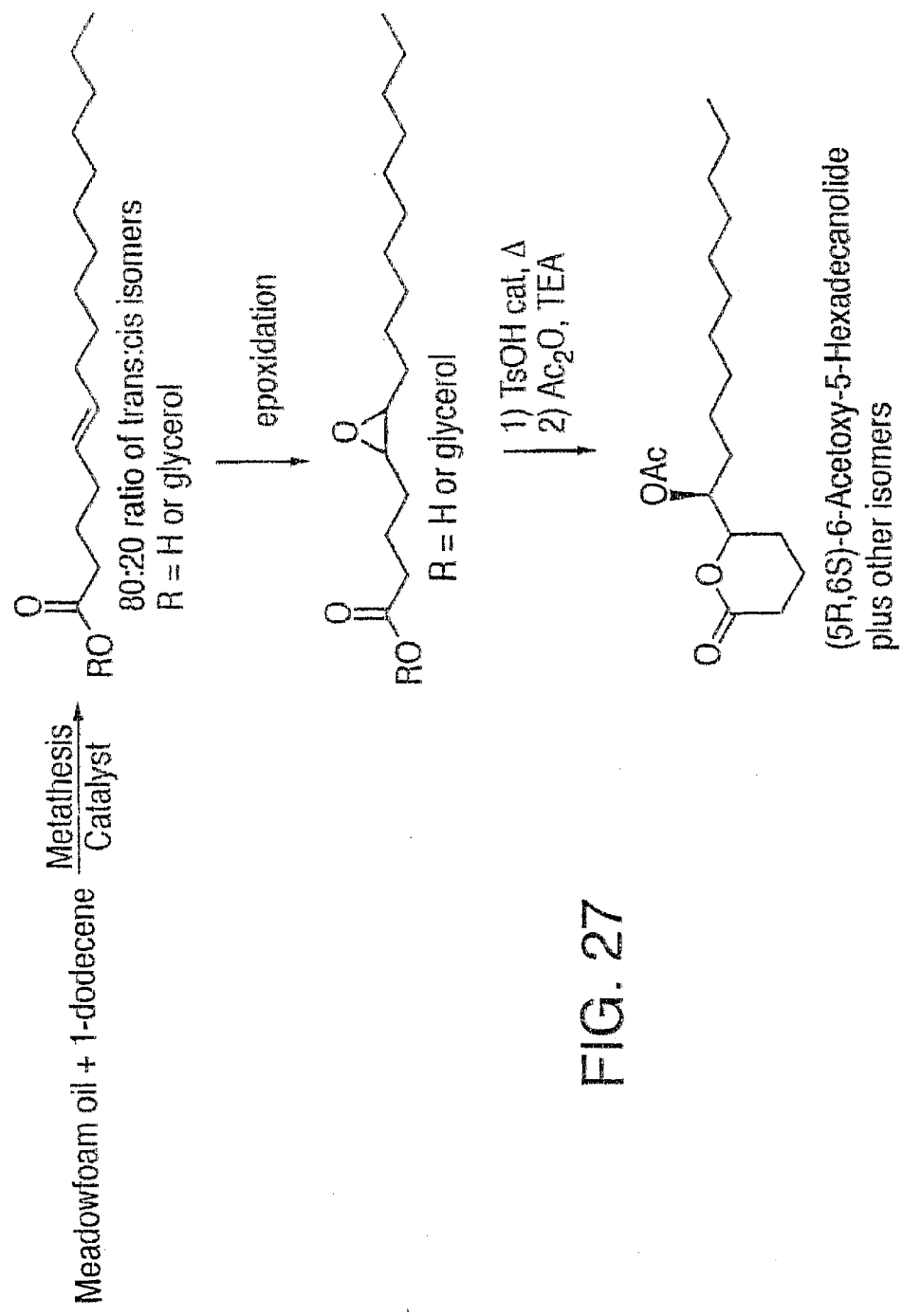
FIG. 27 shows a synthesis of mosquito oviposition pheromone involving the cross-metathesis of meadowfoam oil and 1-dodecene.

FIG. 27 shows a synthetic scheme for MOP employing the cross-metathesis of meadowfoam oil and 1-dodecene. With reference to FIGS. 26 and 27, to a dry 50 mL round bottomed flask was added 3.0 g (3.0 mmol) meadowfoam oil and 6.1 g (36 mmol) 1-dodecene. The flask was purged with nitrogen for 20 minutes, followed by the addition of 0.025 g (0.030 mmol) Catalyst 823 and the mixture was stirred at 35° C. for 18 hours, under a 10 mmHg vacuum. The metathesis catalyst was removed by the addition of 0.037 g (0.30 mmol) of trishydroxymethyl phosphine and 5 mL of triethylamine. The mixture was stirred at 50° C. for 12 hours. Three 100 mL washes with water were performed, followed by 1×50 mL wash with 1 M HCl and 1×50 mL wash with NaHCO$_3$ saturated water. The organic phase was dried with anhydrous sodium sulfate, filtered and used in the next reaction without further purification.

The metathesis product from above was oxidized to the epoxide as described by Bach et al. in "Epoxidation of Olefins by Hydrogen peroxide-Acetonitrile: cis- Cyclohexene Oxide", Organic synthesis collective Volume Vii, 1990, p. 126 or with m-chloroperoxybenzoic acid. The glyceride esters were hydrolyzed and the epoxide opened to the diol by warming the epoxide in 2 M KOH and 20 mL of isopropyl alcohol (IPA) to 60° C. for six hours. The solution was concentrated and washed with 50 mL of 1 M HCl. The organic phase was dried with anhydrous sodium sulfate, filtered and used in the next reaction without further purification. Lactonization was accomplished using the following procedure: the crude diol (2.9 g, 9.0 mmol) was dissolved into 50 mL of anhydrous toluene containing 50 mg of toluenesulfonic acid and heated to 100° C. for six hours. The mixture was cooled to room temp and washed with 50 mL of $NaHCO_3$ saturated water. The organic phase was dried with anhydrous sodium sulfate, filtered and used in the next reaction without further purification. The dried solution was acetylated with 1.8 g (0.018 mmol) acetic anhydride and 5 mL of triethylamine. The solution was stirred at room temp overnight. The reaction was worked up by washing with 50 mL of 1 M HCl and 50 mL wash of $NaHCO_3$ saturated water. The organic phase was dried with anhydrous sodium sulfate, filtered, concentrated and to yield (5R,6S)-6-acetoxy-5-hexadecanolide and its stereoisomers, and then purified by column chromatography.

EXAMPLE 9

Self-metathesis of 1-Dodecene

Figure 28:
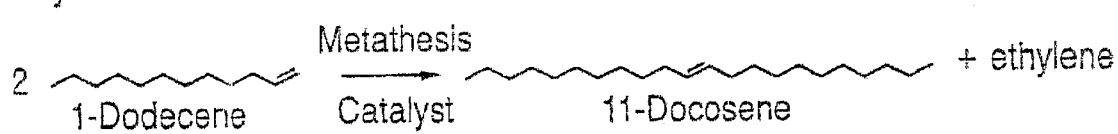
FIG. 28 shows a self-metathesis of 1-dodecene to produce 11-docosene.

With reference to FIG. 28, to a dry 50 mL round bottomed flask was added 61.0 g (360 mmol) 1-dodecene. The flask was purged with nitrogen for 20 minutes, followed by the addition of 0.25 g (0.30 mmol) Catalyst 823, and the mixture was stirred at 35° C. for 18 hours, under a 10 mmHg vacuum. The metathesis catalyst was removed by filtration through 100 g of silica gel, 170 to 400 mesh, to yield 50.2 g (324 mmol) of 11-docosene. This product was used without further purification.

Cross Metathesis of Meadowfoam Oil and 11-Docosene

Figure 29:
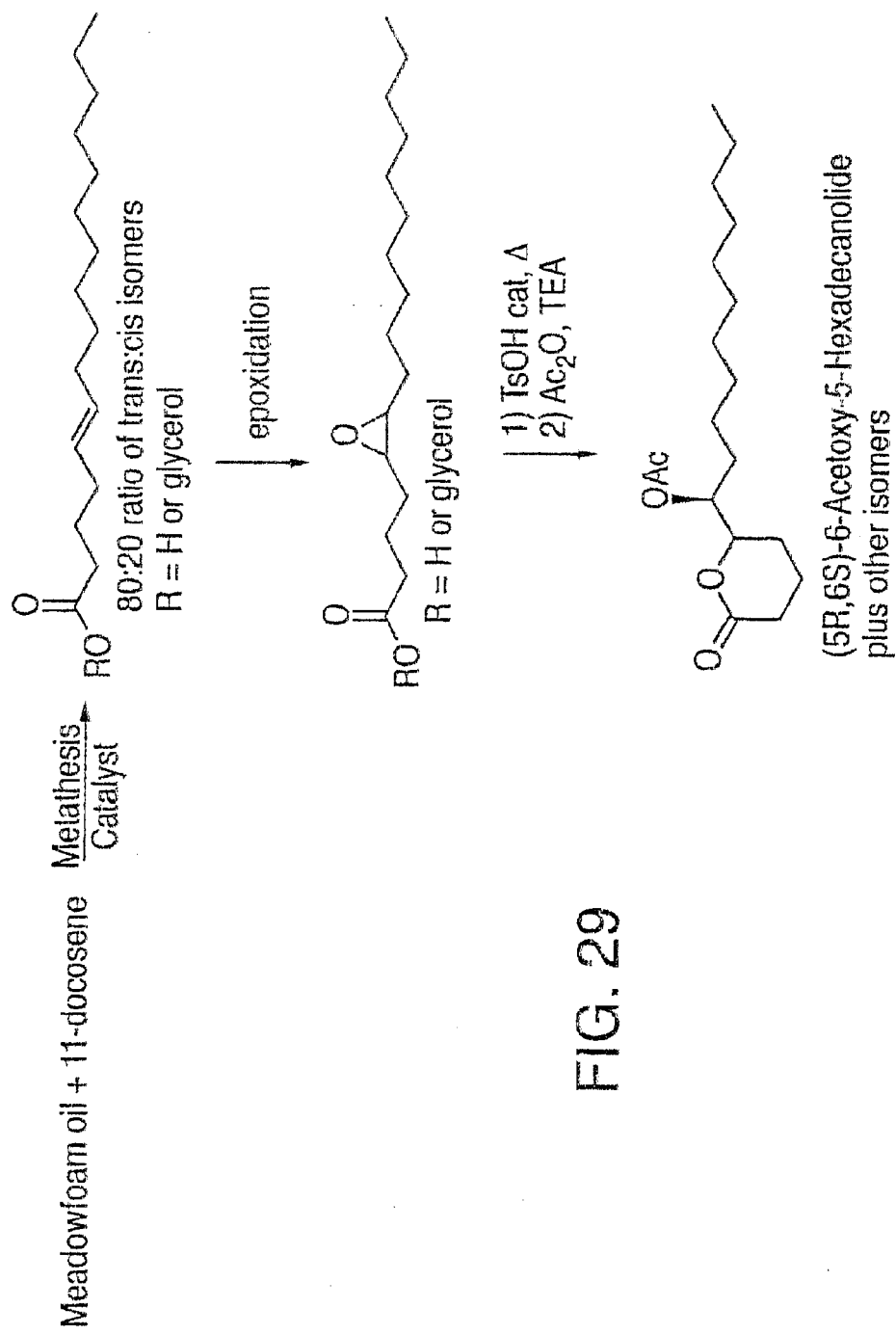
FIG. 29 shows a synthesis of mosquito oviposition pheromone involving the cross-metathesis of meadowfoam oil and 11-docosene.

With reference to FIG. 29, the synthesis of (5R,6S)-6-acetoxy-5-hexadecanolide and its stereoisomers was as described in Example 8 except 5.5 g (18 mmol) of 11-docosene was used in place of 1-dodecene.

EXAMPLE 10

Cross Metathesis of Methyl Hexenoate and 11-Docosene

Figure 30:
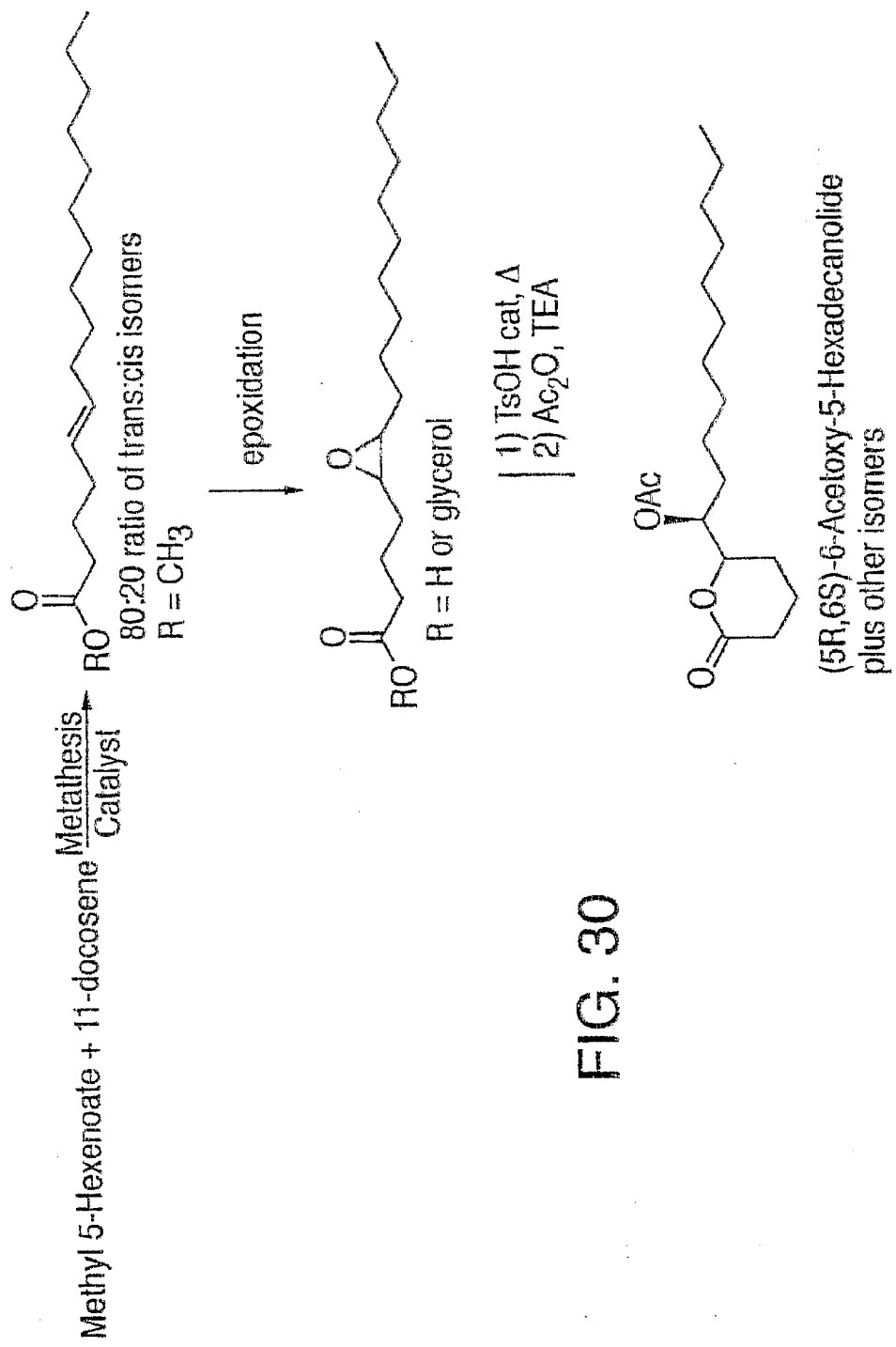
FIG. 30 shows a synthesis of mosquito oviposition pheromone involving the cross-metathesis of methyl 5-hexenoate and 11-docosene.

With reference to FIG. 30, the synthesis of (5R,6S)-6-acetoxy-5-hexadecanolide and its stereoisomers was as described in Example 8 except 1.15 g (9 mmol) of methyl hexenoate was used in place of meadowfoam oil and 5.5 g (18 mmol) of 11-docosene was used in place of 1-dodecene.

EXAMPLE 11

Cross Metathesis of Methyl Hexenoate and 1-Dodecene

Figure 31:
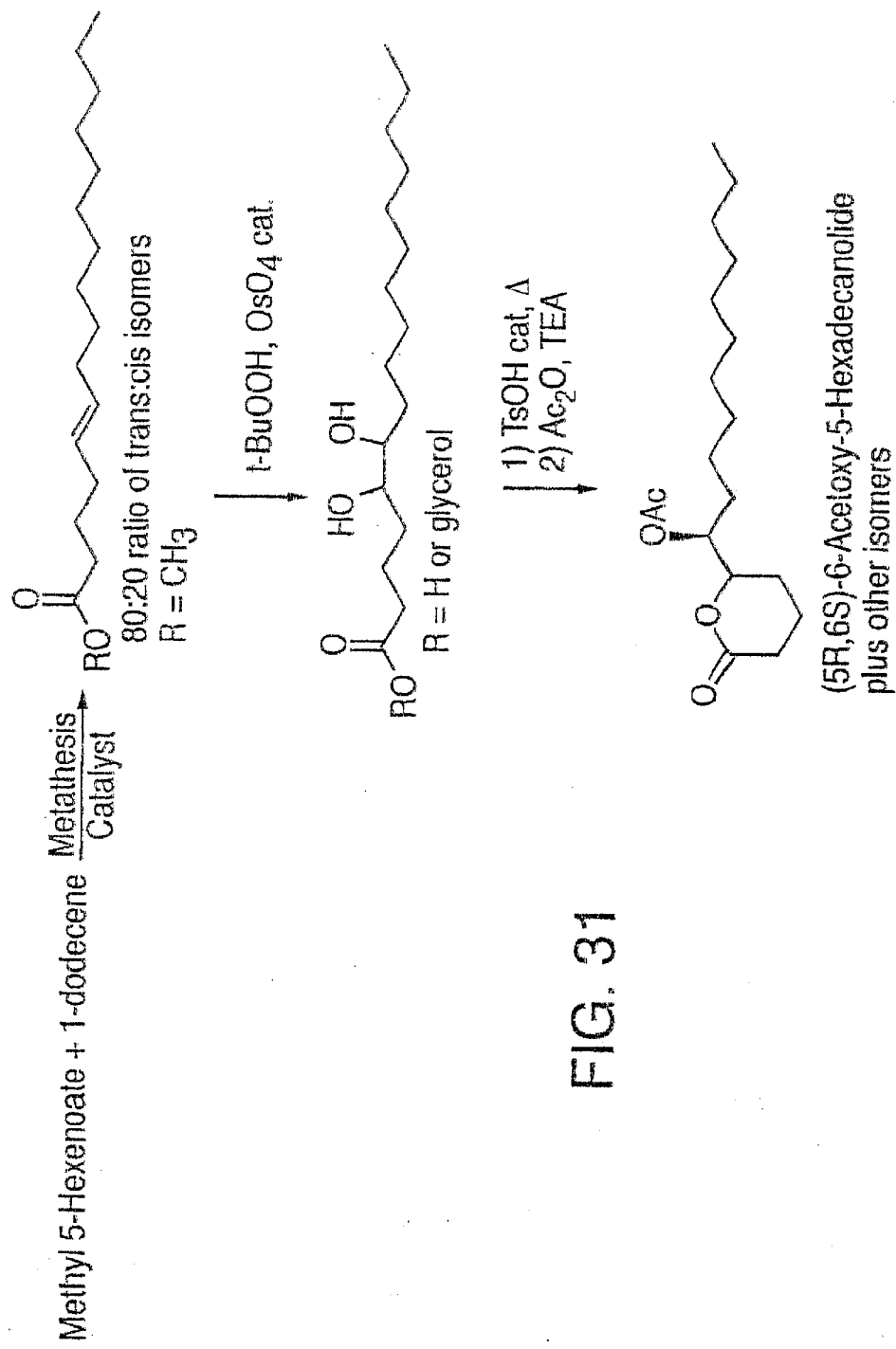
FIG. 31 shows a synthesis of mosquito oviposition pheromone involving the cross-metathesis of methyl 5-hexenoate and 1-dodecene.

With reference to FIG. 31, the synthesis of (5R,6S)-6-acetoxy-5-hexadecanolide and its stereoisomers was as described in Example 8 except 1.15 g (9 mmol) of methyl hexenoate was used in place of meadowfoam oil.

EXAMPLE 12

Cross Metathesis of Meadowfoam Oil and 1-Dodecene

Figure 32:
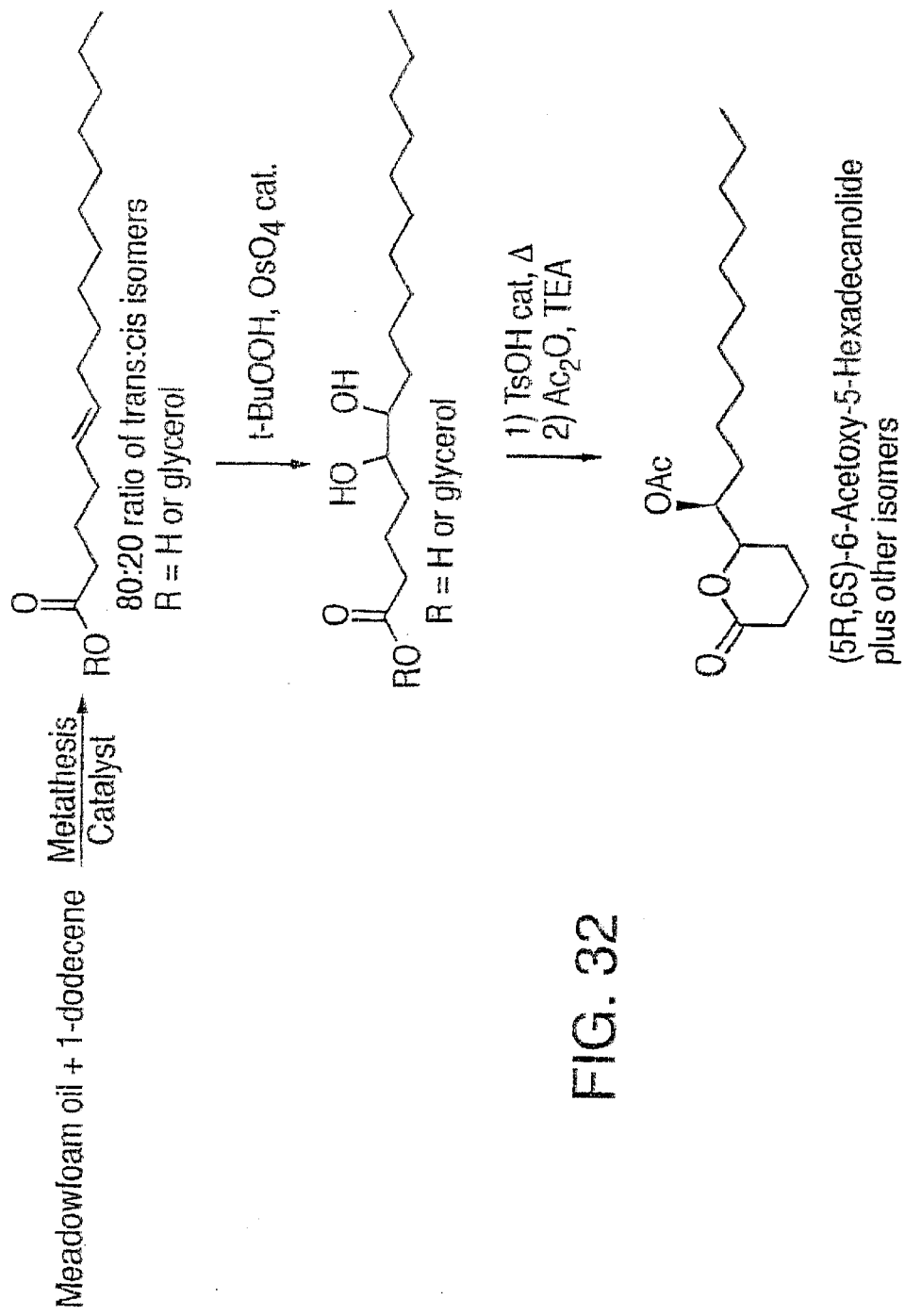
FIG. 32 shows an alternative synthesis of mosquito oviposition pheromone involving the cross-metathesis of meadowfoam oil and 1-dodecene.

With reference to FIG. 32, the synthesis of (5R,6S)-6-acetoxy-5-hexadecanolide and its stereoisomers was as described in Example 8 except the oxidation of the double bond to a diol was as described by Olagbemiro et al.

EXAMPLE 13

Cross Metathesis of Meadowfoam Oil and 11-Docosene

Figure 33:
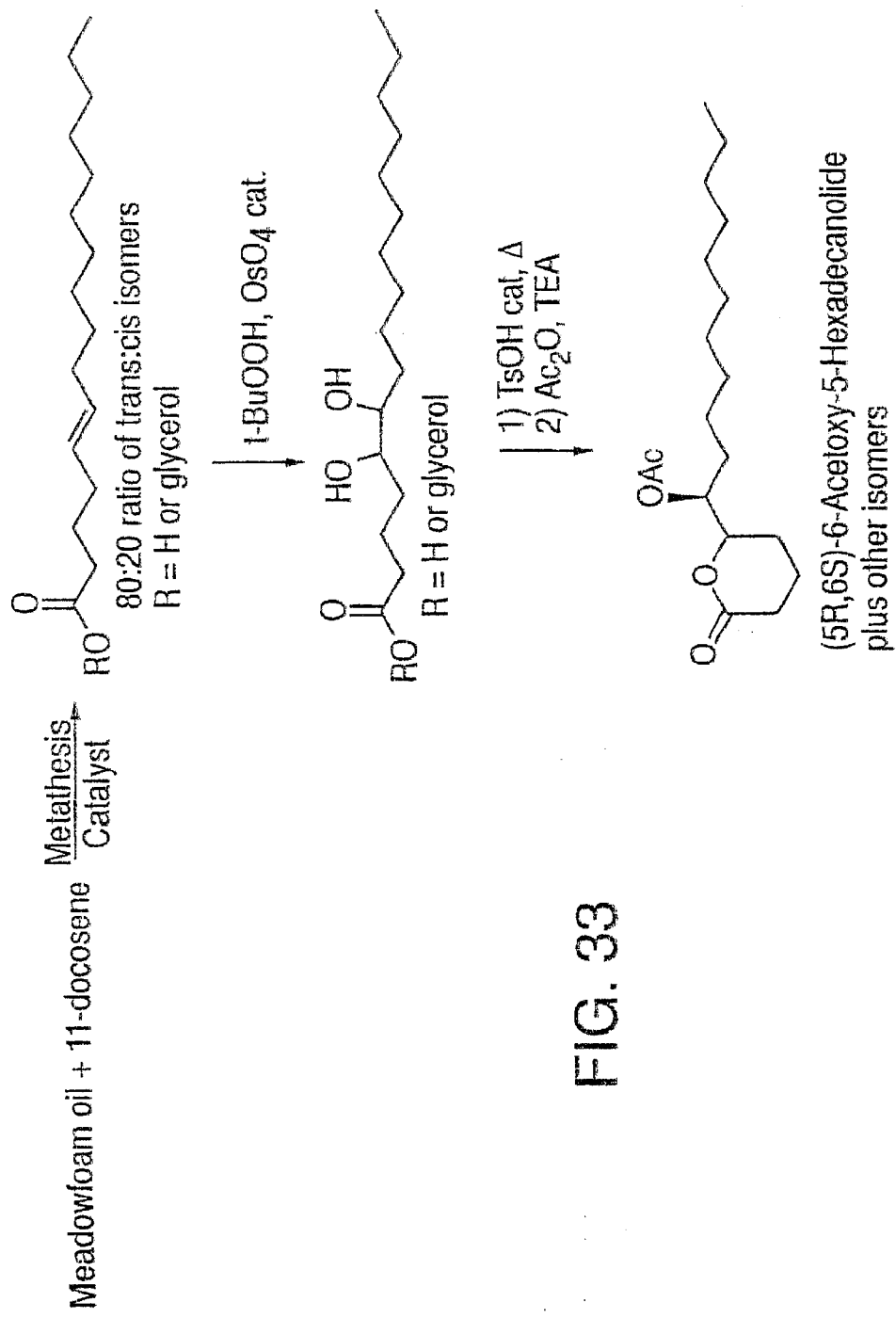
FIG. 33 shows an alternative synthesis of mosquito oviposition pheromone involving the cross-metathesis of meadowfoam oil and 11-docosene.

With reference to FIG. 33, the synthesis of (5R,6S)-6-acetoxy-5-hexadecanolide and its stereoisomers was as described in Example 8 except 5.5 g (18 mmol) of 11-docosene was used in place of 1-dodecene and the oxidation of the double bond to a diol was as described by Olagbemiro et al.

EXAMPLE 14

Cross Metathesis of Methyl Hexenoate and 11-Docosene

Figure 34:
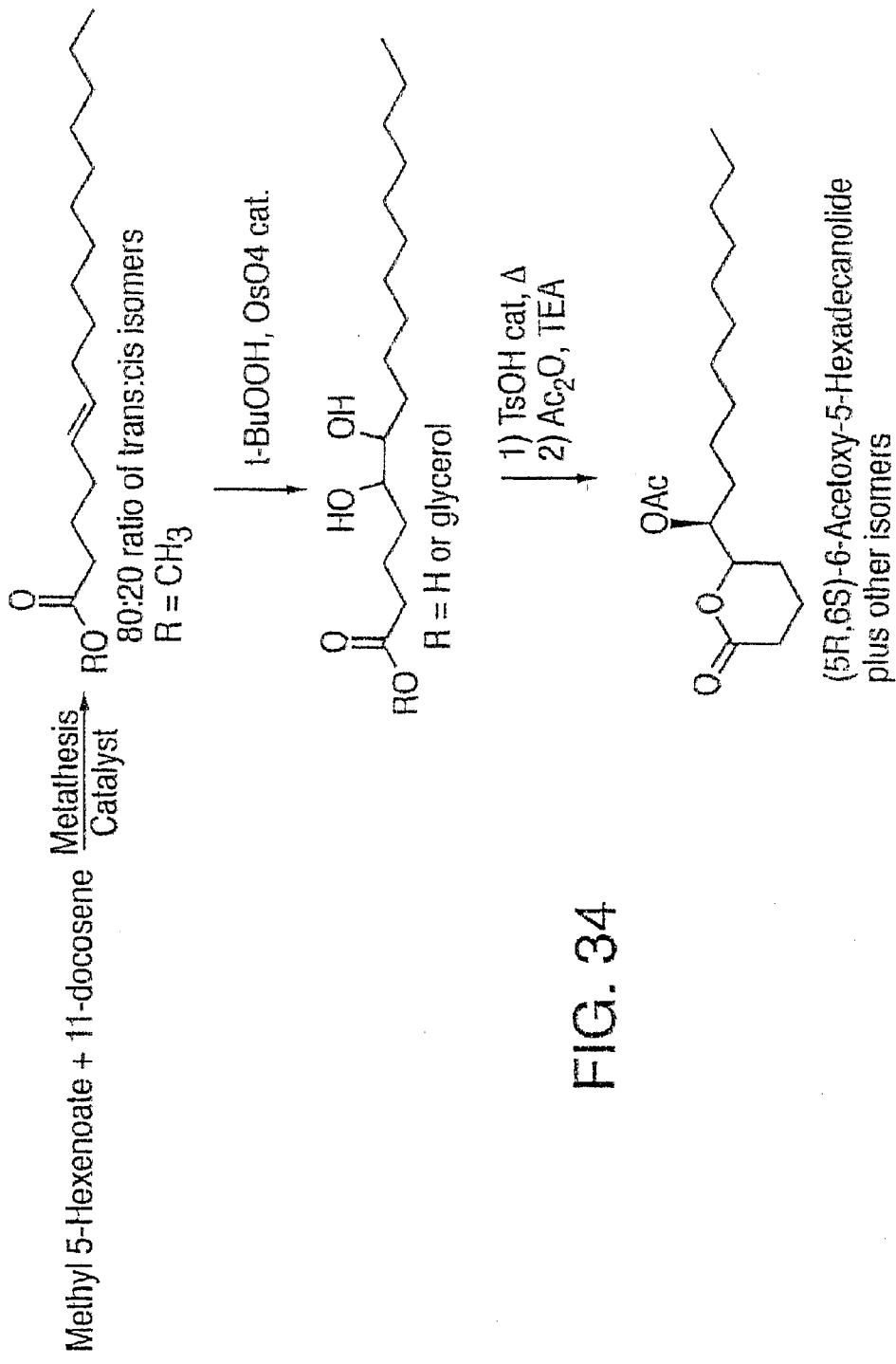
FIG. 34 shows an alternative synthesis of mosquito oviposition pheromone involving the cross-metathesis of methyl 5-hexenoate and 11-docosene.

With reference to FIG. 34, the synthesis of (5R,6S)-6-acetoxy-5-hexadecanolide and its stereoisomers was as described in Example 8 except 1.15 g (9 mmol) of methyl hexenoate was used in place of meadowfoam oil and 5.5 g (18 mmol) of 11-docosene was used in place of 1-dodecene and the oxidation of the double bond to a diol was as described by Olagbemiro et al.

EXAMPLE 15

Cross Metathesis of Methyl Hexenoate and 1-Dodecene

Figure 35:
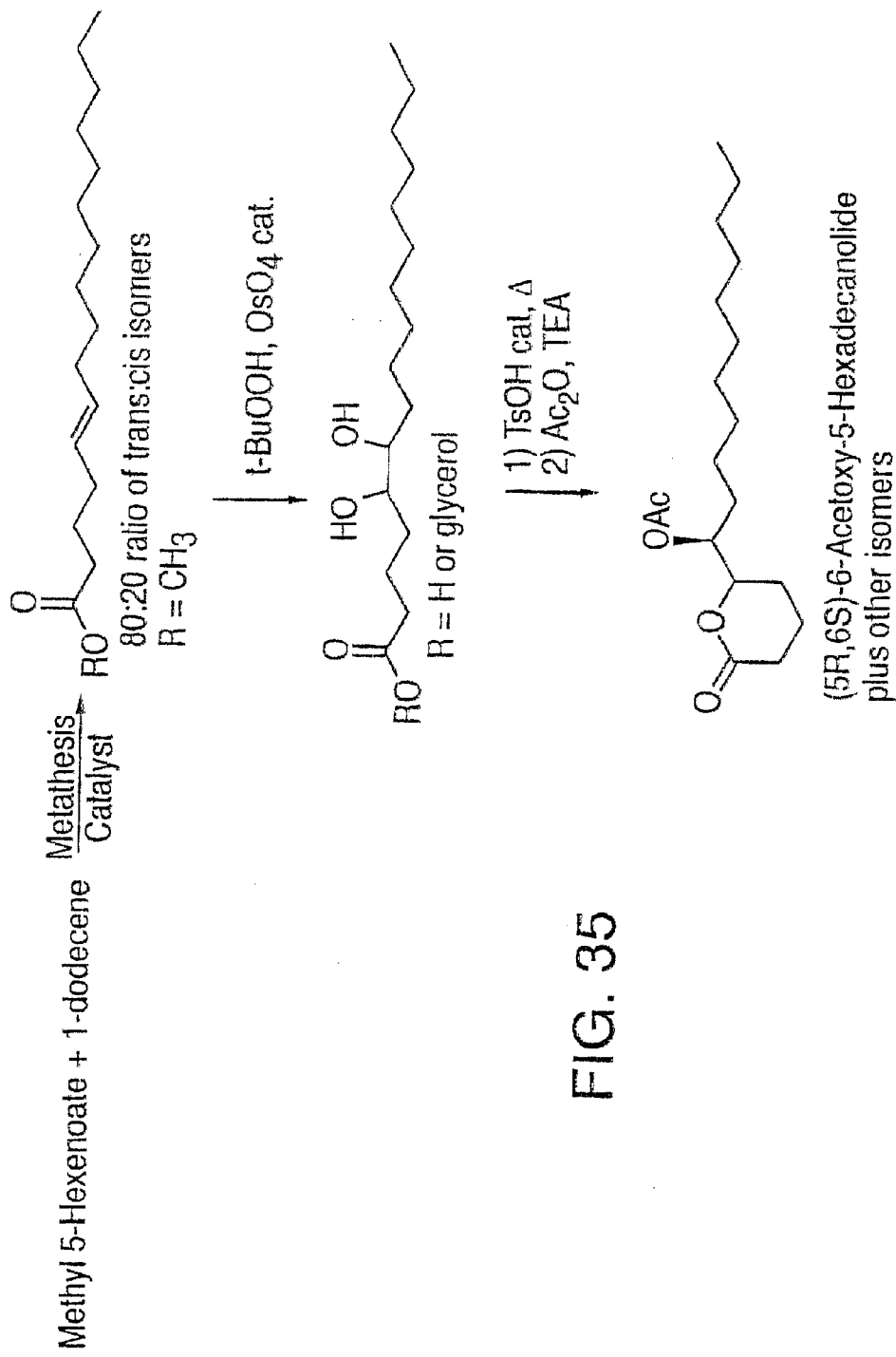
FIG. 35 shows an alternative synthesis of mosquito oviposition pheromone involving the cross-metathesis of methyl 5-hexenoate and 1-dodecene.

With reference to FIG. 35, the synthesis of (5R,6S)-6-acetoxy-5-hexadecanolide and its stereoisomers was as described in Example 8 except 1.15 g (9 mmol) of hexenyl acetate was used in place of meadowfoam oil. The oxidation of the 5-hexadecenyl acetate to 5-hexadecanoic acid was accomplished as described by Witzmann, et al. in "Di-Glyceraldehyde Ethyl Acetal" Organic Synthesis Collective Volume II, 1943 p 307 and the oxidation of the double bond to a diol was as described by Olagbemiro et al.

EXAMPLE 16

Cross Metathesis of Hexenyl Acetate and 1-Dodecene

Figure 36:
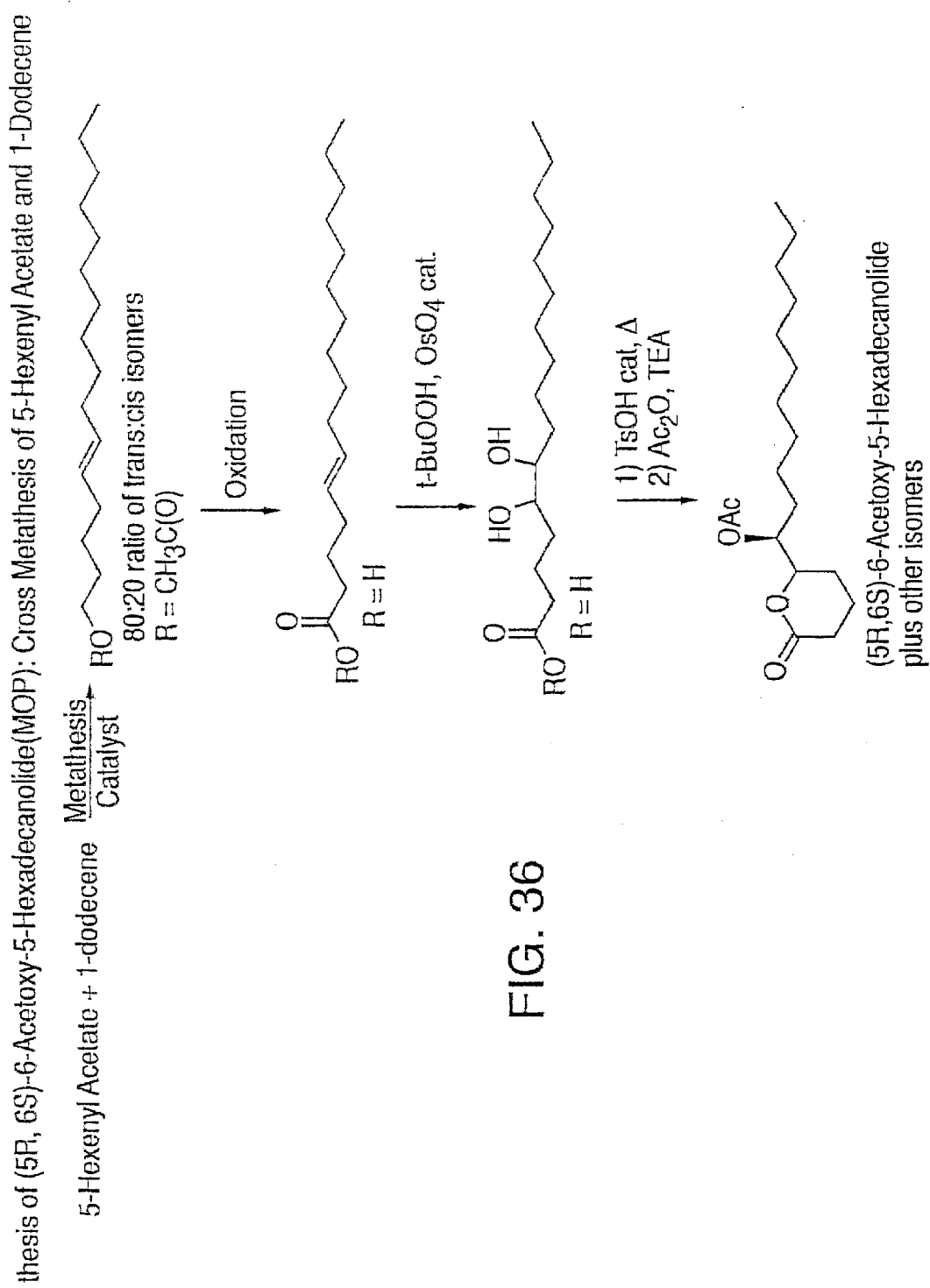
FIG. 36 shows a synthesis of mosquito oviposition pheromone involving the cross-metathesis of 5-hexenyl acetate and 1-dodecene.

With reference to FIG. 36, the synthesis of (5R,6S)-6-acetoxy-5-hexadecanolide and its stereoisomers was as described in Example 8 except 1.15 g (9 mmol) of hexenyl acetate was used in place of meadowfoam oil. The oxidation of the 5-hexadecenyl acetate to 5-hexadecenoic acid was accomplished as described by Witzmann et al. and the oxidation of the double bond to a diol was as described by Olagbemiro et al.

EXAMPLE 17

Cross Metathesis of Hexenyl Acetate and 11-Docosene

Figure 37:
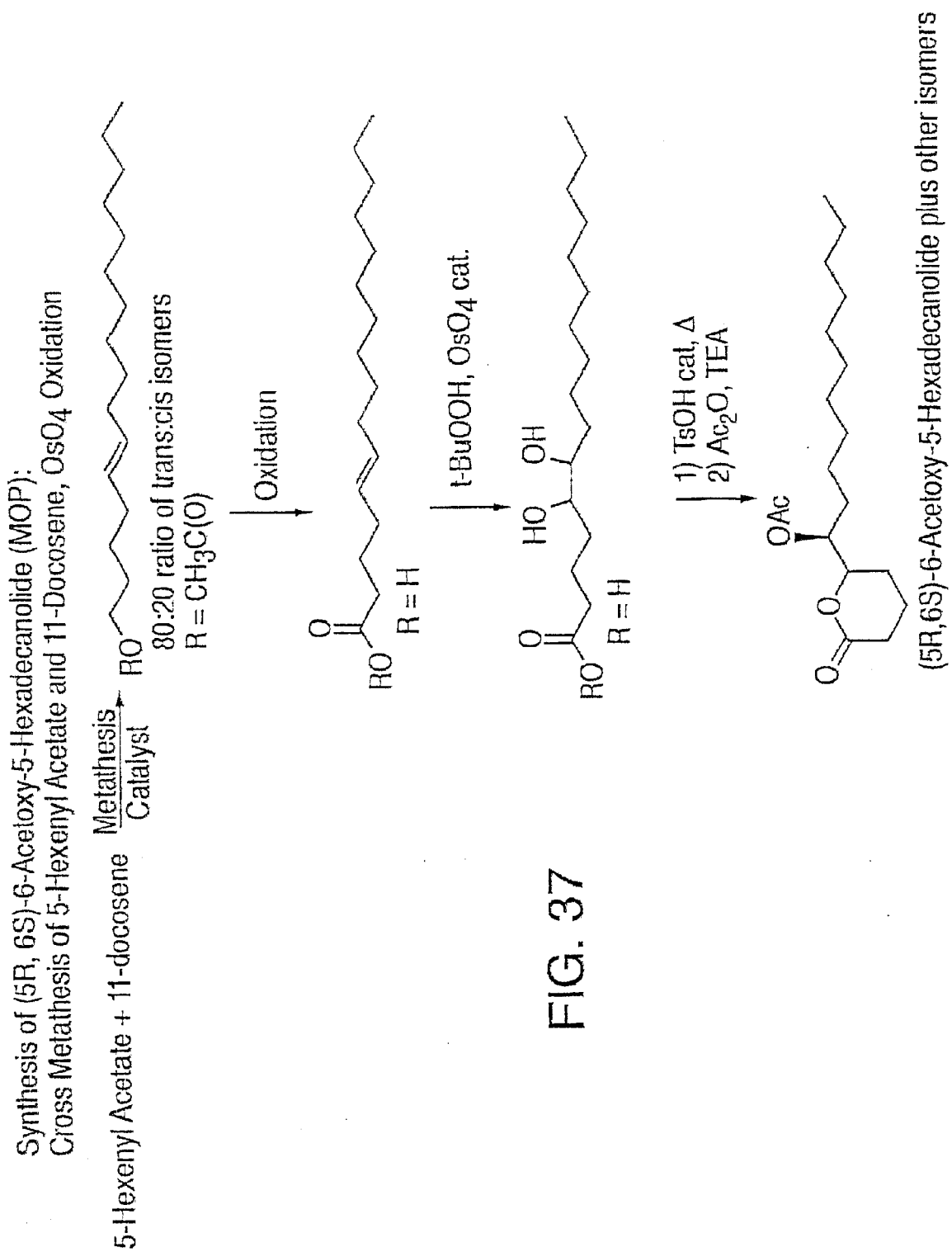
FIG. 37 shows a synthesis of mosquito oviposition pheromone involving the cross-metathesis of 5-hexenyl acetate and 11-docosene.

With reference to FIG. 37, the synthesis of (5R,6S)-6-acetoxy-5-hexadecanolide and its stereoisomers was as described in Example 8 except 1.15 g (9 mmol) of hexenyl acetate was used in place of meadowfoam oil. The oxidation of the 5-hexadecenyl acetate to 5-hexadecenoic acid was accomplished as described by Witzmann et al. and 5.5 g (18 mmol) of 11-docosene was used in place of 1-dodecene and the oxidation of the double bond to a diol was as described by Olagbemiro et al.

EXAMPLE 18

Cross Metathesis of Hexenal Diethyl Acetal and 11-Docosene

Figure 38:
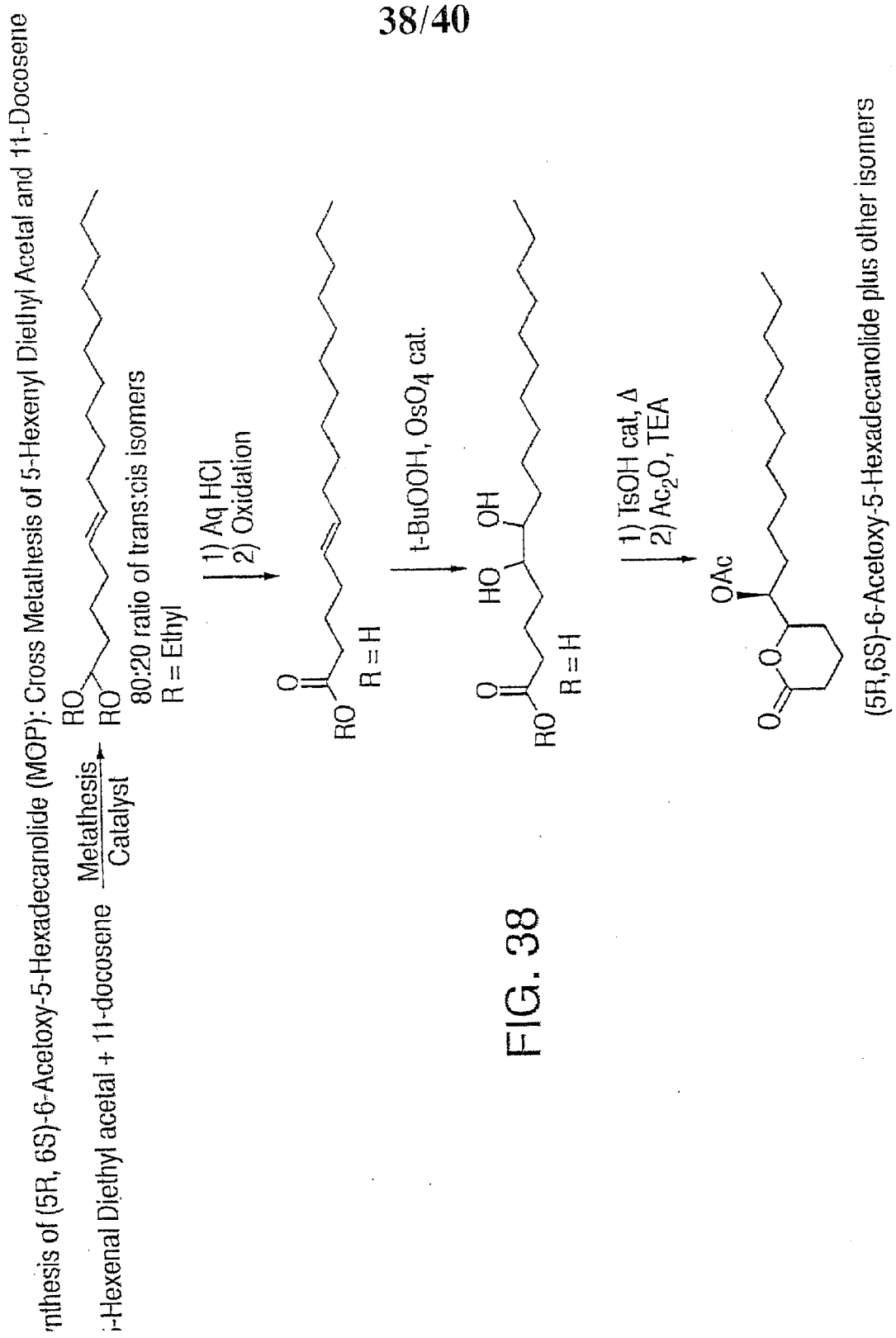
FIG. 38 shows a synthesis of mosquito oviposition pheromone involving the cross-metathesis of 5-hexenal diethyl acetal and 11-docosene.

With reference to FIG. 38, the synthesis of (5R,6S)-6-acetoxy-5-hexadecanolide and its stereoisomers was as described in Example 8 except 1.55 g (9 mmol) of 5-hexenal diethyl acetal was used in place of meadowfoam oil. The oxidation of the 5-hexadecenal diethyl acetal to 5-hexadecenoic acid was accomplished as described by Ruhoff, J. R. ("N-Heptanoic Acid" Organic Synthesis Collective Volume II, 1943 p 314) and 5.5 g (18 mmol) of 11-docosene was used in place of 1-dodecene and the oxidation of the double bond to a diol was as described by Olagbemiro et al.

EXAMPLE 19

Cross Metathesis of Hexenal Diethyl Acetal and 1-Dodecene

Figure 39:
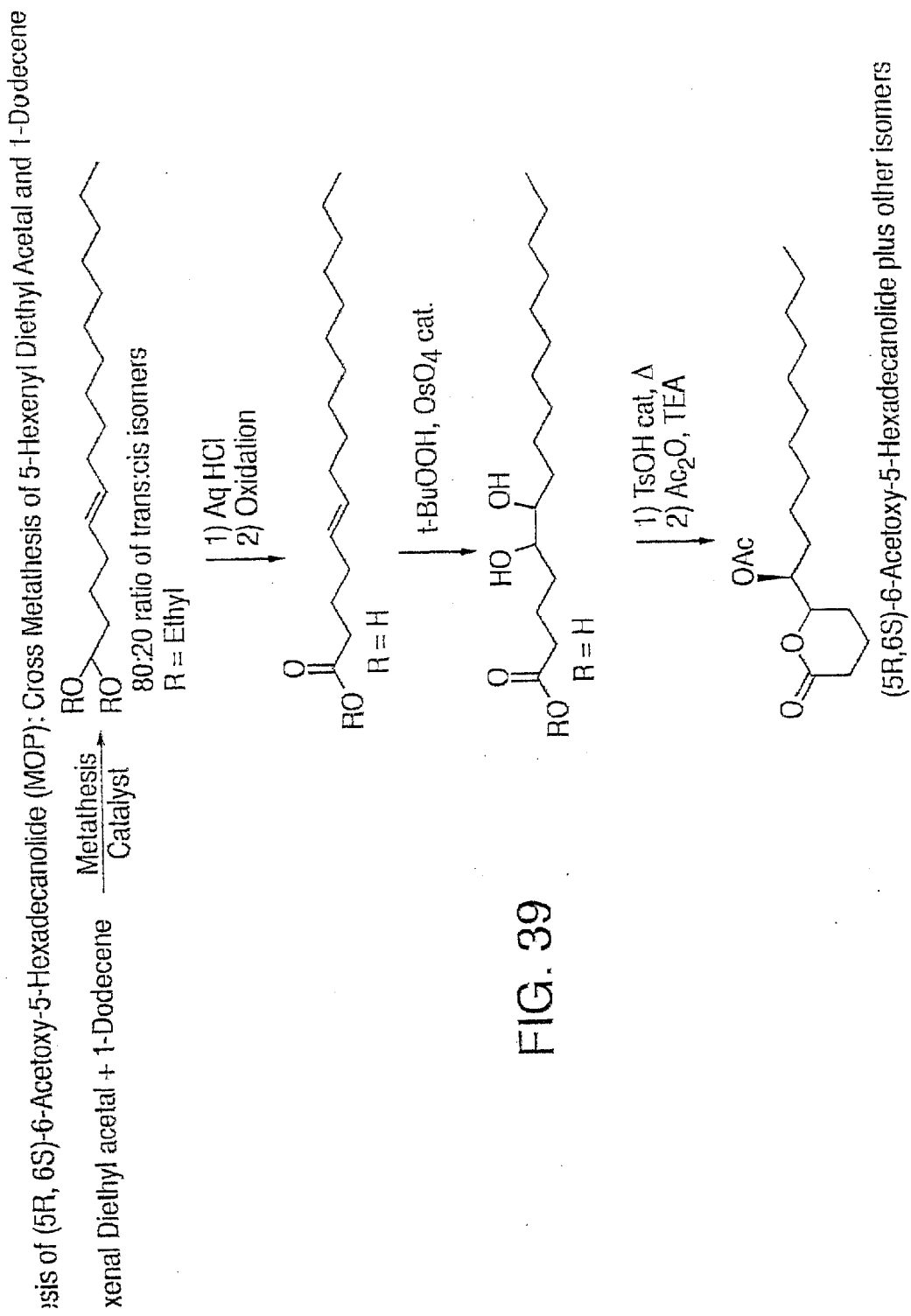
FIG. 39 shows a synthesis of mosquito oviposition pheromone involving the cross-metathesis of 5-hexenal diethyl acetal and 1-dodecene.

With reference to FIG. 39, the synthesis of (5R,6S)-6-acetoxy-5-hexadecanolide and its stereoisomers was as described in Example 8 except 1.55 g (9 mmol) of hexenal diethyl acetal was used in place of meadowfoam oil. The oxidation of the 5-hexadecenal diethyl acetal to 5-hexadecenoic acid was accomplished as described by Ruhoff and the oxidation of the double bond to a diol was as described by Olagbemiro et al.

Figure 40:
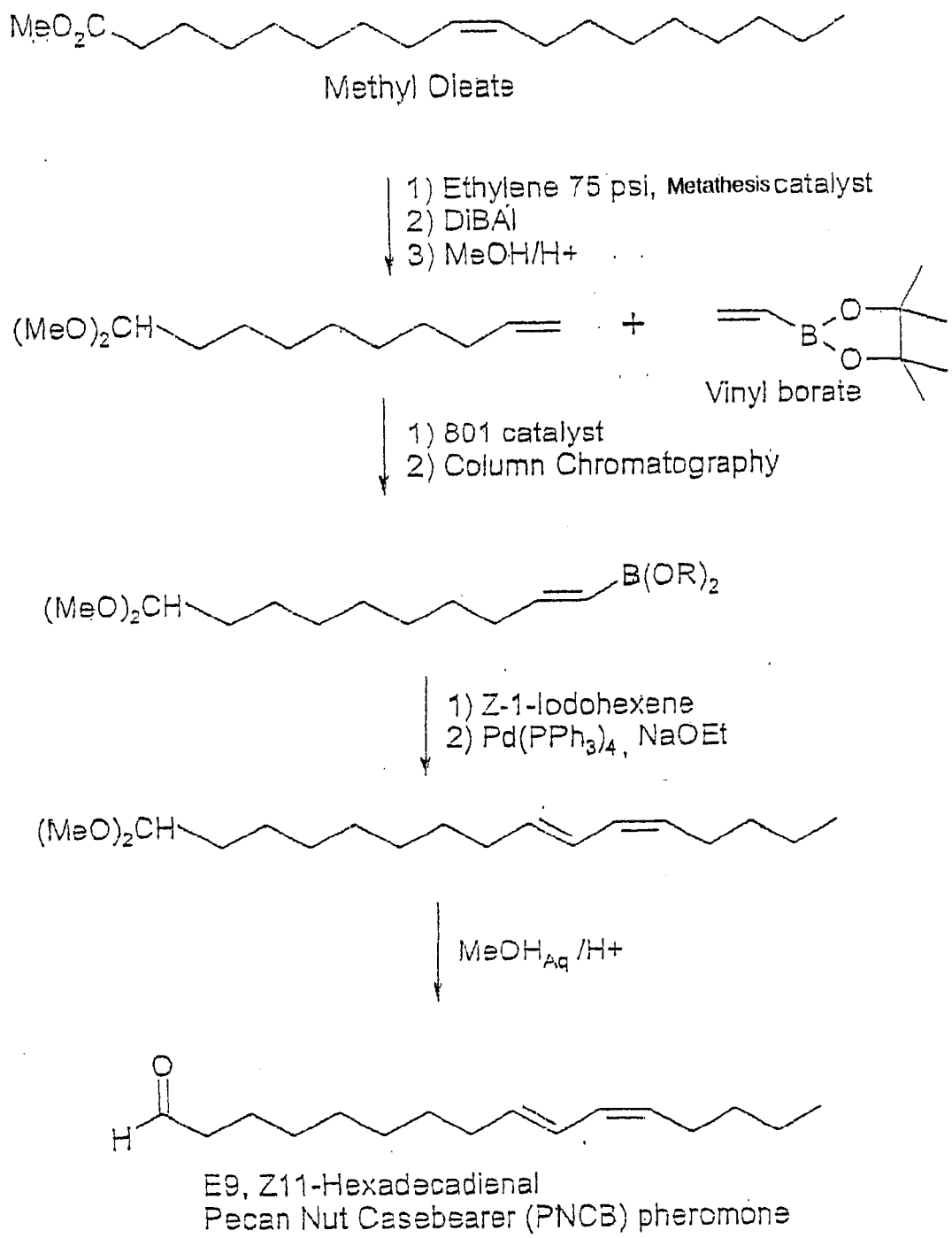
FIG. 40 shows a preferred synthesis of E-9,Z-11-hexadecadienal involving the cross-metathesis of vinyl borate pinacol ester with 9-decenal diethyl acetal.

Syntheses of the Pecan Nut Case Bearer pheromone (PNCB): E-9,Z-11-Hexadecadienal FIG. 40 shows a synthesis of PNCB which involves the cross-metathesis of vinyl borate pinacol ester (Matheson, D. S J Am Chem Soc (1960) 82, 4228–4233) with 9-decenal diethyl acetal (synthesized by the Swern oxidation of commercially available 9-decenol to yield 9-decenal, then protecting it as the acetal with ethanol and hydrochloric acid) with Catalyst 823 to yield the pinacol ester of 1-borodecenal diethyl acetal. This product was coupled with Z-1-iodohexene (Normant *Org Syn* VII, p 290–294) under Suzuki conditions as described by Miycuira Org Syn VIII p 532, to yield E-9,Z-11-hexadecadienal diethyl acetal. This material was purified by column chromatography, and the acetal was hydrolyzed in aqueous methanol and water with cat p-toluenesulfonic acid at 35° C. for 24 hours. E-9,Z-11-hexadecadienal was isolated by concentrating the reaction mixture and purified by column chromatography.

Although the descriptions of the synthetic schemes shown in FIGS. 9, 11–25, and 27–40 may include specific catalysts and starting materials, skilled persons will appreciate that the figures and descriptions are exemplary only and can be modified by the use of other metathesis catalysts, such as the Class I–IV metathesis catalysts shown in FIGS. 2–5. Specifically with respect to the synthetic schemes of FIGS. 9, 11–25, and 27–40, the Class IV metathesis catalysts are preferred, particularly Catalysts 848, 826, 807, and 785, because theses catalysts can be employed in much smaller quantities than catalysts of the other three classes. Catalysts 848 and 826 are currently most preferred be they are currently more readily synthesized even though Catalysts 807 and 785 can be used in smaller quantities and produce higher yields. Catalysts 823, 801, and 716 are also preferred, but generally produce smaller yields than the Class IV catalysts. Catalysts 791 and 707 are currently not preferred.

Skilled persons will also appreciate that the synthetic schemes shown in FIGS. 9, 11–25, and 27–40 can be modified by the use of other starting materials, such as other alcohol-protected derivatives of the starting materials as described above, and can for example be employed to provide alternative syntheses of the cross-metathesis products presented herein or to synthesize E-9,Z-11-hexadecadienal, E-3,Z-5-dodecadienyl acetate, E-8,Z-10-pentadecadienyl acetate, E-7,Z-9-dodecadienyl acetate, Z-5, E-7-dodecadienol, E-5,Z-7-dodecadienol, Z-9,E-11-tetradecadienyl acetate and Z-11,E-13-hexadecadienyl acetate, or other similar products.

It will be obvious to those having skill in the art that many changes may be made to the details of the above-described embodiment of this invention without departing from the underlying principles thereof. The scope of the present invention should, therefore, be determined only by the following claims.

What is claimed is:

1. A method for synthesizing a metathesis product, comprising:

cross-metathesizing a terminal olefin and an internal olefin in the presence of a metathesis catalyst, selected from Class I–IV metathesis catalysts, to form the metathesis product and a side product;

applying conditions of sufficiently high temperature and/or sufficiently low pressure such that the side product evaporates out of the reaction chamber.

2. The method of claim 1 in which the metathesis starting olefins comprise the form R—$(CH=CH)_k(CH_2)_n(CHX)_g(CH_2)_m$—H, where X is selected from a hydrogen, an alcohol, an acetate, a carboxylate ester, a carboxylic acid, an aldehyde, a halide, or a tosylate, mesylate, or derivatives thereof, and n and m are each selected from zero and an integer less than or equal to 20, R is selected from H, $CH_2$ or $(CH_2)_n(CHX)_g(CH_2)_m$—H; and cross-metathesizing the first product with a second alpha olefin of form $QCH(CH_2)_r$W, where Q is selected from $CH_2$ or $CH(CH_2)_r$W, r is selected from zero and an integer less than or equal to 20, and W is selected from an alcohol, acetate, carboxylate ester, carboxylic acid, an aldehyde, a halide, hydrogen, or derivatives thereof in the presence of a second metathesis catalyst to form a second product of form $H(CH_2)_m(CHX)_g(CH_2)_n(CH=CH)_p(CH_2)_r$W or derivatives thereof, where p is less than or equal to the sum of m and n, and a second side product in the form of $CH_2Z$, where Z is selected from $CH_2$ or $CH(CH_2)_n(CHX)_g(CH_2)_mCH_3$ under conditions of sufficiently high temperature and/or sufficiently low pressure such that the second side product evaporates out of the reaction chamber.

3. The method of claim 1 in which the metathesis starting olefins comprise alkenyl esters and derivatives thereof of which contains 2 to 22 carbons, alkenyl halides and derivatives thereof of which contains 2 to 22 carbons, alpha, omega-alkenyl diester and derivatives thereof of which contains 4 to 40 carbons, alpha, omega-alkenyl dihalides and derivatives thereof of which contains 4 to 40 carbons, alkenes of which contains 2 to 44 carbons, alkenols of which contains 2 to 22 carbons, or alkene diols of which contains 4 to 40 carbons.

4. The method of claim 1 in which the metathesis starting olefins comprise alkenyl esters and derivatives thereof of which contains 2 to 10 carbons, alkenyl halides and derivatives thereof of which contains 2 to 10 carbons, alpha, omega-alkenyl diester and derivatives thereof of which contains 4 to 20 carbons, alpha, omega-alkenyl dihalides and derivatives thereof of which contains 4 to 20 carbons, alkenes of which contains 2 to 20 carbons, alkenols of which contains 2 to 10 carbons, alkene diols of which contains 4 to 20 carbons.

5. The method of claim 1 in which the metathesis starting olefins comprise at least one of: 1-hexene, 5-decene, 1-butene, 3-hexene, 5-hexenyl acetate, 5-hexenyl chloride, 1,10-diacetoxy-5-decene, 1,10-dichloro-5-decene, 3-hexenyl acetate, 3-hexenol, 1-bromo-3-hexene, 1-chloro-3-hexene, 1-dodecene, 4-pentenyl chloride, 1,8-dichloro-4-octene, 4-pentenyl acetate, 1,8-diacetoxy-4-octene, 1,4-diacetoxy-2-butene, 1,4-dichloro-2-butene, 11-docosene, methyl 5-eicosenoate, 5-eicosneyl acetate, methyl 11-eicosenoate, or 11-eicosenyl acetate.

6. The method of claim 1 in which the metathesis product comprises a second product of form $H(CH_2)_m(CHX)_g(CH_2)_n(CH=CH)_p(CH_2)_rW$ or derivatives thereof.

7. The method of claim 1 in which the metathesis product comprises: 5-decenyl acetate, methyl 5-decenoate, 9-tetradecenyl formate, 9-tetradecenyl chloride, 9-tetradecenyl acetate, 11-tetradecenyl acetate, methyl 11-tetradecenoate, 11-tetradecenyl chloride, methyl 5-hexadecenoate, or 8,10-dodecadienol, or acids, salts, or esters thereof.

8. The method of claim 2, wherein metathesis catalyst comprises one of: catalyst 823, 801, 876, 848, 826, 785, 816, 794, 846, 824, or 794.

9. A method for synthesizing a metathesis product, comprising:
   selecting a first internal olefin;
   selecting a second internal olefin;
   cross-metathesizing the first internal olefin and the second internal olefin in the presence of a metathesis catalyst selected from Class I–IV metathesis catalysts to form the metathesis product.

10. The method of claim 9 in which the metathesis starting olefins comprise the form $R—(CH=CH)_k(CH_2)_n(CHX)_g(CH_2)_m—H$, where X is selected from a hydrogen, an alcohol, an acetate, a carboxylate ester, a carboxylic acid, an aldehyde, a halide, or a tosylate, mesylate, or derivatives thereof, and n and m are each selected from zero and an integer less than or equal to 20, R is selected from H, $CH_2$ or $(CH_2)_n(CHX)_g(CH_2)_m—H$; and cross-metathesizing the first product with a second alpha olefin of form $QCH(CH_2)_rW$, where Q is selected from $CH_2$ or $CH(CH_2)_rW$, r is selected from zero and an integer less than or equal to 20, and W is selected from an alcohol, acetate, carboxylate ester, carboxylic acid, an aldehyde, a halide, hydrogen, or derivatives thereof in the presence of a second metathesis catalyst to form a second product of form $H(CH_2)_m(CHX)_g(CH_2)_n(CH=CH)_p(CH_2)_rW$ or derivatives thereof, where p is less than or equal to the sum of m and n, and a second side product in the form of $CH_2Z$, where Z is selected from $CH_2$ or $CH(CH_2)_n(CHX)_g(CH_2)_mCH_3$ under conditions of sufficiently high temperature and/or sufficiently low pressure such that the second side product evaporates out of the reaction chamber.

11. The method of claim 9 in which the metathesis starting olefins comprise alkenyl esters and derivatives thereof of which contains 2 to 22 carbons, alkenyl halides and derivatives thereof of which contains 2 to 22 carbons, alpha, omega-alkenyl diester and derivatives thereof of which contains 4 to 40 carbons, alpha, omega-alkenyl dihalides and derivatives thereof of which contains 4 to 40 carbons, alkenes of which contains 2 to 44 carbons, alkenols of which contains 2 to 22 carbons, or alkene diols of which contains 4 to 40 carbons.

12. The method of claim 9 in which the metathesis starting olefins comprise alkenyl esters and derivatives thereof of which contains 2 to 10 carbons, alkenyl halides and derivatives thereof of which contains 2 to 10 carbons, alpha, omega-alkenyl diester and derivatives thereof of which contains 4 to 20 carbons, alpha, omega-alkenyl dihalides and derivatives thereof of which contains 4 to 20 carbons, alkenes of which contains 2 to 20 carbons, alkenols of which contains 2 to 10 carbons, alkene diols of which contains 4 to 20 carbons.

13. The method of claim 9 in which the metathesis starting olefins comprise at least one of: 1-hexene, 5-decene, 1-butene, 3-hexene, 5-hexenyl acetate, 5-hexenyl chloride, 1,10-diacetoxy-5-decene, 1,10-dichloro-5-decene, 3-hexenyl acetate, 3-hexenol, 1-bromo-3-hexene, 1-chloro-3-hexene, 1-dodecene, 4-pentenyl chloride, 1,8-dichloro-4-octene, 4-pentenyl acetate, 1,8-diacetoxy-4-octene, 1,4-diacetoxy-2-butene, 1,4-dichloro-2-butene, 11-docosene, methyl 5-eicosenoate, 5-eicosneyl acetate, methyl 11-eicosenoate, or 11-eicosenyl acetate.

14. The method of claim 9 in which the metathesis product comprises a second product of form $H(CH_2)_m(CHX)_g(CH_2)_n(CH=CH)_p(CH_2)_rW$ or derivatives thereof.

15. The method of claim 9 in which the metathesis product comprises: 5-decenyl acetate, methyl 5-decenoate, 9-tetradecenyl formate, 9-tetradecenyl chloride, 9-tetradecenyl acetate, 11-tetradecenyl acetate, methyl 11-tetradecenoate, 11-tetradecenyl chloride, methyl 5-hexadecenoate, 8,10-dodecadienol, 4-tridecenyl acetate, 8-chlorooctanyl acetate, 8-bromooctanol, or acids, salts, or esters thereof.

16. The method of claim 9, wherein metathesis catalyst comprises one of: catalyst 823, 801, 876, 848, 826, 785, 816, 794, 846, 824, or 794.

17. A method for synthesizing a metathesis product, comprising:
   selecting a first terminal olefin;
   selecting a second terminal olefin;
   cross-metathesizing the first terminal olefin and the second terminal olefin in the presence of a metathesis catalyst selected from Class I–IV metathesis catalysts to form the metathesis product and a side product; and
   applying conditions of sufficiently high temperature and/or sufficiently low pressure such that the side product evaporates out of the reaction chamber.

18. The method of claim 17 in which the metathesis starting olefins comprise the form $R—(CH=CH)_k(CH_2)_n(CHX)_g(CH_2)_n—H$, where X is selected from a hydrogen, an alcohol, an acetate, a carboxylate ester, a carboxylic acid, an aldehyde, a halide, or a tosylate, mesylate, or derivatives thereof, and n and m are each selected from zero and an integer less than or equal to 20, R is selected from H, $CH_2$ or $(CH_2)_n(CHX)_g(CH_2)_m—H$; and cross-metathesizing the first product with a second alpha olefin of form $QCH(CH_2)_rW$, where Q is selected from $CH_2$ or $CH(CH_2)_rW$, r is selected from zero and an integer less than or equal to 20, and W is selected from an alcohol, acetate, carboxylate ester, carboxylic acid, an aldehyde, a halide, hydrogen, or derivatives thereof in the presence of a second metathesis catalyst to form a second product of form $H(CH_2)_m(CHX)_g(CH_2)_n(CH=CH)_p(CH_2)_rW$ or derivatives thereof, where p is less than or equal to the sum of m and n, and a second side product in the form of $CH_2Z$, where Z is selected from $CH_2$ or $CH(CH_2)_n(CHX)_g(CH_2)_mCH_3$ under conditions of sufficiently high temperature and/or sufficiently low pressure such that the second side product evaporates out of the reaction chamber.

19. The method of claim 17 in which the metathesis starting olefins comprise alkenyl esters and derivatives thereof of which contains 2 to 22 carbons, alkenyl halides and derivatives thereof of which contains 2 to 22 carbons, alpha, omega-alkenyl diester and derivatives thereof of which contains 4 to 40 carbons, alpha, omega-alkenyl dihalides and derivatives thereof of which contains 4 to 40 carbons, alkenes of which contains 2 to 44 carbons, alkenols of which contains 2 to 22 carbons, or alkene diols of which contains 4 to 40 carbons.

20. The method of claim 17 in which the metathesis starting olefins comprise alkenyl esters and derivatives thereof of which contains 2 to 10 carbons, alkenyl halides and derivatives thereof of which contains 2 to 10 carbons, alpha, omega-alkenyl diester and derivatives thereof of which contains 4 to 20 carbons, alpha, omega-alkenyl dihalides and derivatives thereof of which contains 4 to 20 carbons, alkenes of which contains 2 to 20 carbons, alkenols of which contains 2 to 10 carbons, alkene diols of which contains 4 to 20 carbons.

21. The method of claim 17 in which the metathesis starting olefins comprise at least one of: 1-hexene, 5-decene, 1-butene, 3-hexene, 5-hexenyl acetate, 5-hexenyl chloride, 1,10-diacetoxy-5-decene, 1,10-dichloro-5-decene, 3-hexenyl acetate, 3-hexenol, 1-bromo-3-hexene, 1-chloro-3-hexene, 1-dodecene, 4-pentenyl chloride, 1,8-dichloro-4-octene, 4-pentenyl acetate, 1,8-diacetoxy-4-octene, 1,4-diacetoxy-2-butene, 1,4-dichloro-2-butene, 11-docosene, methyl 5-eicosenoate, 5-eicosneyl acetate, methyl 11-eicosenoate, or 11-eicosenyl acetate.

22. The method of claim 17 in which the metathesis product comprises a second product of form $H(CH_2)_m(CHX)_g(CH_2)_n(CH=CH)_p(CH_2)_rW$ or derivatives thereof.

23. The method of claim 17 in which the metathesis product comprises: 5-decenyl acetate, methyl 5-decenoate, 9-tetradecenyl formate, 9-tetradecenyl chloride, 9-tetradecenyl acetate, 11-tetradecenyl acetate, methyl 11-tetradecenoate, 11-tetradecenyl chloride, methyl 5-hexadecenoate, or 8,10-dodecadienol, or acids, salts, or esters thereof.

24. The method of claim 17 in which the yield of the metathesis product is greater than 15%.

25. The method of claim 17 in which the yield of the metathesis product is greater than 50%.

26. The method of claim 17 in which the yield of the metathesis product is greater than 75%.

27. The method of claim 17 in which the yield of the metathesis product is greater than 90%.

28. The method of claim 17, wherein metathesis catalyst comprises one of: catalyst 823, 801, 876, 848, 826, 785, 816, 794, 846, 824, or 794.

29. A method for synthesizing a metathesis product, comprising:

selecting a first terminal olefin;

selecting a second terminal olefin;

cross-metathesizing the first terminal olefin and the second terminal olefin in the presence of a metathesis catalyst selected from Class III or Class IV metathesis catalysts to form the metathesis product.

30. The method of claim 29 in which the metathesis starting olefins comprise the form $R-(CH=CH)_k(CH_2)_n(CHX)_g(CH_2)_m-H$, where X is selected from a hydrogen, an alcohol, an acetate, a carboxylate ester, a carboxylic acid, an aldehyde, a halide, or a tosylate, mesylate, or derivatives thereof, and n and m are each selected from zero and an integer less than or equal to 20, R is selected from H, $CH_2$ or $(CH_2)_n(CHX)_g(CH_2)_m-H$; and cross-metathesizing the first product with a second alpha olefin of form $QCH(CH_2)_rW$, where Q is selected from $CH_2$ or $CH(CH_2)_rW$, r is selected from zero and an integer less than or equal to 20, and W is selected from an alcohol, acetate, carboxylate ester, carboxylic acid, an aldehyde, a halide, hydrogen, or derivatives thereof in the presence of a second metathesis catalyst to form a second product of form $H(CH_2)_m(CHX)_g(CH_2)_n(CH=CH)_p(CH_2)_rW$ or derivatives thereof, where p is less than or equal to the sum of m and n, and a second side product in the form of $CH_2Z$, where Z is selected from $CH_2$ or $CH(CH_2)_n(CHX)_g(CH_2)_mCH_3$ under conditions of sufficiently high temperature and/or sufficiently low pressure such that the second side product evaporates out of the reaction chamber.

31. The method of claim 29 in which the metathesis starting olefins comprise alkenyl esters and derivatives thereof of which contains 2 to 22 carbons, alkenyl halides and derivatives thereof of which contains 2 to 22 carbons, alpha, omega-alkenyl diester and derivatives thereof of which contains 4 to 40 carbons, alpha, omega-alkenyl dihalides and derivatives thereof of which contains 4 to 40 carbons, alkenes of which contains 2 to 44 carbons, alkenols of which contains 2 to 22 carbons, or alkene diols of which contains 4 to 40 carbons.

32. The method of claim 29 in which the metathesis starting olefins comprise alkenyl esters and derivatives thereof of which contains 2 to 10 carbons, alkenyl halides and derivatives thereof of which contains 2 to 10 carbons, alpha, omega-alkenyl diester and derivatives thereof of which contains 4 to 20 carbons, alpha, omega-alkenyl dihalides and derivatives thereof of which contains 4 to 20 carbons, alkenes of which contains 2 to 20 carbons, alkenols of which contains 2 to 10 carbons, alkene diols of which contains 4 to 20 carbons.

33. The method of claim 29 in which the metathesis starting olefins comprise at least one of: 1-hexene, 5-decene, 1-butene, 3-hexene, 5-hexenyl acetate, 5-hexenyl chloride, 1,10-diacetoxy-5-decene, 1,10-dichloro-5-decene, 3-hexenyl acetate, 3-hexenol, 1-bromo-3-hexene, 1-chloro-3-hexene, 1-dodecene, 4-pentenyl chloride, 1,8-dichloro-4-octene, 4-pentenyl acetate, 1,8-diacetoxy-4-octene, 1,4-diacetoxy-2-butene, 1,4-dichloro-2-butene, 11-docosene, methyl 5-eicosenoate, 5-eicosneyl acetate, methyl 11-eicosenoate, or 11-eicosenyl acetate.

34. The method of claim 29 in which the metathesis product comprises a second product of form $H(CH_2)_m(CHX)_g(CH_2)_n(CH=CH)_p(CH_2)_rW$ or derivatives thereof.

35. The method of claim 29 in which the metathesis product comprises: 5-decenyl acetate, methyl 5-decenoate, 9-tetradecenyl formate, 9-tetradecenyl chloride, 9-tetradecenyl acetate, 11-tetradecenyl acetate, methyl 11-tetradecenoate, 11-tetradecenyl chloride, methyl 5-hexadecenoate, or 8,10-dodecadienol, or acids, salts, or esters thereof.

36. The method of claim 29 in which the yield of the metathesis product is greater than 15%.

37. The method of claim 29 in which the yield of the metathesis product is greater than 50%.

38. The method of claim 29 in which the yield of the metathesis product is greater than 75%.

39. The method of claim 29 in which the yield of the metathesis product is greater than 90%.

40. The method of claim 29, wherein metathesis catalyst comprises one of: catalyst 823, 801, 876, 848, 826, 785, 816, 794, 846, 824, or 794.

41. A method for synthesizing olefinic alcohols, acetates, aldehydes, carboxylic acids or derivatives thereof in a reaction chamber, comprising:

self-metathesizing a first alpha olefin of form $R-(CH=CH)_k(CH_2)_n(CHX)_g(CH_2)_m-H$, where X is selected from a hydrogen, an alcohol, an acetate, a carboxylate ester, a carboxylic acid, an aldehyde, a halide, or a tosylate, mesylate, or derivatives thereof, and n and m are each selected from zero and an integer less than or equal to 20, in the presence of a first metathesis catalyst to produce a first product of form $(CH=CH)_k[(CH_2)_n(CHX)_g(CH_2)_m—H]_2$ and a first side product of form $RHC=CHR$, where R is selected from H, $CH_2$ or $(CH_2)_n(CHX)_g(CH_2)_m—H$; and cross-metathesizing the first product with a second alpha olefin of form $QCH(CH_2)_rW$, where Q is selected from $CH_2$ or $CH(CH_2)_rW$, r is selected from zero and an integer less than or equal to 20, and W is selected from an alcohol, acetate, carboxylate ester, carboxylic acid, an aldehyde, a halide, hydrogen, or derivatives thereof in the presence of a second metathesis catalyst to form a second product of form $H(CH_2)_m(CHX)_g(CH_2)_n(CH=CH)_p(CH_2)_rW$ or derivatives thereof, where p is less than or equal to the sum of m and n, and a second side product in the form of $CH_2Z$, where Z is selected from $CH_2$ or $CH(CH_2)_n(CHX)_g(CH_2)_mCH_3$ under conditions of sufficiently high temperature and/or sufficiently low pressure such that the second side product evaporates out of the reaction chamber.

42. The method of claim 41, wherein the first or second metathesis catalyst are the same and comprise a catalyst selected from Class I–IV metathesis catalysts.

43. The method of claim 41, wherein the step of self metathesizing is performed under conditions of sufficiently high temperature and/or sufficiently low pressure such that the first side product evaporates out of the reaction chamber.

44. The method of claim 41, wherein the first product comprises 5-decene or 5-decenoic acid or a salt or ester thereof.

45. The method of claim 41, wherein the second product comprises 5-decenyl acetate or an acid, salt, or ester thereof.

46. The method of claim 41, wherein the second product comprises 9-tetradecenyl formate or an acid, salt, or ester thereof.

47. The method of claim 41, wherein the first product comprises 11-tetradecenyl acetate or 11-tetradecenoic acid or a salt or ester thereof.

48. The method of claim 41, wherein the first product comprises methyl 5-hexadecenyl acetate or methyl 5-hexadecenoic acid or a salt or ester thereof.

49. The method of claim 41, wherein the first product comprises 11-docosene or 11-docosenoic acid or a salt or ester thereof.

50. The method of claim 49, wherein the second product comprises (5R,6S)-6-acetoxy-5-hexadecanolide or an acid, salt, or ester thereof.

51. The method of claim 41, wherein the first and/or second catalyst comprises one of: catalyst 823, 801, 876, 848, 826, 785, 816, 794, 846, 824, or 794.

52. A method of synthesizing an omega-haloalkyl product, comprising:
selecting an alpha-omega-diacetoxy alkene;
selecting an alpha-omega-dihalide; and
cross-metathesizing the alpha-omega-diacetoxy alkene with the alpha-omega-dihalide in the presence of a metathesis catalyst to produce an omega-haloalkenyl acetate.

53. The method of claim 52 in which the omega-haloalkenyl acetate, the alpha-omega-diacetoxy alkene, and the alpha-omega-dihalide are produced by self-metathesis of the alpha-olefins under vacuum or at sufficiently high temperatures to obtain high converisons to products.

54. The method of claim 52 in which the omega-haloalkenyl acetate, the alpha-omega-diacetoxy alkene, and the alpha-omega-dihalide have respective first, second, and third boiling points, and the first boiling point is different from the second and third boiling points by at least 5° C.

55. The method of claim 52 in which the omega-haloalkenyl acetate, the alpha-omega-diacetoxy alkene, and the alpha-omega-dihalide have respective first, second, and third boiling points, and the first boiling point is different from the second and third boiling points by at least 20° C.

56. The method of claim 52 in which the omega-haloalkenyl acetate, the alpha-omega-diacetoxy alkene, and the alpha-omega-dihalide have respective first, second, and third boiling points, and the first boiling point is different from the second and third boiling points by at least 40° C.

57. The method of claim 52 further comprising:
separating the omega-haloalkenyl acetate from the alpha-omega-diacetoxy alkene and the alpha-omega-dihalide by distillation.

58. The method of claim 52 further comprising:
reducing and deacetylating the omega-haloalkenyl acetate to produce an omega-haloalkanol.

59. The method of claim 58 in which the omega-haloalkanol comprises 8-bromooctan-1-ol or 8-chlorooctan-1-ol.

60. The method of claim 58 in which the omega-haloalkanol comprises 6-bromohexan-1-ol and 6-chlorohexan-1-ol.

61. The method of claim 52 further comprising:
reducing the omega-haloalkenyl acetate to produce an omega-haloalkanyl acetate.

62. The method of claim 52 in which the omega-haloalkenyl acetate comprises 8-chloro-5-octenyl acetate.

63. The method of claim 52 in which the metathesis catalyst comprises a catalyst selected from Class I–IV.

64. The method of claim 63, wherein metathesis catalyst comprises one of: catalyst 823, 801, 876, 848, 826, 785, 816, 794, 846, 824, or 794.

65. A method for synthesizing a stereo-specific metathesis product, comprising:
selecting an olefin;
selecting a vinyl borate;
cross-metathesizing the olefin and the vinyl borate in the presence of a metathesis catalyst selected from Class I–IV metathesis catalysts to form the stereo-specific metathesis product.

66. The method of claim 65, wherein a terminal olefin is cross metathesis with vinyl borate to yield and alkenyl borate ester.

67. The method of claim 65, wherein an internal olefin is cross metathesis with vinyl borate to yield alkenyl borate ester.

68. The method of claim 66, wherein the cross metathesis product can be purified by distillation or chromatography.

69. The method of claim 67, wherein the cross metathesis product can be purified by distillation or chromatography.

70. The method of claim 68, wherein the cross metathesis product can be purified by distillation to yield pure trans and cis alkenyl borate ester.

71. The method of claim 69, wherein the cross metathesis product can be purified by distillation to yield pure trans and cis alkenyl borate ester.

72. The method of claim 70, wherein the cross metathesis product can be converted into pure trans halo-alkene or pure cis-halo-alkene by the proper reaction conditions.

73. The method of claim 65, wherein the cross metathesis reaction of vinyl borate and a trans:cis mixture of an internal olefin can be used to increase the trans isomeric ratio of the initial olefin mixture.

74. The method of claim 65, where the alkenyl borate ester is reacted under Suzuki conditions to yield an olefin product.

75. The method of claim 65, where the alkenyl borate ester is reacted under palladium catalyst conditions to yield an olefin product.

76. The method of claim 65, where the product is E9,Z11-hexadecadienal.

77. The method of claim 65, where the product is E-5-decenyl acetate.

78. The method of claim 65, where the product is E-11-tetradecenyl acetate.

79. The method of claim 65, where the product is E7,Z9-dodecadienyl acetate.

80. The method of claim 65, where the product is E8,Z10-pentadecadienyl acetate.

81. The method of claim 65, where the product is E3,Z5-dodecadienyl acetate.

82. The method of claim 65, wherein metathesis catalyst comprises one of: catalyst 823, 801, 876, 848, 826, 785, 816, 794, 846, 824, or 794.

83. A method of removing a metathesis catalyst from a reaction mixture including a metathesis product or reactant, comprising:
    introducing an amount of a water soluble phosphine or a water soluble phosphite into the reaction mixture wherein the metathesis catalyst is selected Class I–IV metathesis catalysts;
    mixing the reaction mixture to create an aqueous phase; and
    removing the aqueous phase containing the metathesis catalyst.

84. The method of claim 83 in which the water soluble phosphine comprises trishydroxymethyl phosphine.

85. The method of claim 83 in which the water soluble phosphine or water soluble phosphite comprises an acyclic phosphine or phosphite having the formula shown in FIG. 10B.

86. The method of claim 83 in which the water soluble phosphine or water soluble phosphite comprises a cyclic phosphine or phosphite having the formula shown in FIG. 10C.

87. The method of claim 83 further comprising heating the reaction mixture to a temperature between about 18° C.–200° C.

88. The method of claim 83 further comprising heating the reaction mixture to a temperature between about 45° C.–100° C.

89. The method of claim 83 further comprising heating the reaction mixture to a temperature between about 50° C.–75° C.

90. The method of claim 83, after removing the aqueous phase, further comprising:
    adding water to the reaction mixture;
    mixing the reaction mixture to create a subsequent aqueous phase having an apparent color;
    removing the subsequent aqueous phase containing the metathesis catalyst; and
    repeating the steps of adding, mixing, and removing until the subsequent aqueous phase is substantially colorless.

91. The method of claim 83 in which the metathesis catalyst comprises one of: catalyst 823, 801, 876, 848, 826, 785, 816, 794, 846, 824, or 794.

92. The method of claim 83 in which the amount of the water soluble phosphine comprises about 6 to 100 moles per mole of the metathesis catalyst.

93. A method for preparing a polyhydroxyl phosphine or a polyhydroxyaryl phosphine, comprising:
    selecting a polyhydroxyalkyl-hydroxymethyl phosphoniun halide salt or a polyhydroxyaryl-hydroxymethyl phosphoniun halide salt;
    treating the salt with a substantially molar equivalent of base to produce the polyhydroxyl phosphine or the polyhydroxyaryl phosphine.

94. The method of claim 93 in which the polyhydroxyalkyl-hydroxymethyl phosphoniun halide salt comprises tetrakis hydroxymethyl phosphonium chloride and the polyhydroxyl phosphine comprises trishydroxymethyl phosphine.

95. The method of claim 94 in which the base is potassium hydroxide or sodium hydroxide.

96. The method of claim 95 in which preparation is made in an isopropanol solution.

97. A method for synthesizing (5R,6S)-6-acetoxy-5-hexadecanolide, comprising the steps of:
    cross-metathesizing meadowfoam oil, methyl 5-hexadecenoate, hexenoic acid derivatives, hexenal derivatives, or hexenol derivatives with 1-dodecene or 11-docosene in the presence of a metathesis catalyst to form a first product with a double bond;
    oxidizing the double bond to form a second product;
    and lactonizing and acetylating the second product to form (5R,6S)-6-acetoxy-5-hexadecanolide.

98. The method of claim 97, wherein the 11-docosene is formed by self-metathesizing 1-dodecene in the presence of the metathesis catalyst and under a vacuum having a pressure of less than 50 mmHg.

99. The method of claim 97, further comprising:
    producing the (5R,6S)-6-acetoxy-5-hexadecanolide at a cost of less than $3.00 U.S. per gram.

100. The method of claim 97, further comprising:
    producing the (5R,6S)-6-acetoxy-5-hexadecanolide in a time period of less than 120 hours.

101. The method of claim 97, further comprising:
    producing the (5R,6S)-6-acetoxy-5-hexadecanolide in a time period of less than 60 hours.

102. The method of claim 97, further comprising:
    producing the (5R,6S)-6-acetoxy-5-hexadecanolide in a time period of less than 40 hours.

103. The method of claim 97 in which the metathesis catalyst comprises a catalyst selected from Class I–IV.

104. The method of claim 103, wherein metathesis catalyst comprises one of: catalyst 823, 801, 876, 848, 826, 785, 816, 794, 846, 824, or 794.

105. A method for synthesizing 5-decenyl acetate, comprising the steps of:
    self-metathesizing 1-hexene in the presence of a first catalyst to form a product;
    cross-metathesizing the product with an alcohol- or acetate-protected hexene or derivative thereof in the presence of a second catalyst to form 5-decenyl acetate or derivative thereof and a side product.

106. The method of claim 105, wherein the first or second catalyst comprises catalyst 823.

107. The method of claim 105, wherein the first or second catalyst comprises catalyst 848.

108. The method of claim 105, wherein the product comprises 5-decene.

109. The method of claim 105, further comprising:
    applying vacuum during the step of cross-metathesizing.

110. The method of claim 109 wherein the vacuum has a pressure of less than 50 mmHg.

111. The method of claim 105, wherein the side product comprises 1-hexene.

112. The method of claim 105, further comprising:
producing 5-decenyl acetate at a gross yield of greater than 40 percent.

113. The method of claim 112, further comprising:
producing 5-decenyl acetate at a gross yield of greater than 70 percent.

114. The method of claim 105, further comprising:
producing 5-decenyl acetate at a trans:cis isomeric ratio of greater than 80:20.

115. The method of claim 105, further comprising:
producing 5-decenyl acetate at a cost of less than $0.50 U.S. per gram.

116. The method of claim 105, further comprising:
producing 5-decenyl acetate in a purity of greater than 95% in a trans:cis isomeric ratio of greater than 80:20 in a time period of less than 100 hours.

117. The method of claim 116, further comprising:
producing 5-decenyl acetate in a time period of less than 25 hours.

118. The method of claim 105, wherein the first or second catalyst comprises:
a catalyst selected from Class I–IV metathesis catalysts.

119. The method of claim 105, wherein the first and second catalysts are the same.

120. The method of claim 105, wherein the acetate-protected hexene comprises 5-hexenoic acid or an ester thereof and wherein the derivative of 5-decenyl acetate is 5-decenoic acid or a salt or ester thereof, the method further comprising:
recrystallizing 5-decenoic acid or a salt or thereof to increase the ratio of trans to cis isomer of 5-decenoic acid or the salt thereof; and
reducing the 5-decenoic acid or the salt or ester thereof to 5-decenol;
acetylating the 5-decenol to produce 5-decenyl acetate having a trans to cis ratio of greater than 90 percent.

121. A method for synthesizing 5-decenyl acetate comprising the steps of:
self-metathesizing 1-hexene in the presence of catalyst 823 to form a mixture of 5-decene and ethylene;
removing the ethylene from the mixture;
cross-metathesizing the 5-decene with a protected hexene having a formula 5-hexene-1-R, where R includes an alcohol, acetate, ether, halide, or ester, in the presence of catalyst 823 to form 1-hexene and 5-decenyl acetate having a trans:cis ratio of greater than 80:20;
performing the cross-metathesizing step under vacuum to remove the 1-hexene as it is formed; and
producing a gross yield of 5-decenyl acetate that is greater than 30 percent.

122. The method of claim 121, wherein the protected hexene is selected from 5-hexen-1-yl acetate or 5-hexen-1-ol.

123. The method of claim 121, wherein the R group is selected from a THP, TMS, or EVE ether, a benzoate or propionate ester, or a chloride, bromide, or iodide halide.

124. A method for synthesizing 5-decenyl acetate, comprising the steps of:
self-metathesizing 5-hexenyl acetate under vacuum and in the presence of a catalyst to form 1,10-diacetoxy-5-decene; and
cross-metathesizing 1,10-diacetoxy-5-decene with 5-decene in the presence of the catalyst to form 5-decenyl acetate.

* * * * *

UNITED STATES PATENT AND TRADEMARK OFFICE
CERTIFICATE OF CORRECTION

PATENT NO. : 6,696,597 B2
DATED : February 24, 2004
INVENTOR(S) : Richard L. Pederson and Robert H. Grubbs It is certified that error appears in the above-identified patent and that said Letters Patent is hereby corrected as shown below:

Column 1,
Line 63, change "bearer.moth" to -- bearer moth --.

Column 6,
Line 5, change "1 tetradecenyl" (one) to -- 11 tetradecenyl -- (eleven).

Column 11,
Line 33, change "C5" to -- $C_5$ --.
Line 48, change "L or L" to -- L or L' --.

Column 12,
Line 11, change "fornula" to -- formula --.

Column 13,
Line 19, change "Class." to -- Class --.

Column 16,
Line 67, delete ":".

Column 26,
Line 1, insert -- , -- after "112 degrees C."

Column 32,
Line 42, change "$(CH_2)_n$—H" to -- $(CH_2)_m$—H --.

Signed and Sealed this

Thirty-first Day of May, 2005

JON W. DUDAS
*Director of the United States Patent and Trademark Office*